(12) United States Patent
Ogo et al.

(10) Patent No.: US 9,328,334 B2
(45) Date of Patent: May 3, 2016

(54) LUCIFERASE DERIVED FROM LUCIDINA ACCENSA

(71) Applicant: OLYMPUS CORPORATION, Tokyo (JP)

(72) Inventors: Katsunori Ogo, Hachioji (JP); Ryutaro Akiyoshi, Hachioji (JP); Mariko Murai, Yokohama (JP); Takashi Kinebuchi, Hino (JP); Hirobumi Suzuki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/023,673

(22) Filed: Sep. 11, 2013

(65) Prior Publication Data

US 2014/0080199 A1 Mar. 20, 2014

Related U.S. Application Data

(63) Continuation of application No. PCT/JP2012/057256, filed on Mar. 14, 2012.

(30) Foreign Application Priority Data

Mar. 15, 2011 (JP) ................................. 2011-057053
Oct. 7, 2011 (JP) ................................. 2011-223121

(51) Int. Cl.
*C12N 9/02* (2006.01)
*C07K 14/435* (2006.01)

(52) U.S. Cl.
CPC ........ *C12N 9/0069* (2013.01); *C07K 14/43563* (2013.01)

(58) Field of Classification Search
CPC ...................... C12N 9/0069; C12Y 113/12004
See application file for complete search history.

(56) References Cited

U.S. PATENT DOCUMENTS

2009/0305353 A1 12/2009 Fujii et al.

FOREIGN PATENT DOCUMENTS

| JP | 2003-512071 A | 4/2003 |
| JP | 2006-301599 A | 11/2006 |
| JP | 2007-97577 A | 4/2007 |
| WO | WO 2006/088109 A1 | 8/2006 |

OTHER PUBLICATIONS

Kajiyama N. et al., "Thermostablization of Firefly Luciferase by a Single Amino Acid Substitution at Position 217", Biochemistry 32(50):13795-13799 (1993).
Kitayama A. et al., "Creation of a Thermostable Firefly Luciferase with pH-Insensitive Luminescent Color", Photochemistry and Photobiology 77(3):333-338 (2003).
Japanese Notice of Reasons for Rejection dated Aug. 18, 2015 received from Application No. 2011-223121, together with an English-language translation.
Chinese Office Action dated Sep. 30, 2015 received from Chinese Application No. 201280013326.7, together with an English-language translation.
Oba, Y., "Identification of a functional luciferase gene in the non-luminous diurnal firefly, Lucidina biplagiata", Insect Molecular Biology (2010), vol. 19, No. 6, pp. 737-743.
Ohba, Nobuyoshi, "External morphology and color patterns of Lucidina accensa and L. biplagiata fireflies (Coleopatera: Lampyridae)", Science Report of the Yokosuka City Museum (2001), No. 48, pp. 117-130.
Stanger-Hall, Kathrin F., "Phylogeny of North American fireflies (Coleoptera: Lampyridae): Implications for the evolution of light signals", Science Direct (2007), vol. 45, No. 1, pp. 33-49.
International Search Report dated Jul. 5, 2012 issued in PCT/JP2012/057256.

*Primary Examiner* — Sheridan Swope
(74) *Attorney, Agent, or Firm* — Scully, Scott, Murphy & Presser, P.C.

(57) ABSTRACT

An object of the invention is to provide a novel and useful luciferase. The luciferase according to the embodiments of the invention is derived from *Lucidina accensa*.

6 Claims, 6 Drawing Sheets

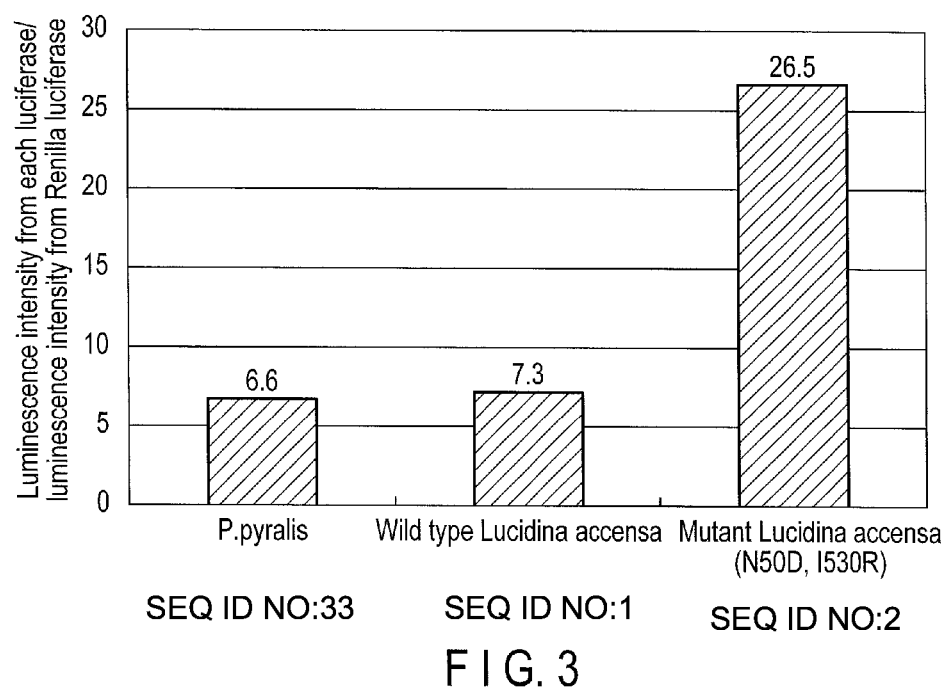
F I G. 3

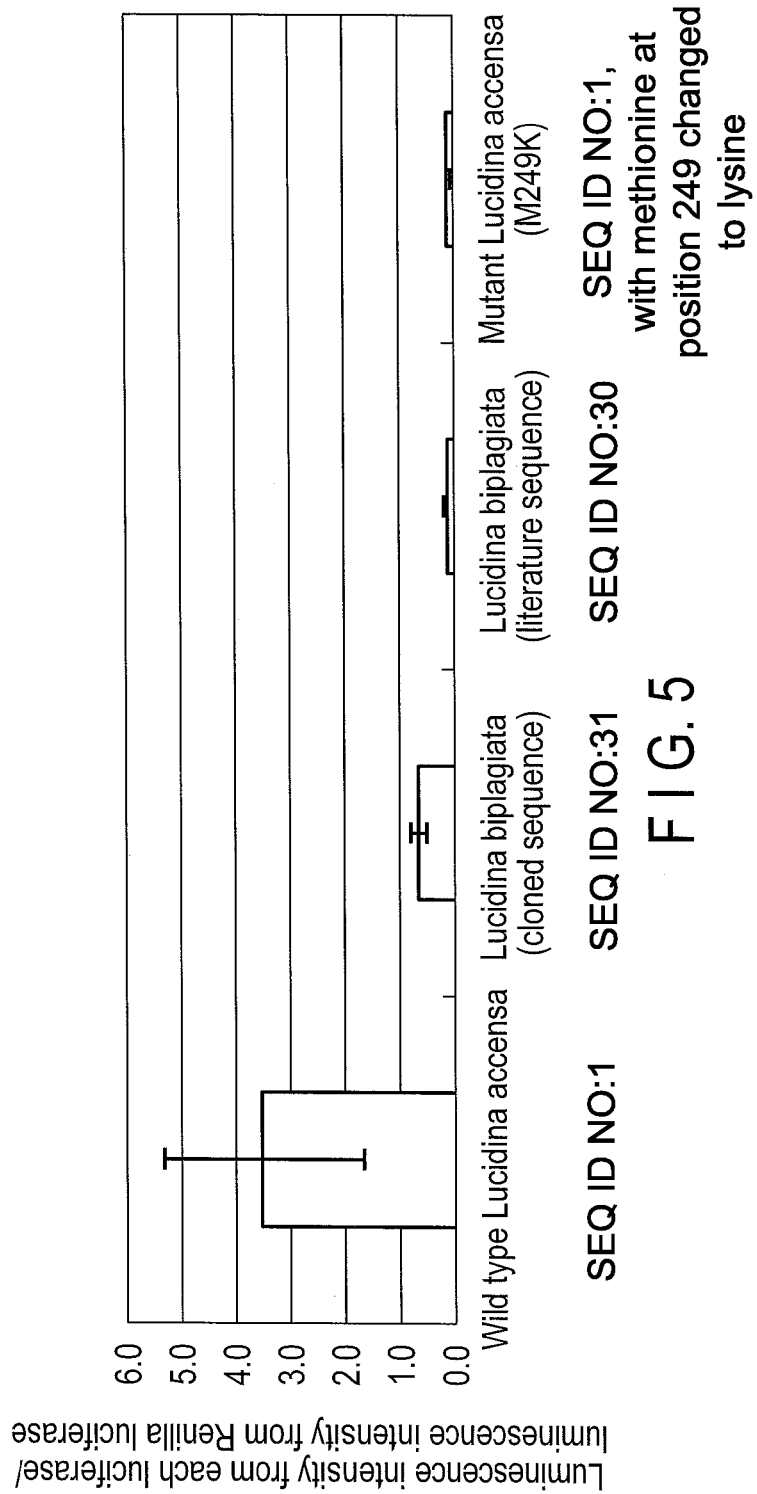
F I G. 5

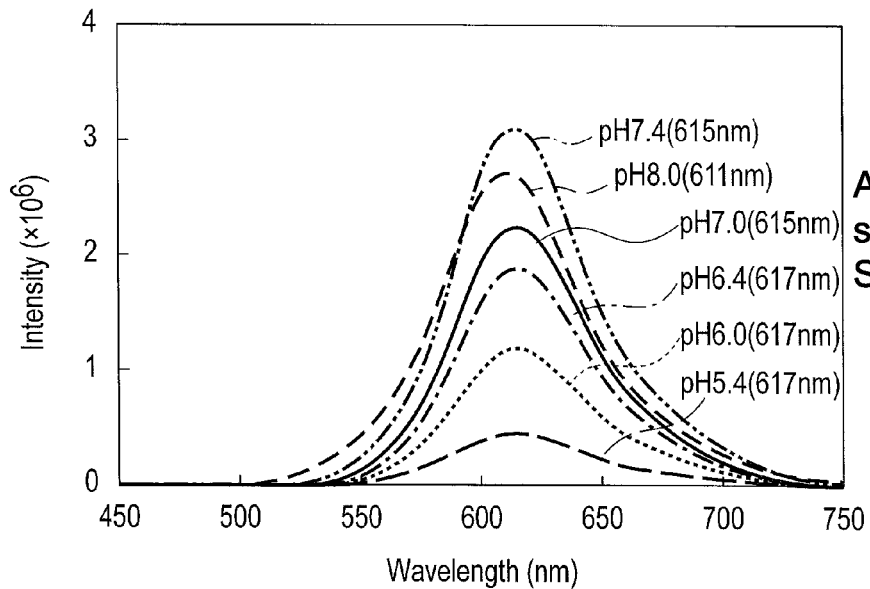
F I G. 6
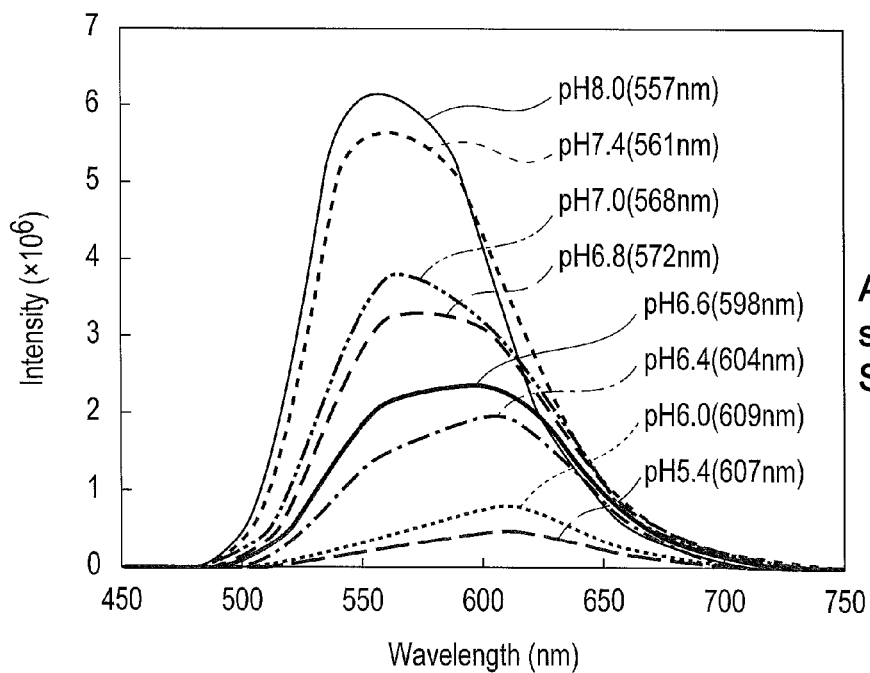
F I G. 7

SEQUENCE LISTING

```
<160> NUMBER OF SEQ ID NOS: 39

<210> SEQ ID NO 1
<211> LENGTH: 549
<212> TYPE: PRT
<213> ORGANISM: Lucidina accensa

<400> SEQUENCE: 1

Met Glu Glu Asp Lys Asn Ile Leu Arg Gly Pro Ala Pro Phe Tyr Pro
1               5                   10                  15

Leu Glu Asp Gly Thr Ala Gly Glu Gln Leu His Arg Ala Met Lys Arg
            20                  25                  30

Tyr Ala Leu Ile Pro Gly Thr Ile Ala Phe Thr Asp Ala His Ala Gly
        35                  40                  45

Val Asn Ile Thr Tyr Ser Glu Tyr Phe Glu Met Ala Cys Arg Leu Ala
    50                  55                  60

Glu Ser Leu Lys Arg Tyr Gly Leu Gly Leu Gln His Arg Ile Val Val
65                  70                  75                  80

Cys Ser Glu Asn Ser Leu Gln Phe Phe Met Pro Val Val Gly Ala Leu
                85                  90                  95

Phe Ile Gly Val Gly Val Ala Pro Ala Asn Asp Ile Tyr Asn Glu Arg
            100                 105                 110

Glu Leu Leu Asn Ser Met Thr Ile Ser Gln Pro Thr Leu Val Phe Cys
        115                 120                 125

Ser Arg Lys Gly Leu Gln Lys Ile Leu Asn Val Gln Lys Lys Leu Pro
    130                 135                 140

Val Ile Gln Lys Ile Ile Ile Leu Asp Thr Lys Glu Asp Tyr Met Gly
145                 150                 155                 160

Phe Gln Ser Met Tyr Ser Phe Val Asp Ser Gln Leu Pro Val Gly Phe
```

```
              165                 170                 175
Asn Glu Tyr Asp Tyr Val Pro Asp Ser Phe Asp Arg Asp Gln Ala Thr
            180                 185                 190

Ala Leu Ile Met Asn Ser Ser Gly Ser Thr Gly Leu Pro Lys Gly Val
            195                 200                 205

Glu Leu Asn His Thr Ser Val Cys Val Arg Phe Ser His Cys Arg Asp
            210                 215                 220

Pro Val Tyr Gly Asn Gln Ile Ile Pro Asp Thr Ala Ile Leu Ser Val
225                 230                 235                 240

Ile Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Phe Phe Ala Lys Ser Thr Leu Ile Asp Lys Tyr
            290                 295                 300

Asp Leu Ser Asn Leu His Glu Ile Ala Ser Gly Gly Ala Pro Leu Ala
305                 310                 315                 320

Lys Glu Val Gly Glu Ala Val Ala Lys Arg Phe Asn Leu Arg Gly Ile
                325                 330                 335

Arg Gln Gly Tyr Gly Leu Thr Glu Thr Thr Ser Ala Val Ile Ile Thr
                340                 345                 350

Pro Glu Gly Asp Asp Lys Pro Gly Ala Val Gly Lys Val Val Pro Phe
                355                 360                 365

Phe Ser Ala Lys Val Val Asp Leu Asp Thr Gly Lys Thr Leu Gly Val
            370                 375                 380

Asn Gln Arg Gly Glu Leu Cys Leu Lys Gly Pro Met Ile Met Lys Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ser Tyr Trp Asp Glu Asp Gly His Phe
                420                 425                 430

Phe Ile Val Asp Arg Leu Lys Ser Leu Ile Lys Tyr Lys Gly Tyr Gln
            435                 440                 445

Val Pro Pro Ala Glu Leu Glu Ser Ile Leu Leu Gln His Pro Phe Ile
            450                 455                 460

Phe Asp Ala Gly Val Ala Gly Ile Pro Asp Asp Glu Ala Gly Glu Leu
465                 470                 475                 480

Pro Ala Ala Val Val Val Leu Glu Glu Gly Lys Thr Met Thr Glu Lys
                485                 490                 495

Glu Ile Met Asp Tyr Val Ala Gly Gln Val Thr Thr Ala Lys Arg Leu
                500                 505                 510

Arg Gly Gly Val Val Phe Val Asp Glu Val Pro Lys Gly Leu Thr Gly
                515                 520                 525

Lys Ile Asp Ala Arg Lys Ile Arg Glu Ile Leu Val Lys Val Lys Lys
530                 535                 540

Thr Lys Ser Lys Leu
545

<210> SEQ ID NO 2
<211> LENGTH: 549
<212> TYPE: PRT
<213> ORGANISM: Lucidina accensa
```

<400> SEQUENCE: 2

```
Met Glu Glu Asp Lys Asn Ile Leu Arg Gly Pro Ala Pro Phe Tyr Pro
1               5                   10                  15

Leu Glu Asp Gly Thr Ala Gly Glu Gln Leu His Arg Ala Met Lys Arg
            20                  25                  30

Tyr Ala Leu Ile Pro Gly Thr Ile Ala Phe Thr Asp Ala His Ala Gly
        35                  40                  45

Val Asp Ile Thr Tyr Ser Glu Tyr Phe Glu Met Ala Cys Arg Leu Ala
50                  55                  60

Glu Ser Leu Lys Arg Tyr Gly Leu Gly Leu Gln His Arg Ile Val Val
65                  70                  75                  80

Cys Ser Glu Asn Ser Leu Gln Phe Phe Met Pro Val Val Gly Ala Leu
                85                  90                  95

Phe Ile Gly Val Gly Val Ala Pro Ala Asn Asp Ile Tyr Asn Glu Arg
            100                 105                 110

Glu Leu Leu Asn Ser Met Thr Ile Ser Gln Pro Thr Leu Val Phe Cys
        115                 120                 125

Ser Arg Lys Gly Leu Gln Lys Ile Leu Asn Val Gln Lys Lys Leu Pro
130                 135                 140

Val Ile Gln Lys Ile Ile Ile Leu Asp Thr Lys Glu Asp Tyr Met Gly
145                 150                 155                 160

Phe Gln Ser Met Tyr Ser Phe Val Asp Ser Gln Leu Pro Val Gly Phe
                165                 170                 175

Asn Glu Tyr Asp Tyr Val Pro Asp Ser Phe Asp Arg Asp Gln Ala Thr
            180                 185                 190

Ala Leu Ile Met Asn Ser Ser Gly Ser Thr Gly Leu Pro Lys Gly Val
        195                 200                 205

Glu Leu Asn His Thr Ser Val Cys Val Arg Phe Ser His Cys Arg Asp
210                 215                 220

Pro Val Tyr Gly Asn Gln Ile Ile Pro Asp Thr Ala Ile Leu Ser Val
225                 230                 235                 240

Ile Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
290                 295                 300

Asp Leu Ser Asn Leu His Glu Ile Ala Ser Gly Gly Ala Pro Leu Ala
305                 310                 315                 320

Lys Glu Val Gly Glu Ala Val Ala Lys Arg Phe Asn Leu Arg Gly Ile
                325                 330                 335

Arg Gln Gly Tyr Gly Leu Thr Glu Thr Thr Ser Ala Val Ile Ile Thr
            340                 345                 350

Pro Glu Gly Asp Asp Lys Pro Gly Ala Val Gly Lys Val Val Pro Phe
        355                 360                 365

Phe Ser Ala Lys Val Val Asp Leu Asp Thr Gly Lys Thr Leu Gly Val
370                 375                 380

Asn Gln Arg Gly Glu Leu Cys Leu Lys Gly Pro Met Ile Met Lys Gly
385                 390                 395                 400

Tyr Val Asn Asn Pro Glu Ala Thr Asn Ala Leu Ile Asp Lys Asp Gly
```

```
                  405                 410                 415
Trp Leu His Ser Gly Asp Ile Ser Tyr Trp Asp Glu Asp Gly His Phe
            420                 425                 430

Phe Ile Val Asp Arg Leu Lys Ser Leu Ile Lys Tyr Lys Gly Tyr Gln
            435                 440                 445

Val Pro Pro Ala Glu Leu Glu Ser Ile Leu Leu Gln His Pro Phe Ile
        450                 455                 460

Phe Asp Ala Gly Val Ala Gly Ile Pro Asp Asp Glu Ala Gly Glu Leu
465                 470                 475                 480

Pro Ala Ala Val Val Leu Glu Gly Lys Thr Met Thr Glu Lys
                485                 490                 495

Glu Ile Met Asp Tyr Val Ala Gly Gln Val Thr Thr Ala Lys Arg Leu
            500                 505                 510

Arg Gly Gly Val Val Phe Val Asp Glu Val Pro Lys Gly Leu Thr Gly
            515                 520                 525

Lys Arg Asp Ala Arg Lys Ile Arg Glu Ile Leu Val Lys Val Lys Lys
        530                 535                 540

Thr Lys Ser Lys Leu
545

<210> SEQ ID NO 3
<211> LENGTH: 1650
<212> TYPE: DNA
<213> ORGANISM: Lucidina accensa

<400> SEQUENCE: 3
atggaagagg ataaaaatat tctgcgcggc ccagcgccat tctatccttt agaagatgga       60
actgcaggcg aacaattaca tagagcgatg aaaagatatg ccttaattcc aggaaccatc      120
gctttcacgg acgctcatgc gggagtaaat atcacgtact ccgaatattt cgaaatggca      180
tgccgattag ctgaaagttt gaaaagatac ggacttggat tacagcacag aattgttgtg      240
tgtagtgaaa attctctaca attttttatg cccgtcgtgg gtgccctatt tattggagtg      300
ggggtcgcac cagcaaatga tatttataac gagcgtgaat tactcaatag catgaccata      360
tcgcagccca ccttagtctt ctgctccaga aaaggattgc aaaaaatttt gaacgtacag      420
aaaaaattac cagtaattca aaaaattatt attctggata ctaaagagga ttatatggga      480
tttcagtcaa tgtactcatt tgttgactcg caattaccag taggtttcaa cgaatatgat      540
tatgtaccgg actccttcga ccgcgatcaa gcaacggcac ttataatgaa ctcctctgga      600
tctactgggt tgccgaaagg ggtggagctt aaccacacga gtgtttgtgt cagattttcg      660
cattgcagag atcctgttta tgggaatcaa attattcccg atactgcaat tttaagtgtt      720
atcccattcc atcatggatt tgggatgttt acaacgctag atatttaat atgtggattt      780 cgagttgtgc tgatgtatag atttgaagaa gaactatttt tgcgatccct tcaagattat      840
aaaattcaga gtgcgttact agtacccacc ctattttcgt tctttgcgaa agcactcta       900 attgacaagt acgatttatc caattacat gaaattgcgt ctggtggtgc tcccctcgca      960
aaagaagttg agaagcagt ggcaaaacgc tttaaccttc gaggtatacg gcaagggtac     1020
ggcttgaccg aaactacatc ggccgttatt attcacctg agggagatga taagccaggt     1080
gcagtcggta aggttgtacc cttctttttcg gcaaaagttg ttgatctcga caccgggaaa     1140
actttgggag ttaatcaaag gggcgaattg tgtctgaaag cccccatgat tatgaaaggt     1200
tatgtaaata accctgaagc tacaaatgcc ttgatcgata aagatggatg gctacactct     1260
```

```
ggtgatatat catactggga cgaagacggt cacttcttca ttgttgatcg cttgaaatct   1320
ttgattaaat ataaagggta ccaggtaccg cccgctgaat tggaatccat tttgctgcaa   1380 catccctttaa tcttcgatgc aggggtggct ggaattcccg acgatgaagc cggtgaattg   1440
cccgctgccg ttgttgtttt agaggaagga aaaactatga ctgaaaaaga aatcatggat   1500
tatgtggcag gtcaggtaac tacagcaaaa cggctacgtg gaggtgtcgt attcgtcgat   1560
gaagtgccga agggtctcac tgggaaaatc gatgcacgaa aaattagaga aatacttgtg   1620
aaagtaaaga aaaccaaatc aaaattgtaa                                    1650

<210> SEQ ID NO 4
<211> LENGTH: 1650
<212> TYPE: DNA
<213> ORGANISM: Lucidina accensa

<400> SEQUENCE: 4
atggaagagg ataaaaatat tctgcgcggc ccagcgccat tctatccttt agaagatgga     60
actgcaggcg aacaattaca tagagcgatg aaaagatatg ccttaattcc aggaaccatc    120
gctttcacgg acgctcatgc gggagtaaat atcacgtact ccgaatattt cgaaatggca    180
tgccgattag ctgaaagttt gaaaagatac ggacttggat tacagcacag aattgttgtg    240
tgtagtgaaa attctctaca attttttatg cccgtcgtgg gtgccctatt tattggagtg    300
ggggtcgcac cagcaaatga tatttataac gagcgtgaat tactcaatag catgaccata    360
tcgcagccca ccttagtctt ctgctccaga aaaggattgc aaaaaatttt gaacgtacag    420
aaaaaattac cagtaattca aaaaattatt attctggata ctaaagagga ttatatggga    480
tttcagtcaa tgtactcatt tgttgactcg caattaccag taggtttcaa cgaatatgat    540
tatgtaccgg actccttcga ccgcgatcaa gcaacggcac ttataatgaa ctcctctgga    600
tctactgggt tgccgaaagg ggtggagctt aaccacacga gtgtttgtgt cagattttcg    660
cattgcagag atcctgttta tgggaatcaa attattcccg atactgcaat tttaagtgtt    720
atcccattcc atcatggatt tgggatgttt acaacgctag atatttaat atgtggattt     780 cgagttgtgc tgatgtatag atttgaagaa gaactatttt tgcgatccct tcaagattat    840
aaaattcaga gtgcgttact agtacccacc ctattttcgt tctttgcgaa aagcactcta    900
attgacaagt acgatttatc caatttacat gaaattgcgt ctggtggtgc tccccctcgca   960 aaagaagttg gagaagcagt ggcaaaacgc tttaaccttc gaggtatacg gcaagggtac   1020
ggcttgaccg aaactacatc ggccgttatt attacacctg agggagatga taagccaggt   1080
gcagtcggta aggttgtacc cttctttcg gcaaaagttg ttgatctcga caccgggaaa    1140
actttgggag ttaatcaaag gggcgaattg tgtctgaaag gccccatgat tatgaaaggt   1200 tatgtaaaata accctgaagc tacaaatgcc ttgatcgata aagatggatg gctacactct   1260
ggtgatatat catactggga cgaagacggt cacttcttca ttgttgatcg cttgaaatct   1320
ttgattaaat ataaagggta ccaggtaccg cccgctgaat tggaatccat tttgctgcaa   1380 catccctttaa tcttcgatgc aggggtggct gggattcccg acgatgaagc cggtgaattg   1440
cccgctgccg ttgttgtttt agaggaagga aaaactatga ctgaaaaaga aatcatggat   1500
tatgtggcag gtcaggtaac tacagcaaaa cggctacgtg gaggtgtcgt attcgtcgat   1560
gaagtgccga agggtctcac tgggaaaatc gatgcacgaa aaattagaga aatacttgtg   1620
aaagtaaaga aaaccaaatc aaaattgtaa                                    1650
```

```
<210> SEQ ID NO 5
<211> LENGTH: 1650
<212> TYPE: DNA
<213> ORGANISM: Lucidina accensa

<400> SEQUENCE: 5
atggaagagg acaagaacat cctgagaggc cctgccccat tctacccct  ggaagatggc    60 acagccggcg agcagctgca ccgggccatg aagagatacg ccctgatccc cggcacaatc   120
gccttcacag acgcccacgc cggagtgaac atcacctaca gcgagtactt cgagatggcc   180
tgtagactgg ccgagagcct gaagagatat ggcctgggac tgcagcatcg gatcgtggtc   240
tgcagcgaga cagcctgca  gttcttcatg cccgtggtcg gagccctgtt catcggagtg   300
ggcgtggccc ctgccaacga catctacaac gagcgcgagc tgctgaacag catgaccatc   360
agccagccca ccctggtgtt ctgcagccgg aagggcctgc agaaaatcct gaacgtgcag   420
aaaaagctgc ccgtgatcca agatcatc   atcctggaca ccaagagga  ctacatgggc   480 ttccagagca tgtacagctt cgtggacagc cagctgcctg tgggcttcaa cgagtacgac   540
tacgtgcccg acagcttcga ccgggatcag gccaccgccc tgatcatgaa cagcagcggc   600
agcaccggcc tgcccaaggg cgtggaactg aaccacacca gcgtgtgcgt gcggttcagc   660
cactgcaggg accccgtgta cggcaaccag atcatccccg acaccgccat cctgagcgtg   720 atcccttcc  accacggctt cggcatgttc accaccctgg ctacctgat  ctgcggcttc   780 cgggtggtgc tgatgtacag attcgaggaa gaactgttcc tgcggagcct gcaggactac   840
aagatccaga gcgccctgct ggtgcctacc ctgttcagct tcttcgccaa gagcacactg   900
atcgataagt acgacctgag caacctgcac gagatcgcca gcggcggagc ccccctggcc   960
aaagaagtgg gagaggccgt cgccaagcgg ttcaacctgc ggggcatcag acagggctac  1020
ggcctgaccg agacaaccag cgccgtgatc atcacccccg agggcgacga taagcctggc  1080
gccgtgggca aggtggtgcc attcttcagc gccaaggtgg tggacctgga caccggcaag  1140
accctgggcg tgaaccagag gggcgagctg tgcctgaagg gccccatgat catgaagggc  1200
tacgtgaaca ccccgaggc  caccaatgcc ctgatcgaca aggacggctg gctgcacagc  1260
ggcgacatca gctactggga cgaggacggc cacttcttca tcgtggaccg gctgaagtcc  1320
ctgatcaagt acaagggcta ccaggtgccc cctgccgagc tggaatccat cctgctgcag  1380 cacccttca  tcttcgatgc cggcgtggcc ggaatccccg atgatgaagc cggcgaactg  1440
cctgccgccg tggtggtgct ggaagaggga aagaccatga ccgagaaaga aatcatggac  1500
tacgtggccg acaggtcac  aaccgccaag agactgagag cgggcgtggt gttcgtggac  1560
gaggtgccaa agggactgac cggcaagatc gacgcccgga agatccgcga gatcctggtg  1620
aaagtgaaaa agaccaagag caagctgtga                                  1650

<210> SEQ ID NO 6
<211> LENGTH: 9
<212> TYPE: PRT
<213> ORGANISM: Artificial
<220> FEATURE:
<223> OTHER INFORMATION: conserved sequence

<400> SEQUENCE: 6

Leu Ile Lys Tyr Lys Gly Tyr Gln Val
1               5

<210> SEQ ID NO 7
<211> LENGTH: 23
```

-continued

<210> SEQ ID NO 7
<211> LENGTH: 23
<212> TYPE: DNA
<213> ORGANISM: Artificial
<220> FEATURE:
<223> OTHER INFORMATION: flexLuc5-ATA Primer
<220> FEATURE:
<221> NAME/KEY: misc_feature
<222> LOCATION: (9)..(9)
<223> OTHER INFORMATION: n is a, c, g, or t

<400> SEQUENCE: 7
acytgrtanc cyttatattt aat                                           23

<210> SEQ ID NO 8
<211> LENGTH: 23
<212> TYPE: DNA
<213> ORGANISM: Artificial
<220> FEATURE:
<223> OTHER INFORMATION: flexLuc5-ATG Primer
<220> FEATURE:
<221> NAME/KEY: misc_feature
<222> LOCATION: (9)..(9)
<223> OTHER INFORMATION: n is a, c, g, or t

<400> SEQUENCE: 8
acytgrtanc cyttatattt gat                                           23

<210> SEQ ID NO 9
<211> LENGTH: 23
<212> TYPE: DNA
<213> ORGANISM: Artificial
<220> FEATURE:
<223> OTHER INFORMATION: flexLuc5-ATT Primer
<220> FEATURE:
<221> NAME/KEY: misc_feature
<222> LOCATION: (9)..(9)
<223> OTHER INFORMATION: n is a, c, g, or t

<400> SEQUENCE: 9
acytgrtanc cyttatattt tat                                           23

<210> SEQ ID NO 10
<211> LENGTH: 23
<212> TYPE: DNA
<213> ORGANISM: Artificial
<220> FEATURE:
<223> OTHER INFORMATION: flexLuc5-ACA Primer
<220> FEATURE:
<221> NAME/KEY: misc_feature
<222> LOCATION: (9)..(9)
<223> OTHER INFORMATION: n is a, c, g, or t

<400> SEQUENCE: 10
acytgrtanc cyttatactt aat                                           23

<210> SEQ ID NO 11
<211> LENGTH: 23
<212> TYPE: DNA
<213> ORGANISM: Artificial
<220> FEATURE:
<223> OTHER INFORMATION: flexLuc5-ACG Primer
<220> FEATURE:
<221> NAME/KEY: misc_feature
<222> LOCATION: (9)..(9)
<223> OTHER INFORMATION: n is a, c, g, or t

<400> SEQUENCE: 11
acytgrtanc cyttatactt gat                                           23

<210> SEQ ID NO 12

```
<211> LENGTH: 23
<212> TYPE: DNA
<213> ORGANISM: Artificial
<220> FEATURE:
<223> OTHER INFORMATION: flexLuc5-ACT Primer
<220> FEATURE:
<221> NAME/KEY: misc_feature
<222> LOCATION: (9)..(9)
<223> OTHER INFORMATION: n is a, c, g, or t

<400> SEQUENCE: 12
acytgrtanc cyttatactt tat                                          23

<210> SEQ ID NO 13
<211> LENGTH: 23
<212> TYPE: DNA
<213> ORGANISM: Artificial
<220> FEATURE:
<223> OTHER INFORMATION: flexLuc5-GTA Primer
<220> FEATURE:
<221> NAME/KEY: misc_feature
<222> LOCATION: (9)..(9)
<223> OTHER INFORMATION: n is a, c, g, or t

<400> SEQUENCE: 13
acytgrtanc cyttgtattt aat                                          23

<210> SEQ ID NO 14
<211> LENGTH: 23
<212> TYPE: DNA
<213> ORGANISM: Artificial
<220> FEATURE:
<223> OTHER INFORMATION: flexLuc5-GTG Primer
<220> FEATURE:
<221> NAME/KEY: misc_feature
<222> LOCATION: (9)..(9)
<223> OTHER INFORMATION: n is a, c, g, or t

<400> SEQUENCE: 14
acytgrtanc cyttgtattt gat                                          23

<210> SEQ ID NO 15
<211> LENGTH: 23
<212> TYPE: DNA
<213> ORGANISM: Artificial
<220> FEATURE:
<223> OTHER INFORMATION: flexLuc5-GTT Primer
<220> FEATURE:
<221> NAME/KEY: misc_feature
<222> LOCATION: (9)..(9)
<223> OTHER INFORMATION: n is a, c, g, or t

<400> SEQUENCE: 15
acytgrtanc cyttgtattt tat                                          23

<210> SEQ ID NO 16
<211> LENGTH: 23
<212> TYPE: DNA
<213> ORGANISM: Artificial
<220> FEATURE:
<223> OTHER INFORMATION: flexLuc5-GCA Primer
<220> FEATURE:
<221> NAME/KEY: misc_feature
<222> LOCATION: (9)..(9)
<223> OTHER INFORMATION: n is a, c, g, or t

<400> SEQUENCE: 16
acytgrtanc cyttgtactt aat                                          23
```

```
<210> SEQ ID NO 17
<211> LENGTH: 23
<212> TYPE: DNA
<213> ORGANISM: Artificial
<220> FEATURE:
<223> OTHER INFORMATION: flexLuc5-GCG Primer
<220> FEATURE:
<221> NAME/KEY: misc_feature
<222> LOCATION: (9)..(9)
<223> OTHER INFORMATION: n is a, c, g, or t

<400> SEQUENCE: 17
acytgrtanc cyttgtactt gat                                          23

<210> SEQ ID NO 18
<211> LENGTH: 23
<212> TYPE: DNA
<213> ORGANISM: Artificial
<220> FEATURE:
<223> OTHER INFORMATION: flexLuc5-GCT Primer
<220> FEATURE:
<221> NAME/KEY: misc_feature
<222> LOCATION: (9)..(9)
<223> OTHER INFORMATION: n is a, c, g, or t

<400> SEQUENCE: 18
acytgrtanc cyttgtactt tat                                          23

<210> SEQ ID NO 19
<211> LENGTH: 23
<212> TYPE: DNA
<213> ORGANISM: Artificial
<220> FEATURE:
<223> OTHER INFORMATION: GeneRacer5' Primer

<400> SEQUENCE: 19
cgactggagc acgaggacac tga                                          23

<210> SEQ ID NO 20
<211> LENGTH: 26
<212> TYPE: DNA
<213> ORGANISM: Artificial
<220> FEATURE:
<223> OTHER INFORMATION: GeneRacer5' Nested Primer

<400> SEQUENCE: 20
ggacactgac atggactgaa ggagta                                       26

<210> SEQ ID NO 21
<211> LENGTH: 19
<212> TYPE: DNA
<213> ORGANISM: Artificial
<220> FEATURE:
<223> OTHER INFORMATION: M13-F(-29) Primer

<400> SEQUENCE: 21
cacgacgttg taaaacgac                                               19

<210> SEQ ID NO 22
<211> LENGTH: 18
<212> TYPE: DNA
<213> ORGANISM: Artificial
<220> FEATURE:
<223> OTHER INFORMATION: M13 Reverse Primer

<400> SEQUENCE: 22
ggataacaat ttcacagg                                                18
```

<210> SEQ ID NO 23
<211> LENGTH: 1136
<212> TYPE: DNA
<213> ORGANISM: Lucidina accensa

<400> SEQUENCE: 23

```
gattcgagat agtgctagtc aaaagctaat attttttcaa aatggaagag gataaaaata      60
ttctgcgcgg cccagcgcca ttctatcctt tagaagatgg aactgcaggc gaacaattac     120
atagagcgat gaaaagatat gccttaattc caggaaccat cgctttcacg gacgctcatg     180
cgggagtaaa tatcacgtac tccgaatatt cgaaatggc atgccgatta gctgaaagtt      240
tgaaaagata cggacttgga ttacagcaca gaattgttgt gtgtagtgaa aattctctac     300
aattttttat gcccgtcgtg ggtgccctat ttattggagt gggggtcgca ccagcaaatg     360
atatttataa cgagcgtgaa ttactcaata gcatgaccat atcgcagccc accttagtct     420
tctgctccag aaaaggattg caaaaaattt tgaacgtaca gaaaaaatta ccagtaattc     480
aaaaaattat tattctggat actaaagagg attatatggg atttcagtca atgtactcat     540
ttgttgactc gcaattacca gtaggtttca acgaatatga ttatgtaccg gactccttcg     600
accgcgatca agcaacggca cttataatga actcctctgg atctactggg ttgccgaaag     660
gggtggagct taaccacacg agtgtttgtg tcagattttc gcattgcaga gatcctgttt     720
atgggaatca aattattccc gatactgcaa ttttaagtgt tatcccattc catcatggat     780
ttgggatgtt tacaacgcta ggatatttaa tatgtggatt tcgagttgtg ctgatgtata     840
gatttgaaga agaactattt ttgcgatccc ttcaagatta taaaattcag agtgcgttac     900
tagtacccac cctatttttcg ttctttgcga aaagcactct aattgacaag tacgatttat     960
ccaatttaca tgaaattgcg tctggtggtg ctcccctcgc aaaagaagtt ggagaagcag    1020
tggcaaaacg ctttaacctt cgaggtatac ggcaagggta cggcttgacc gaaactacat    1080
cggccgttat tattacacct gagggagatg ataagccagg tgcagtcggt aaggtt       1136
```

<210> SEQ ID NO 24
<211> LENGTH: 20
<212> TYPE: DNA
<213> ORGANISM: Artificial
<220> FEATURE:
<223> OTHER INFORMATION: JP-Ohoba-Full-F1 Primer

<400> SEQUENCE: 24
gattcgagat agtgctagtc                                                  20

<210> SEQ ID NO 25
<211> LENGTH: 25
<212> TYPE: DNA
<213> ORGANISM: Artificial
<220> FEATURE:
<223> OTHER INFORMATION: GeneRacer3' Primer

<400> SEQUENCE: 25
gctgtcaacg atacgctacg taacg                                            25

<210> SEQ ID NO 26
<211> LENGTH: 23
<212> TYPE: DNA
<213> ORGANISM: Artificial
<220> FEATURE:
<223> OTHER INFORMATION: GeneRacer3' Nested Primer

<400> SEQUENCE: 26

```
cgctacgtaa cggcatgaca gtg                                               23
```

<210> SEQ ID NO 27
<211> LENGTH: 26
<212> TYPE: DNA
<213> ORGANISM: Artificial
<220> FEATURE:
<223> OTHER INFORMATION: JP-Ohoba-Full-F2 Primer

<400> SEQUENCE: 27

```
gattcgagat agtgctagtc aaaagc                                            26
```

<210> SEQ ID NO 28
<211> LENGTH: 20
<212> TYPE: DNA
<213> ORGANISM: Artificial
<220> FEATURE:
<223> OTHER INFORMATION: T7 promoter Primer

<400> SEQUENCE: 28

```
taatacgact cactataggg                                                   20
```

<210> SEQ ID NO 29
<211> LENGTH: 21
<212> TYPE: DNA
<213> ORGANISM: Artificial
<220> FEATURE:
<223> OTHER INFORMATION: T7 Reverse Primer

<400> SEQUENCE: 29

```
ctagttattg ctcagcggtg g                                                 21
```

<210> SEQ ID NO 30
<211> LENGTH: 549
<212> TYPE: PRT
<213> ORGANISM: Lucidina biplagiata

<400> SEQUENCE: 30

```
Met Glu Glu Asp Lys Asn Ile Leu Arg Gly Pro Ala Ala Phe Tyr Pro
1               5                   10                  15

Leu Glu Asp Gly Thr Ala Gly Glu Gln Leu His Arg Ala Met Lys Arg
            20                  25                  30

Tyr Ala Leu Ile Pro Gly Thr Ile Ala Phe Thr Asp Ala His Ala Gly
        35                  40                  45

Val Asn Ile Thr Tyr Ser Glu Tyr Phe Glu Met Ala Cys Arg Leu Ala
    50                  55                  60

Glu Ser Leu Lys Arg Tyr Gly Leu Gly Leu Gln His Arg Ile Val Val
65                  70                  75                  80

Cys Ser Glu Asn Ser Leu Gln Phe Phe Met Pro Val Val Gly Ala Leu
                85                  90                  95

Phe Ile Gly Val Gly Val Ala Pro Ala Asn Asp Ile Tyr Asn Glu Arg
            100                 105                 110

Glu Leu Leu Asn Ser Met Thr Ile Ser Gln Pro Thr Leu Val Phe Cys
        115                 120                 125

Ser Arg Lys Gly Leu Gln Lys Ile Leu Asn Val Gln Lys Lys Leu Pro
    130                 135                 140

Val Ile Gln Lys Ile Ile Ile Leu Asp Thr Lys Glu Asp Tyr Met Gly
145                 150                 155                 160

Phe Gln Ser Met Tyr Ser Phe Val Asp Ser Gln Leu Pro Val Gly Phe
                165                 170                 175
```

Asn Glu Tyr Asp Tyr Val Pro Asp Ser Phe Asp Arg Asp Gln Ala Thr
            180                 185                 190

Ala Leu Ile Met Asn Ser Ser Gly Ser Thr Gly Leu Pro Lys Gly Val
        195                 200                 205

Glu Leu Thr His Thr Ser Val Cys Val Arg Phe Ser His Cys Arg Asp
210                 215                 220

Pro Val Phe Gly Asn Gln Ile Ile Pro Asp Thr Ala Ile Leu Ser Val
225                 230                 235                 240

Ile Pro Phe His His Gly Phe Gly Lys Phe Thr Thr Leu Gly Tyr Leu
                245                 250                 255

Ile Cys Gly Phe Arg Val Val Leu Met Tyr Arg Phe Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ala
305                 310                 315                 320

Lys Glu Val Gly Glu Ala Val Ala Lys Arg Phe Asn Leu Arg Gly Ile
                325                 330                 335

Arg Gln Gly Tyr Gly Leu Thr Glu Thr Thr Ser Ala Val Ile Ile Thr
            340                 345                 350

Pro Glu Gly Asp Asp Lys Pro Gly Ala Val Gly Lys Val Val Pro Phe
        355                 360                 365

Phe Ser Ala Lys Val Val Asp Leu Asp Thr Gly Lys Thr Leu Gly Val
    370                 375                 380

Asn Gln Arg Gly Glu Leu Cys Leu Lys Gly Pro Met Ile Met Lys Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ser Tyr Trp Asp Glu Asp Gly His Phe
            420                 425                 430

Phe Ile Val Asp Arg Leu Lys Ser Leu Ile Lys Tyr Lys Gly Tyr Gln
        435                 440                 445

Val Pro Pro Ala Glu Leu Glu Ser Ile Leu Leu Gln His Pro Phe Ile
    450                 455                 460

Phe Asp Ala Gly Val Ala Gly Ile Pro Asp Asp Glu Ala Gly Glu Leu
465                 470                 475                 480

Pro Ala Ala Val Val Val Leu Glu Glu Gly Lys Thr Met Thr Glu Lys
                485                 490                 495

Glu Ile Met Asp Tyr Val Ala Gly Gln Val Thr Thr Ala Lys Arg Leu
            500                 505                 510

Arg Gly Gly Val Val Phe Val Asp Glu Val Pro Lys Gly Leu Thr Gly
        515                 520                 525

Lys Leu Asp Ala Arg Lys Ile Arg Glu Ile Leu Val Lys Ala Lys Lys
    530                 535                 540

Thr Lys Ser Lys Leu
545

<210> SEQ ID NO 31
<211> LENGTH: 549
<212> TYPE: PRT
<213> ORGANISM: Lucidina biplagiata

<400> SEQUENCE: 31

```
Met Glu Glu Asp Lys Asn Ile Leu Arg Gly Pro Ala Ala Phe Tyr Pro
1               5                   10                  15

Leu Glu Asp Gly Thr Ala Gly Glu Gln Leu His Arg Ala Met Lys Arg
            20                  25                  30

Tyr Ala Leu Ile Pro Gly Thr Ile Ala Phe Thr Asp Ala His Ala Gly
        35                  40                  45

Val Asn Ile Thr Tyr Ser Glu Tyr Phe Glu Met Ala Cys Arg Leu Ala
    50                  55                  60

Glu Ser Leu Lys Arg Tyr Gly Leu Gly Leu Gln His Arg Ile Val Val
65                  70                  75                  80

Cys Ser Glu Asn Ser Leu Gln Phe Phe Met Pro Val Val Gly Ala Leu
                85                  90                  95

Phe Ile Gly Val Gly Val Ala Pro Ala Asn Asp Ile Tyr Asn Glu Arg
            100                 105                 110

Glu Leu Leu Asn Ser Met Thr Ile Ser Gln Pro Thr Leu Val Phe Cys
        115                 120                 125

Ser Arg Lys Gly Leu Gln Lys Ile Leu Asn Val Gln Lys Lys Leu Pro
    130                 135                 140

Val Ile Gln Lys Ile Ile Leu Asp Thr Lys Glu Asp Tyr Met Gly
145                 150                 155                 160

Phe Gln Ser Met Tyr Ser Phe Val Asp Ser Gln Leu Pro Val Gly Phe
                165                 170                 175

Asn Glu Tyr Asp Tyr Val Pro Asp Ser Phe Asp Arg Asp Gln Ala Thr
            180                 185                 190

Ala Leu Ile Met Asn Ser Ser Gly Ser Thr Gly Leu Pro Lys Gly Val
        195                 200                 205

Glu Leu Thr His Thr Ser Val Cys Val Arg Phe Ser His Cys Arg Asp
    210                 215                 220

Pro Val Phe Gly Asn Gln Ile Ile Pro Asp Thr Ala Ile Leu Ser Val
225                 230                 235                 240

Ile Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ala
305                 310                 315                 320

Lys Glu Val Gly Glu Ala Val Ala Lys Arg Phe Asn Leu Arg Gly Ile
                325                 330                 335

Arg Gln Gly Tyr Gly Leu Thr Glu Thr Thr Ser Ala Val Ile Ile Thr
            340                 345                 350

Pro Glu Gly Asp Asp Lys Pro Gly Ala Val Gly Lys Val Val Pro Phe
        355                 360                 365

Phe Ser Ala Lys Val Val Asp Leu Asp Thr Gly Lys Thr Leu Gly Val
    370                 375                 380

Asn Gln Arg Gly Glu Leu Cys Leu Lys Gly Pro Met Ile Met Lys Gly
385                 390                 395                 400

Tyr Val Asn Asn Pro Glu Ala Thr Asn Ala Leu Ile Asp Lys Asp Gly
                405                 410                 415
```

```
Trp Leu His Ser Gly Asp Ile Ser Tyr Trp Asp Glu Asp Gly His Phe
            420                 425                 430
Phe Ile Val Asp Arg Leu Lys Ser Leu Ile Lys Tyr Lys Gly Tyr Gln
            435                 440                 445
Val Pro Pro Ala Glu Leu Glu Ser Ile Leu Leu Gln His Pro Phe Ile
450                 455                 460
Phe Asp Ala Gly Val Ala Gly Ile Pro Asp Asp Glu Ala Gly Glu Leu
465                 470                 475                 480
Pro Ala Ala Val Val Val Leu Glu Glu Gly Lys Thr Met Thr Glu Lys
                485                 490                 495
Glu Ile Met Asp Tyr Val Ala Gly Gln Val Thr Thr Ala Lys Arg Leu
            500                 505                 510
Arg Gly Gly Val Val Phe Val Asp Glu Val Pro Lys Gly Leu Thr Gly
            515                 520                 525
Lys Leu Asp Ala Arg Lys Ile Arg Glu Ile Leu Val Lys Ala Lys Lys
530                 535                 540
Thr Lys Ser Lys Leu
545

<210> SEQ ID NO 32
<211> LENGTH: 1650
<212> TYPE: DNA
<213> ORGANISM: Lucidina accensa

<400> SEQUENCE: 32
atggaagagg acaagaacat cctgagaggc cctgccccat tctaccccct ggaagatggc      60
acagccggcg agcagctgca ccgggccatg aagagatacg ccctgatccc cggcacaatc     120
gccttcacag acgcccacgc cggagtggac atcacctaca gcgagtactt cgagatggcc     180
tgtagactgg ccgagagcct gaagagatat ggcctgggac tgcagcatcg atcgtggtc      240 tgcagcgaga cagcctgca gttcttcatg cccgtggtcg agccctgtt catcggagtg       300 ggcgtggccc tgccaacga catctacaac gagcgcgagc tgctgaacag catgaccatc      360
agccagccca ccctggtgtt ctgcagccgg aagggcctgc agaaaatcct gaacgtgcag     420
aaaaagctgc ccgtgatcca gaagatcatc atcctggaca ccaaagagga ctacatgggc     480
ttccagagca tgtacagctt cgtggacagc cagctgcctg tgggcttcaa cgagtacgac     540
tacgtgcccg acagcttcga ccgggatcag gccaccgccc tgatcatgaa cagcagcggc     600
agcaccggcc tgcccaaggg cgtggaactg aaccacacca gcgtgtgcgt gcggttcagc     660
cactgcaggg accccgtgta cggcaaccag atcatccccg acaccgccat cctgagcgtg     720 atcccttttcc accacggctt cggcatgttc accaccctgg ctacctgat ctgcggcttc     780 cgggtggtgc tgatgtacag attcgaggaa gaactgttcc tgcggagcct gcaggactac     840
aagatccaga cgccctgct ggtgcctacc ctgttcagct tcttcgccaa gagcacactg     900
atcgataagt acgacctgag caacctgcac gagatcgcca cggcggagc ccccctggcc     960 aaagaagtgg gagaggccgt cgccaagcgg ttcaacctgc ggggcatcag acagggctac    1020
ggcctgaccg agacaaccag cgccgtgatc atcacccccg agggcgacga taagcctggc    1080
gccgtgggca aggtggtgcc attcttcagc gccaaggtgg tggacctgga caccggcaag    1140
accctgggcg tgaaccagag gggcgagctg tgcctgaagg cccccatgat catgaagggc    1200
tacgtgaaca ccccgaggc caccaatgcc ctgatcgaca aggacggctg gctgcacagc    1260
ggcgacatca gctactggga cgaggacggc cacttcttca tcgtggaccg gctgaagtcc    1320
```

```
ctgatcaagt acaagggcta ccaggtgccc cctgccgagc tggaatccat cctgctgcag   1380
cacccctcca tcttcgatgc cggcgtggcc ggaatccccg atgatgaagc cggcgaactg   1440
cctgccgccg tggtggtgct ggaagaggga aagaccatga ccgagaaaga aatcatggac   1500
tacgtggccg acaggtcac aaccgccaag agactgagag cggcgtggt gttcgtggac     1560 gaggtgccaa agggactgac cggcaagaga gacgcccgga agatccgcga gatcctggtg   1620
aaagtgaaaa agaccaagag caagctgtga                                     1650
```

<210> SEQ ID NO 33
<211> LENGTH: 550
<212> TYPE: PRT
<213> ORGANISM: Photinus pyralis

<400> SEQUENCE: 33

```
Met Glu Asp Ala Lys Asn Ile Lys Lys Gly Pro Ala Pro Phe Tyr Pro
  1               5                  10                  15

Leu Glu Asp Gly Thr Ala Gly Glu Gln Leu His Lys Ala Met Lys Arg
             20                  25                  30

Tyr Ala Leu Val Pro Gly Thr Ile Ala Phe Thr Asp Ala His Ile Glu
         35                  40                  45

Val Asp Ile Thr Tyr Ala Glu Tyr Phe Glu Met Ser Val Arg Leu Ala
     50                  55                  60

Glu Ala Met Lys Arg Tyr Gly Leu Asn Thr Asn His Arg Ile Val Val
 65                  70                  75                  80

Cys Ser Glu Asn Ser Leu Gln Phe Phe Met Pro Val Leu Gly Ala Leu
                 85                  90                  95

Phe Ile Gly Val Ala Val Ala Pro Ala Asn Asp Ile Tyr Asn Glu Arg
            100                 105                 110

Glu Leu Leu Asn Ser Met Gly Ile Ser Gln Pro Thr Val Val Phe Val
        115                 120                 125

Ser Lys Lys Gly Leu Gln Lys Ile Leu Asn Val Gln Lys Lys Leu Pro
    130                 135                 140

Ile Ile Gln Lys Ile Ile Ile Met Asp Ser Lys Thr Asp Tyr Gln Gly
145                 150                 155                 160

Phe Gln Ser Met Tyr Thr Phe Val Thr Ser His Leu Pro Pro Gly Phe
                165                 170                 175

Asn Glu Tyr Asp Phe Val Pro Glu Ser Phe Asp Arg Asp Lys Thr Ile
            180                 185                 190

Ala Leu Ile Met Asn Ser Ser Gly Ser Thr Gly Leu Pro Lys Gly Val
        195                 200                 205

Ala Leu Pro His Arg Thr Ala Cys Val Arg Phe Ser His Ala Arg Asp
    210                 215                 220

Pro Ile Phe Gly Asn Gln Ile Ile Pro Asp Thr Ala Ile Leu Ser Val
225                 230                 235                 240

Val Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
            260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ser
```

```
                305                 310                 315                 320
Lys Glu Val Gly Glu Ala Val Ala Lys Arg Phe His Leu Pro Gly Ile
                    325                 330                 335

Arg Gln Gly Tyr Gly Leu Thr Glu Thr Thr Ser Ala Ile Leu Ile Thr
                340                 345                 350

Pro Glu Gly Asp Asp Lys Pro Gly Ala Val Gly Lys Val Val Pro Phe
                355                 360                 365

Phe Glu Ala Lys Val Val Asp Leu Asp Thr Gly Lys Thr Leu Gly Val
370                 375                 380

Asn Gln Arg Gly Glu Leu Cys Val Arg Gly Pro Met Ile Met Ser Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp His Phe
                420                 425                 430

Phe Ile Val Asp Arg Leu Lys Ser Leu Ile Lys Tyr Lys Gly Tyr Gln
                435                 440                 445

Val Ala Pro Ala Glu Leu Glu Ser Ile Leu Leu Gln His Pro Asn Ile
            450                 455                 460

Phe Asp Ala Gly Val Ala Gly Leu Pro Asp Asp Ala Gly Glu Leu
465                 470                 475                 480

Pro Ala Ala Val Val Val Leu Glu His Gly Lys Thr Met Thr Glu Lys
                    485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
                515                 520                 525

Lys Leu Asp Ala Arg Lys Ile Arg Glu Ile Leu Ile Lys Ala Lys Lys
                530                 535                 540

Gly Gly Lys Ile Ala Val
545                 550

<210> SEQ ID NO 34
<211> LENGTH: 549
<212> TYPE: PRT
<213> ORGANISM: Lucidina accensa

<400> SEQUENCE: 34

Met Glu Glu Asp Lys Asn Ile Leu Arg Gly Pro Ala Pro Phe Tyr Pro
1               5                   10                  15

Leu Glu Asp Gly Thr Ala Gly Glu Gln Leu His Arg Ala Met Lys Arg
                20                  25                  30

Tyr Ala Leu Ile Pro Gly Thr Ile Ala Phe Thr Asp Ala His Ala Gly
            35                  40                  45

Val Asn Ile Thr Tyr Ser Glu Tyr Phe Glu Met Ala Cys Arg Leu Ala
50                  55                  60

Glu Ser Leu Lys Arg Tyr Gly Leu Gly Leu Gln His Arg Ile Val Val
65                  70                  75                  80

Cys Ser Glu Asn Ser Leu Gln Phe Phe Met Pro Val Val Gly Ala Leu
                85                  90                  95

Phe Ile Gly Val Gly Val Ala Pro Ala Asn Asp Ile Tyr Asn Glu Arg
                100                 105                 110

Glu Leu Leu Asn Ser Met Thr Ile Ser Gln Pro Thr Leu Val Phe Cys
            115                 120                 125
```

```
Ser Arg Lys Gly Leu Gln Lys Ile Leu Asn Val Gln Lys Lys Leu Pro
130                 135                 140

Val Ile Gln Lys Ile Ile Ile Leu Asp Thr Lys Glu Asp Tyr Met Gly
145                 150                 155                 160

Phe Gln Ser Met Tyr Ser Phe Val Asp Ser Gln Leu Pro Val Gly Phe
                165                 170                 175

Asn Glu Tyr Asp Tyr Val Pro Asp Ser Phe Asp Arg Asp Gln Ala Thr
                180                 185                 190

Ala Leu Ile Met Asn Ser Ser Gly Ser Thr Gly Leu Pro Lys Gly Val
                195                 200                 205

Glu Leu Asn His Thr Ser Val Cys Val Arg Phe Ser His Cys Arg Asp
210                 215                 220

Pro Val Tyr Gly Asn Gln Ile Ile Pro Asp Thr Ala Ile Leu Ser Val
225                 230                 235                 240

Ile Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
                275                 280                 285

Pro Thr Leu Phe Ser Tyr Phe Ala Lys Ser Thr Leu Ile Asp Lys Tyr
290                 295                 300

Asp Leu Ser Asn Leu His Glu Ile Ala Ser Gly Gly Ala Pro Leu Ala
305                 310                 315                 320

Lys Glu Leu Gly Glu Ala Val Ala Lys Arg Phe Asn Leu Arg Gly Ile
                325                 330                 335

Arg Gln Gly Tyr Gly Leu Thr Glu Thr Thr Ser Ala Val Ile Ile Thr
                340                 345                 350

Pro Val Gly Asp Asp Lys Pro Gly Ala Val Gly Lys Val Val Pro Phe
                355                 360                 365

Phe Ser Ala Lys Val Val Asp Leu Asp Thr Gly Lys Thr Leu Gly Val
370                 375                 380

Asn Gln Arg Gly Glu Leu Cys Leu Lys Gly Pro Met Ile Met Lys Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ser Tyr Trp Asp Glu Asp Gly His Phe
                420                 425                 430

Phe Ile Val Asp Arg Leu Lys Ser Leu Ile Lys Tyr Lys Gly Tyr Gln
                435                 440                 445

Val Pro Pro Ala Glu Leu Glu Ser Ile Leu Leu Gln His Pro Phe Ile
450                 455                 460

Phe Asp Ala Gly Val Ala Gly Ile Pro Asp Asp Glu Ala Gly Glu Leu
465                 470                 475                 480

Pro Ala Ala Val Val Val Leu Glu Glu Gly Lys Thr Met Thr Glu Lys
                485                 490                 495

Glu Ile Met Asp Tyr Val Ala Gly Gln Val Thr Thr Ala Lys Arg Leu
                500                 505                 510

Arg Gly Gly Val Val Phe Val Asp Glu Val Pro Lys Gly Leu Thr Gly
                515                 520                 525

Lys Ile Asp Ala Arg Lys Ile Arg Glu Ile Leu Val Lys Val Lys Lys
530                 535                 540

Thr Lys Ser Lys Leu
```

<210> SEQ ID NO 35
<211> LENGTH: 1650
<212> TYPE: DNA
<213> ORGANISM: Lucidina accensa

<400> SEQUENCE: 35

```
atggaagagg acaagaacat cctgagaggc cctgccccat tctacccct ggaagatggc       60
acagccggcg agcagctgca ccgggccatg aagagatacg ccctgatccc cggcacaatc      120
gccttcacag acgcccacgc cggagtgaac atcacctaca gcgagtactt cgagatggcc      180
tgtagactgg ccgagagcct gaagagatat ggcctgggac tgcagcatcg gatcgtggtc      240
tgcagcgaga cagcctgca gttcttcatg cccgtggtcg gagccctgtt catcggagtg       300
ggcgtggccc ctgccaacga catctacaac gagcgcgagc tgctgaacag catgaccatc      360
agccagccca ccctggtgtt ctgcagccgg aagggcctgc agaaaatcct gaacgtgcag      420
aaaaagctgc ccgtgatcca agatcatc atcctgaca ccaaagagga ctacatgggc        480
ttccagagca tgtacagctt cgtggacagc cagctgcctg tgggcttcaa cgagtacgac      540
tacgtgcccg acagcttcga ccgggatcag gccaccgccc tgatcatgaa cagcagcggc      600
agcaccggcc tgcccaaggg cgtggaactg aaccacacca gcgtgtgcgt gcggttcagc      660
cactgcaggg accccgtgta cggcaaccag atcatccccg acaccgccat cctgagcgtg      720
atccctttcc accacggctt cggcatgttc accaccctgg gctacctgat ctgcggcttc      780
cgggtggtgc tgatgtacag attcgaggaa gaactgttcc tgcggagcct gcaggactac      840
aagatccaga gcgccctgct ggtgcctacc ctgttcagct acttcgccaa gagcacactg      900
atcgataagt acgacctgag caacctgcac gagatcgcca cggcggagc ccccctggcc      960
aaagaactgg agagggccgt cgccaagcgg ttcaacctgc ggggcatcag acagggctac     1020
ggcctgaccg agacaaccag cgccgtgatc atcacccccg tgggcgacga taagcctggc     1080
gccgtgggca aggtggtgcc attcttcagc gccaaggtgg tggacctgga caccggcaag     1140
accctgggcg tgaaccagag gggcgagctg tgcctgaagg gccccatgat catgaagggc     1200
tacgtgaaca ccccgaggc caccaatgcc ctgatcgaca aggacggctg gctgcacagc     1260
ggcgacatca gctactggga cgaggacggc cacttcttca tcgtggaccg gctgaagtcc     1320
ctgatcaagt acaagggcta ccaggtgccc cctgccgagc tggaatccat cctgctgcag     1380
cacccttca tcttcgatgc cggcgtggcc ggaatccccg atgatgaagc cggcgaactg     1440
cctgccgccg tggtggtgct ggaagaggga aagaccatga ccgagaaaga aatcatggac     1500
tacgtggccg acaggtcac aaccgccaag agactgagag cgcgcgtggt gttcgtggac     1560
gaggtgccaa agggactgac cggcaagatc gacgcccgga gatccgcga gatcctggtg     1620
aaagtgaaaa agaccaagag caagctgtga                                      1650
```

<210> SEQ ID NO 36
<211> LENGTH: 549
<212> TYPE: PRT
<213> ORGANISM: Lucidina accensa

<400> SEQUENCE: 36

```
Met Glu Glu Asp Lys Asn Ile Leu Arg Gly Pro Ala Pro Phe Tyr Pro
1               5                   10                  15

Leu Glu Asp Gly Thr Ala Gly Glu Gln Leu His Arg Ala Met Lys Arg
            20                  25                  30
```

```
Tyr Ala Leu Ile Pro Gly Thr Ile Ala Phe Thr Asp Ala His Ala Gly
         35                  40                  45

Val Asn Ile Thr Tyr Ser Glu Tyr Phe Glu Met Ala Cys Arg Leu Ala
 50                  55                  60

Glu Ser Leu Lys Arg Tyr Gly Leu Gly Leu Gln His Arg Ile Val Val
 65                  70                  75                  80

Cys Ser Glu Asn Ser Leu Gln Phe Phe Met Pro Val Val Gly Ala Leu
                 85                  90                  95

Phe Ile Gly Val Gly Val Ala Pro Ala Asn Asp Ile Tyr Asn Glu Arg
                100                 105                 110

Glu Leu Leu Asn Ser Met Thr Ile Ser Gln Pro Thr Leu Val Phe Cys
            115                 120                 125

Ser Arg Lys Gly Leu Gln Lys Ile Leu Asn Val Gln Lys Lys Leu Pro
        130                 135                 140

Val Ile Gln Lys Ile Ile Ile Leu Asp Thr Lys Glu Asp Tyr Met Gly
145                 150                 155                 160

Phe Gln Ser Met Tyr Ser Phe Val Asp Ser Gln Leu Pro Val Gly Phe
                165                 170                 175

Asn Glu Tyr Asp Tyr Val Pro Asp Ser Phe Asp Arg Asp Gln Ala Thr
                180                 185                 190

Ala Leu Ile Met Asn Ser Ser Gly Ser Thr Gly Leu Pro Lys Gly Val
            195                 200                 205

Glu Leu Asn His Thr Ser Val Cys Val Arg Phe Ser His Cys Arg Asp
        210                 215                 220

Pro Val Tyr Gly Asn Gln Ile Ile Pro Asp Thr Ala Ile Leu Ser Val
225                 230                 235                 240

Ile Pro Phe His His Gly Phe Gly Met Phe Thr Thr Leu Gly Tyr Leu
                245                 250                 255

Ile Cys Gly Phe Arg Val Val Leu Met Tyr Arg Phe Glu Glu Glu Leu
                260                 265                 270

Phe Leu Arg Ser Leu Gln Asp Tyr Lys Ile Gln Ser Ala Leu Leu Val
        275                 280                 285

Pro Thr Leu Phe Ser Phe Phe Ala Lys Ser Thr Leu Ile Asp Lys Tyr
    290                 295                 300

Asp Leu Ser Asn Leu His Glu Ile Ala Ser Gly Gly Ala Pro Leu Ala
305                 310                 315                 320

Lys Trp Val Gly Glu Ala Val Ala Lys Arg Phe Asn Leu Arg Gly Ile
                325                 330                 335

Arg Gln Gly Tyr Gly Leu Thr Glu Thr Thr Ser Ala Val Ile Ile Thr
                340                 345                 350

Pro Glu Gly Asp Asp Lys Pro Gly Ala Val Gly Lys Val Val Pro Phe
            355                 360                 365

Phe Ser Ala Lys Val Val Asp Leu Asp Thr Gly Lys Thr Leu Gly Val
        370                 375                 380

Asn Gln Arg Gly Glu Leu Cys Leu Lys Gly Pro Met Ile Met Lys Gly
385                 390                 395                 400

Tyr Val Asn Asn Pro Glu Ala Thr Asn Ala Leu Ile Asp Lys Asp Gly
                405                 410                 415

Trp Leu His Ser Gly Asp Ile Ser Tyr Trp Asp Glu Asp Gly His Phe
            420                 425                 430

Phe Ile Val Asp Arg Leu Lys Ser Leu Ile Lys Tyr Lys Gly Tyr Gln
        435                 440                 445
```

```
Val Pro Pro Ala Glu Leu Glu Ser Ile Leu Leu Gln His Pro Phe Ile
        450                 455                 460

Phe Asp Ala Gly Val Ala Gly Ile Pro Asp Asp Glu Ala Gly Glu Leu
465                 470                 475                 480

Pro Ala Ala Val Val Leu Glu Gly Lys Thr Met Thr Glu Lys
                485                 490                 495

Glu Ile Met Asp Tyr Val Ala Gly Gln Val Thr Thr Ala Lys Arg Leu
            500                 505                 510

Arg Gly Gly Val Val Phe Val Asp Glu Val Pro Lys Gly Leu Thr Gly
            515                 520                 525

Lys Ile Asp Ala Arg Lys Ile Arg Glu Ile Leu Val Lys Val Lys Lys
        530                 535                 540

Thr Lys Ser Lys Leu
545

<210> SEQ ID NO 37
<211> LENGTH: 1650
<212> TYPE: DNA
<213> ORGANISM: Lucidina accensa

<400> SEQUENCE: 37
atggaagagg acaagaacat cctgagaggc cctgccccat ctacccccct ggaagatggc      60
acagccggcg agcagctgca ccgggccatg aagagatacg ccctgatccc cggcacaatc     120
gccttcacag acgcccacgc cggagtgaac atcacctaca gcgagtactt cgagatggcc     180
tgtagactgg ccgagagcct gaagagatat ggcctgggac tgcagcatcg gatcgtggtc     240
tgcagcgaga cagcctgca gttcttcatg cccgtggtcg agccctgtt catcggagtg       300 ggcgtggccc tgccaacga catctacaac gagcgcgagc tgctgaacag catgaccatc      360
agccagccca ccctggtgtt ctgcagccgg aagggcctgc agaaaatcct gaacgtgcag     420
aaaaagctgc ccgtgatcca gaagatcatc atcctggaca ccaaagagga ctacatgggc    480
ttccagagca tgtacagctt cgtggacagc cagctgcctg tgggcttcaa cgagtacgac    540
tacgtgcccg acagcttcga ccgggatcag gccaccgccc tgatcatgaa cagcagcggc    600
agcaccggcc tgcccaaggg cgtggaactg aaccacacca gcgtgtgcgt gcggttcagc    660
cactgcaggg accccgtgta cggcaaccag atcatccccg acaccgccat cctgagcgtg    720 atcccttttcc accacggctt cggcatgttc accaccctgg ctacctgat ctgcggcttc     780 cgggtggtgc tgatgtacag attcgaggaa gaactgttcc tgcggagcct gcaggactac    840
aagatccaga gcgccctgct ggtgcctacc ctgttcagct tcttcgccaa gagcacactg    900
atcgataagt acgacctgag caacctgcac gagatcgcca gcggcggagc ccccctggcc    960
aaatgggtgg agaggccgt cgccaagcgg ttcaacctgc ggggcatcag acagggctac   1020
ggcctgaccg agacaaccag cgccgtgatc atcacccccg agggcgacga taagcctggc  1080
gccgtgggca aggtggtgcc attcttcagc gccaaggtgg tggacctgga caccggcaag 1140
accctgggcg tgaaccagag gggcgagctg tgcctgaagg cccccatgat catgaagggc   1200
tacgtgaaca cccccgaggc caccaatgcc ctgatcgaca aggacggctg gctgcacagc   1260
ggcgacatca gctactggga cgaggacggc cacttcttca tcgtggaccg gctgaagtcc  1320
ctgatcaagt acaagggcta ccaggtgccc cctgccgagc tggaatccat cctgctgcag  1380 cacccccttca tcttcgatgc cggcgtggcc ggaatccccg atgatgaagc cggcgaactg 1440
cctgccgccg tggtggtgct ggaagaggga aagaccatga ccgagaaaga aatcatggac  1500
```

| tacgtggccg gacaggtcac aaccgccaag agactgagag gcggcgtggt gttcgtggac | 1560 |
| gaggtgccaa agggactgac cggcaagatc gacgcccgga agatccgcga gatcctggtg | 1620 |
| aaagtgaaaa agaccaagag caagctgtga | 1650 |

<210> SEQ ID NO 38
<211> LENGTH: 1650
<212> TYPE: DNA
<213> ORGANISM: Lucidina accensa

<400> SEQUENCE: 38

| atggaagagg ataaaaatat tctgcgcggc ccagcgccat tctatccttt agaagatgga | 60 |
| actgcaggcg aacaattaca tagagcgatg aaaagatatg ccttaattcc aggaaccatc | 120 |
| gctttcacgg acgctcatgc gggagtaaat atcacgtact ccgaatattt cgaaatggca | 180 |
| tgccgattag ctgaaagttt gaaaagatac ggacttggat tacagcacag aattgttgtg | 240 |
| tgtagtgaaa attctctaca atttttatatg cccgtcgtgg gtgccctatt tattggagtg | 300 |
| ggggtcgcac cagcaaatga tatttataac gagcgtgaat tactcaatag catgaccata | 360 |
| tcgcagccca ccttagtctt ctgctccaga aaggattgc aaaaaatttt gaacgtacag | 420 |
| aaaaaattac cagtaattca aaaaattatt attctggata ctaaagagga ttatatggga | 480 |
| tttcagtcaa tgtactcatt tgttgactcg caattaccag taggtttcaa cgaatatgat | 540 |
| tatgtaccgg actccttcga ccgcgatcaa gcaacggcac ttataatgaa ctcctctgga | 600 |
| tctactgggt tgccgaaagg ggtggagctt aaccacacga gtgtttgtgt cagattttcg | 660 |
| cattgcagag atcctgttta tgggaatcaa attattcccg atactgcaat tttaagtgtt | 720 |
| atcccattcc atcatggatt tgggatgttt acaacgctag atatttaat atgtggattt | 780 |
| cgagttgtgc tgatgtatag atttgaagaa gaactatttt tgcgatccct tcaagattat | 840 |
| aaaattcaga gtgcgttact agtacccacc ctattttcgt actttgcgaa aagcactcta | 900 |
| attgacaagt acgattatc caatttacat gaaattgcgt ctggtggtgc tcccctcgca | 960 |
| aaagaacttg gagaagcagt ggcaaaacgc tttaaccttc gaggtataac gcaagggtac | 1020 |
| ggcttgaccg aaactacatc ggccgttatt attcacctg tgggagatga taagccaggt | 1080 |
| gcagtcggta aggttgtacc cttcttttcg gcaaaagttg ttgatctcga caccgggaaa | 1140 |
| actttgggag ttaatcaaag gggcgaattg tgtctgaaag gccccatgat tatgaaaggt | 1200 |
| tatgtaaata accctgaagc tacaaatgcc ttgatcgata aagatggatg gctacactct | 1260 |
| ggtgatatat catactggga cgaagacggt cacttcttca ttgttgatcg cttgaaatct | 1320 |
| ttgattaaat ataaagggta ccaggtaccg cccgctgaat tggaatccat tttgctgcaa | 1380 |
| catcccttta tcttcgatgc aggggtggct gggattcccg acgatgaagc cggtgaattg | 1440 |
| cccgctgccg ttgttgtttt agaggaagga aaaactatga ctgaaaaaga aatcatggat | 1500 |
| tatgtggcag gtcaggtaac tacagcaaaa cggctacgtg gaggtgtcgt attcgtcgat | 1560 |
| gaagtgccga agggtctcac tgggaaaatc gatgcacgaa aaattagaga aatacttgtg | 1620 |
| aaagtaaaga aaaccaaatc aaaattgtaa | 1650 |

<210> SEQ ID NO 39
<211> LENGTH: 1650
<212> TYPE: DNA
<213> ORGANISM: Lucidina accensa

<400> SEQUENCE: 39

| atggaagagg ataaaaatat tctgcgcggc ccagcgccat tctatccttt agaagatgga | 60 |

-continued

```
actgcaggcg aacaattaca tagagcgatg aaaagatatg ccttaattcc aggaaccatc    120
gctttcacgg acgctcatgc gggagtaaat atcacgtact ccgaatattt cgaaatggca    180
tgccgattag ctgaaagttt gaaaagatac ggacttggat tacagcacag aattgttgtg    240
tgtagtgaaa attctctaca attttttatg cccgtcgtgg gtgccctatt tattggagtg    300
ggggtcgcac cagcaaatga tatttataac gagcgtgaat tactcaatag catgaccata    360
tcgcagccca ccttagtctt ctgctccaga aaaggattgc aaaaaatttt gaacgtacag    420
aaaaaattac cagtaattca aaaaattatt attctggata ctaaagagga ttatatggga    480
tttcagtcaa tgtactcatt tgttgactcg caattaccag taggtttcaa cgaatatgat    540
tatgtaccgg actccttcga ccgcgatcaa gcaacggcac ttataatgaa ctcctctgga    600
tctactgggt tgccgaaagg ggtggagctt aaccacacga gtgtttgtgt cagattttcg    660
cattgcagag atcctgttta tgggaatcaa attattcccg atactgcaat tttaagtgtt    720
atcccattcc atcatggatt tgggatgttt acaacgctag gatatttaat atgtggattt    780
cgagttgtgc tgatgtatag atttgaagaa gaactatttt tgcgatccct tcaagattat    840
aaaattcaga gtgcgttact agtacccacc ctattttcgt tctttgcgaa aagcactcta    900
attgacaagt acgatttatc caatttacat gaaattgcgt ctggtggtgc tcccctcgca    960
aaatggggttg gagaagcagt ggcaaaacgc tttaaccttc gaggtatacg gcaagggtac   1020
ggcttgaccg aaactacatc ggccgttatt attacacctg agggagatga taagccaggt   1080
gcagtcggta aggttgtacc cttctttcg gcaaaagttg ttgatctcga caccgggaaa    1140
actttgggag ttaatcaaag gggcgaattg tgtctgaaag gccccatgat tatgaaaggt   1200
tatgtaaata accctgaagc tacaaatgcc ttgatcgata aagatggatg gctacactct   1260
ggtgatatat catactggga cgaagacggt cacttcttca ttgttgatcg cttgaaatct   1320
ttgattaaat ataaagggta ccaggtaccg cccgctgaat tggaatccat tttgctgcaa   1380
catcccttta tcttcgatgc aggggtggct gggattcccg acgatgaagc cggtgaattg   1440
cccgctgccg ttgttgtttt agaggaagga aaaactatga ctgaaaaaga aatcatggat   1500
tatgtggcag gtcaggtaac tacagcaaaa cggctacgtg gaggtgtcgt attcgtcgat   1560
gaagtgccga agggtctcac tgggaaaatc gatgcacgaa aaattagaga aatacttgtg   1620
aaagtaaaga aaaccaaatc aaaattgtaa                                    1650
```

LUCIFERASE DERIVED FROM LUCIDINA ACCENSA

CROSS REFERENCE TO RELATED APPLICATIONS

This application is a Continuation Application of PCT Application No. PCT/JP2012/057256, filed Mar. 14, 2012 and based upon and claiming the benefit of priority from prior Japanese Patent Applications No. 2011-057053, filed Mar. 15, 2011; and No. 2011-223121, filed Oct. 7, 2011, the entire contents of all of which are incorporated herein by reference.

INCORPORATION BY REFERENCE OF SEQUENCE LISTING

The Sequence Listing in an ASCII text file, named as 30432Z_SequenceListing.txt of 56.4 KB, created on Nov. 21, 2013, and submitted to the United States Patent and Trademark Office via EFS-Web, is incorporated herein by reference.

BACKGROUND OF THE INVENTION

1. Field of the Invention

The present invention relates to a luciferase derived from *Lucidina accensa*.

2. Description of the Related Art

For determining function of cells such as intracellular signal transduction and gene expression, a fluorescent probe such as a fluorescent dye and fluorescent protein and a luminescence probe utilizing a luciferine-luciferase reaction have been used. Especially, for the analysis of gene expression regulation, luminescence measurement is used, which does not cause damage of cell due to exciting light irradiation or a problem of autoluminescence and is excellent in terms of quantitative determination. For example, in the case of observing a cell into which a luciferase gene is introduced, the intensity of expression of the luciferase gene (more specifically, the expression amount) can be determined by measuring luminescence from the cell. The measurement of degree of luminescence is performed by the procedures in which luciferine, adenosine triphosphate (ATP), and the like are added to lysate prepared by lysis of cells, and the lysate is subjected to a quantitative determination using a luminometer including a photoelectric multiplier. Namely, luminescence is measured after lysis of cells, and thus the expression amount of the luciferase gene at a certain time point is determined as the sum of a number of cells. Examples of a method for introducing a luminescent gene such as luciferase gene as a reporter gene are a calcium phosphate method, lipofection method, and electroporation method, and each of these methods is used depending on the purpose and type of cells. When analyzing the expression amount of luciferase with use of an objective DNA fragment ligated to the upstream or downstream of a luciferase gene to be introduced into a cell, it is possible to study of the effect of the DNA fragment on luciferase gene transcription. Further, co-expression of a luciferase gene to be introduced into a cell and the objective gene enables study of the effect of the gene product on luciferase gene expression.

For time-course analysis of the expression amount of a luminescent gene, the degree of luminescence of a living cell needs to be measured over time. Such measurement is carried out by cell cultivation in an incubator provided with a luminometer and quantitative determination of the degree of luminescence from the whole cell population at regular time intervals. Consequently, for example, an expression rhythm having a certain cycle can be analyzed, and temporal change of the expression amount of the luminescent gene in the entire cell can be obtained.

In recent years, in a field of biology and medical science there is increasing necessity of the time course observation of dynamic alterations in living samples with images. In a field of utilizing observation of fluorescence, time lapse or dynamic image pickup has been adopted for understanding function of a protein molecular dynamically. In the conventional technique, time course observation with use of a fluorescent sample has been carried out, for example, observation of moving images for one molecule of a protein provided with an added fluorescent molecule.

In contrast, when a luminescent sample is used for time-course observation, use of a CCD camera equipped with an image intensifier is required since the luminous intensity of the luminescent sample is extremely low. Recently, a microscope equipped with an optical system for observation of luminescent samples has been developed (Jpn. Pat. Appln. KOKAI Publication No. 2006-301599, International Publication No. 2006/088109).

BRIEF SUMMARY OF THE INVENTION

An object of the invention is to provide a novel and useful luciferase.

The luciferase according to the embodiments of the invention is derived from *Lucidina accensa*.

A novel and useful luciferase is provided by the invention.

BRIEF DESCRIPTION OF THE SEVERAL VIEWS OF THE DRAWING

FIG. 3 is a diagram to compare the luminescence intensity obtained from a light emitting reaction in which the wild type luciferase derived from *L. accensa* or a mutant luciferase thereof according to embodiments of the invention, or a luciferase derived from *Photinus pyralis* is used as an enzyme;

FIG. 5 is a diagram to compare the luminescence intensity obtained from a light emitting reaction in which the wild type luciferase derived from *L. accensa* or a mutant (M249K) luciferase thereof according to embodiments of the invention, or a luciferase derived from *L. biplagiata* is used as an enzyme;

FIG. 6 is a light emission spectrum obtained from a light emitting reaction in which a mutant (F294Y, V323L, and E354V) luciferase derived from *L. accensa* according to the embodiments of the invention is used as an enzyme under various pH environments;

FIG. 7 is a light emission spectrum obtained from a light emitting reaction in which a mutant (E322W) luciferase derived from *L. accensa* according to the embodiments of the invention is used as an enzyme under various pH environments;

DETAILED DESCRIPTION OF THE INVENTION

Figure 1:
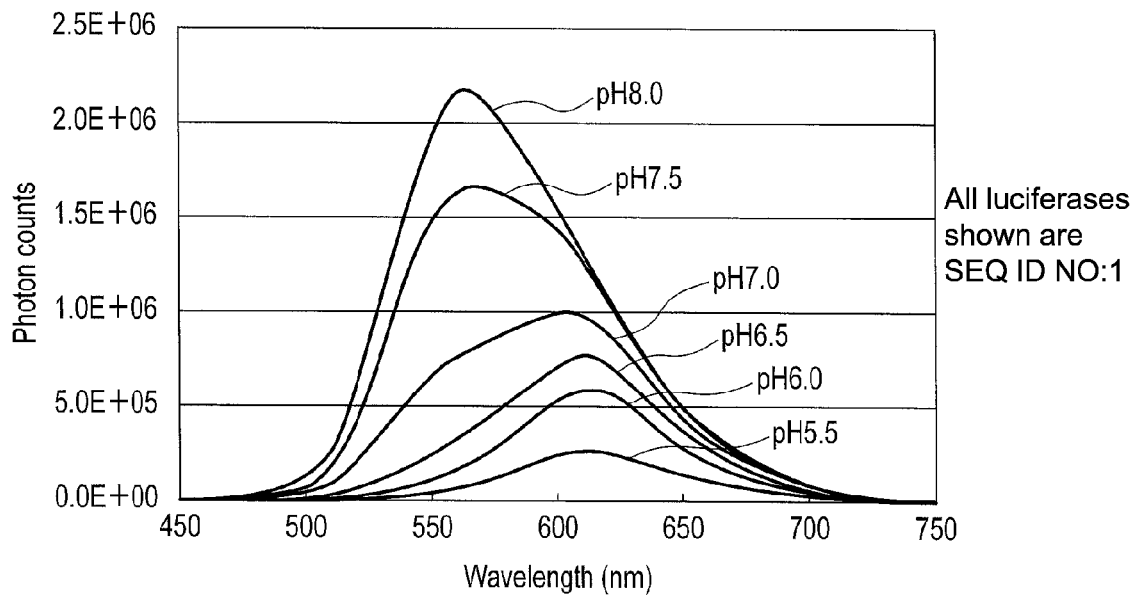
FIG. 1 is a light emission spectrum of a light emitting reaction in which luciferase derived from *L. accensa* according to the embodiments of the invention is used as an enzyme under various pH environments.

One embodiment of the invention relates to a luciferase derived from *Lucidina accensa*.

"Luciferase" generally indicates an enzyme which catalyzes a luminescent chemical reaction. The substrate of this enzyme is called as luciferin. In the presence of ATP, emission of light occurs upon chemical reaction of luciferin because of the catalytic activity of luciferase. Presently, luciferases derived from fireflies and bacteria have been obtained. The luciferase according to the embodiments of the invention also indicates those defined above, but is novel one which has been first obtained from the firefly described below.

*Lucidina accensa* (*L. accensa*) is a firefly belonging to Phylum: Arthropoda, Class: Insecta, Order: Coleoptera, Family: Lampyridae, Genus: *Lucidina*, and it is found that the firefly inhabits mainly mountainous regions of Honshu, Shikoku, and Kyushu of Japan. Further, as a sister species of *L. accensa*, there is a firefly named *Lucidina biplagiata* (*L. biplagiata*), and it is found that the firefly inhabits mainly field regions of Hokkaido, Honshu, Shikoku, and Kyushu of Japan. It is also found that those two fireflies inhabit together a specific area. As used herein, the term "derive" means to contain not only wild type luciferases from *L. accensa* fireflies but also mutants thereof.

Upon image pickup of a luminescent sample having small luminous intensity, it should be exposed for a longer term for obtaining clear image. Such a luminescent sample is used for only limited research. For example, when 30 minutes of exposure is required because of low luminous intensity, time-course image pickup is possible at every 30 minutes but is not at a shorter time interval, and real-time image pickup is also impossible. Upon acquisition of images, plural images should be obtained and compared in order to focus on cells which emit light, and thus it is time-consuming when longer exposure time is required because of low luminous intensity.

By using the luciferase according to the embodiments of the invention, remarkably high luminescence intensity can be obtained in comparison to known luciferases. Thus, the luciferase according to the embodiments of the invention exhibits a particularly advantageous effect when it is used as a reporter for imaging of proteins. More specifically, the luciferase according to the embodiments of the invention enables excellent detection of proteins whose expression amount is small since it can provide a high degree of luminescence even with a small amount. The luciferase according to the embodiments of the invention is capable of reducing the exposure time which is necessary for detection, because of high luminescence intensity. Therefore, it enables the reduction of the interval between image pickups by utilizing the luciferase according to the embodiments of the invention as a reporter for time-course observation, thereby achieving observation which is closer to real-time observation.

The luciferases according to the embodiments of the invention provide luminescence intensity which is at least 1.5 times, at least 2 times, at least 2.5 times, at least 3 times, at least 3.5 times, at least 4 times, at least 4.5 times, at least 5 times, or at least 5.5 times the luminescence intensity of the luciferase derived from *L. biplagiata* (SEQ ID NO: 30 or 31), for example. Further, the luciferases according to the embodiments of the invention provide luminescence intensity which is at least 1.1 times, at least 1.5 times, at least 2 times, at least 2.5 times, at least 3 times, at least 3.5 times, or at least 4 times the luminescence intensity of the luciferase derived from *Photinus pyralis* (a firefly inhabits mainly North America) (SEQ ID NO: 33), for example.

From a light emitting reaction caused by the luciferase according to the embodiments of the invention, a light emission spectrum showing high luminescence intensity in the wavelength of 500 nm to 700 nm can be obtained. The high luminescence intensity can be obtained particularly from the wavelength of 550 nm to 650 nm. Further, the maximum luminescent wavelength of the light emitting reaction that is caused by the luciferase according to the embodiments of the invention can be shifted in response to pH of a surrounding environment. For example, under an environment with pH 8.0 to pH 7.5, the maximum luminescent wavelength is shown near 564 nm. Under an environment with pH 7.0, the maximum luminescent wavelength is shown near 605 nm. Under an environment with pH 6.5 to pH 5.5, the maximum luminescent wavelength is shown near 614 nm. As used herein, the term "maximum luminescent wavelength" indicates a wavelength at which the highest luminescence intensity is obtained from the luciferase-involved light emitting reaction within the range of wavelength for measurement. As used herein, the term "range of wavelength for measurement" indicates the wavelength range of 450 nm to 750 nm, for example.

The luciferase according to the embodiments of the invention may exhibit relatively high stability against degradation compared to existing luciferase. The term "stability against degradation" means that the luciferase is hardly degraded under an environment in which the luciferase is used. Further, the term "stability against degradation" includes not only the stability against degradation by a proteolytic enzyme but also the stability against degradation that does not involve in proteolytic enzyme, for example the stability against degradation caused by heat or mechanical stimulation, or the like. The term "environment in which the luciferase is used" means a solution, a culture, an extracellular fluid, and an intracellular environment or the like. In particular, many proteolytic enzymes are usually present in a culture, an extracellular fluid, or an intracellular environment, and the luciferase according to the embodiments of the invention is resistant to the degradation under such environment. That is, the luciferase according to the embodiments of the invention is not degraded under such environment and can maintain high luminescence intensity. Therefore, the luciferase according to the embodiments of the invention has higher stability against protein degradation compared to the luciferase derived from *L. biplagiata*, for example.

One example of the luciferase according to the embodiments of the invention is those containing the amino acid sequence shown in SEQ ID NO: 1. The luciferase has been obtained from *L. accensa* and received no mutagenesis. As used herein, the term "wild type luciferase" means a wild type luciferase derived from *L. accensa*, unless specifically described otherwise.

Figure 2:
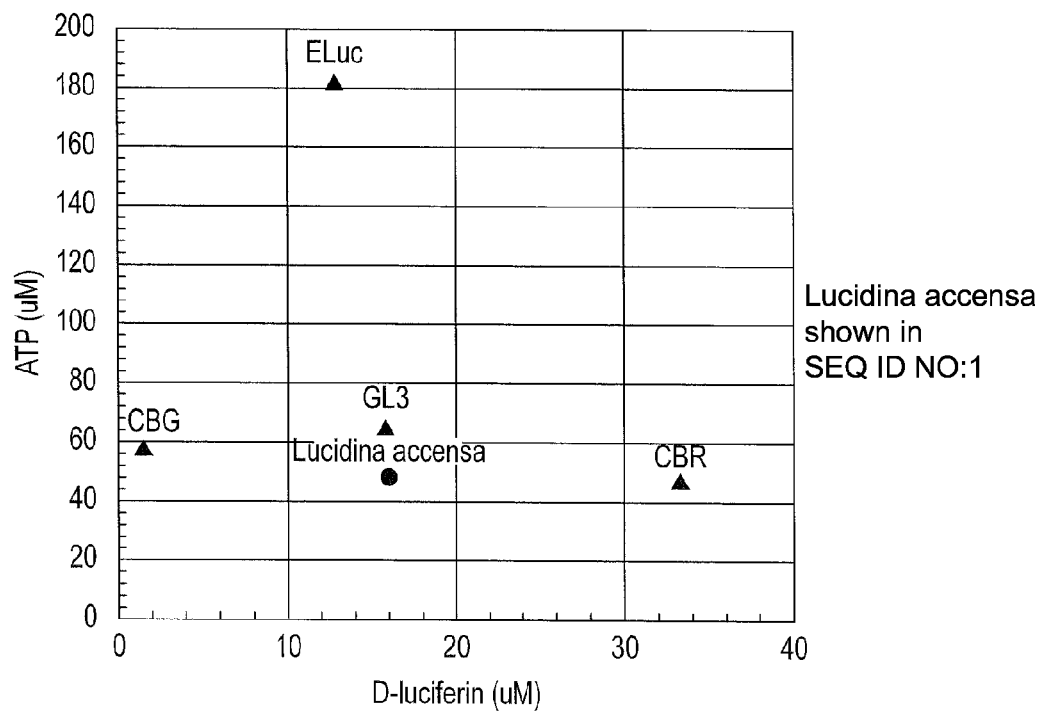
FIG. 2 is a diagram in which Km of various luciferases is plotted.
Figure 4:
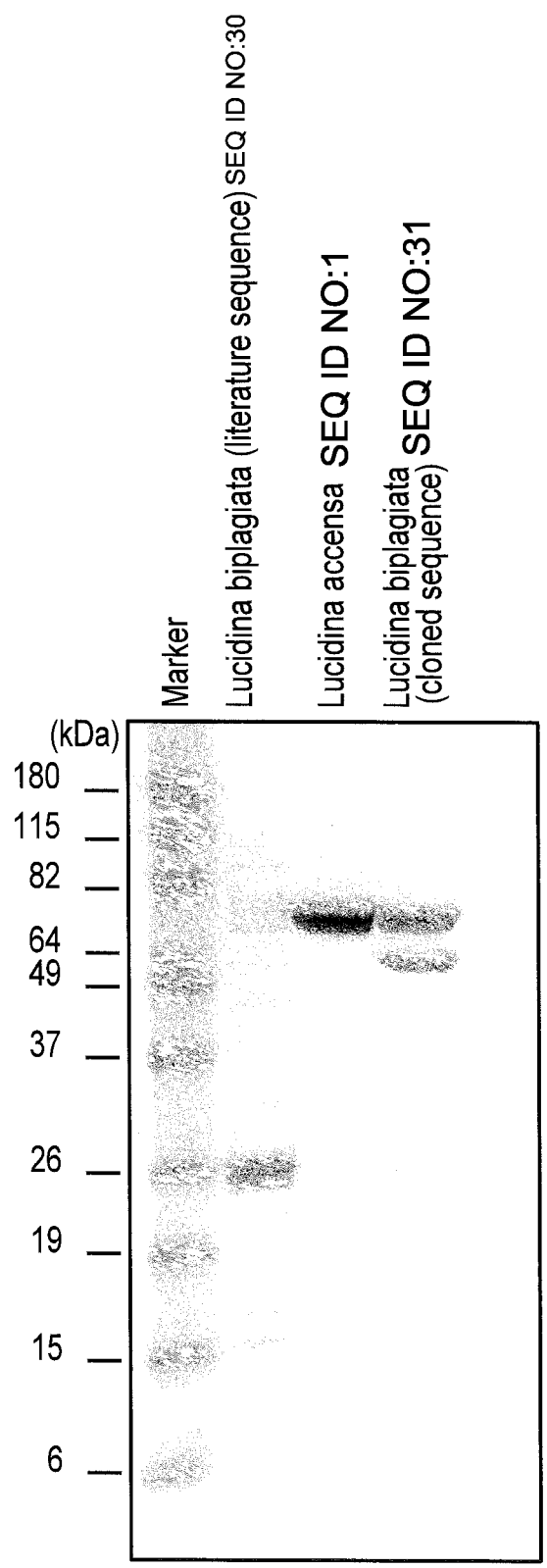
FIG. 4 is a diagram to compare the stability against protein degradation of a luciferase derived from *L. accensa* according to embodiments of the invention and a luciferase derived from *L. biplagiata;*

FIG. 1 is a light emission spectrum of a light emitting reaction in which the wild type luciferase is used as an enzyme. As is shown by the figure, the maximum luminescent wavelength is shifted in response to pH. In particular, the highest luminescence intensity is exhibited under the environment with pH 8, and the maximum luminescent wavelength is near 564 nm. FIG. 2 shows Km values of the wild type luciferase with respect to ATP and D-luciferin. FIGS. 3 and 5 are diagrams to compare the luminescence intensity of a light emitting reaction, in which a known luciferase is used as an enzyme. It is found from the comparison of the left bar and the center bar in FIG. 3 that, when the wild type luciferase is used, the luminescence intensity is increased by at least 1.1 times compared to the case in which the luciferase derived from *P. pyralis* is used. It is also found from the comparison of the three bars at left side in FIG. 5 that, when the wild type luciferase is used, the luminescence intensity is increased by at least 5.5 times compared to the case in which the luciferase derived from *L. biplagiata* is used. FIG. 4 shows the results of comparing stability against degradation between the wild type luciferase and a known luciferase. Specifically, the result was obtained by expressing each luciferase in *E. coli* and the lysate obtained therefrom was subjected to SDS—polyacrylamide gel electrophoresis. The wild type luciferase (i.e., center lane) showed one band near 70 kDa region. Meanwhile, the luciferase derived from *L. biplagiata* (left and right lanes) showed the same band near 70 KDa region as a strongest band while having several minor bands. This result indicates that, while no degradation occurred in the wild type luciferase, the luciferase derived from *L. biplagiata* underwent the degradation.

The wild type luciferase (SEQ ID NO: 1) has a novel sequence that is different from sequences of a known luciferase. Specifically, as shown in the following Table 1, the wild type luciferase has a difference in amino acid residues compared to the amino acid sequence of *L. biplagiata* (SEQ ID NO: 30) that is reported in the literature (Oba Y, Furuhashi M, Inouye S. (2010) Identification of a functional luciferase gene in the non-luminous diurnal firefly, *Lucidina biplagiata*. Molecular Insect Biology 19 (6): 737 to 743) and the amino acid sequence that has been cloned by the inventors of the present invention (SEQ ID NO: 31). The difference between the sequence of *L. biplagiata* reported in the literature and the sequence of *L. biplagiata* shown by the cloning by the inventors lies in that the amino acid at position 249 is lysine and methionine, respectively.

TABLE 1

Difference in amino acid residues among various luciferases

| | Number of amino acid residue having difference | | | | | |
|---|---|---|---|---|---|---|
| | 13 | 211 | 227 | 249 | 530 | 542 |
| *L. accensa* (wild type) (SEQ ID NO: 1) | Pro | Asn | Tyr | Met | Ile | Val |
| *L. biplagiata* (literature sequence) (SEQ ID NO: 30) | Ala | Thr | Phe | Lys | Leu | Ala |
| *L. biplagiata* (cloned sequence) (SEQ ID NO: 31) | Ala | Thr | Phe | Met | Leu | Ala |

The difference in sequence as shown in Table 1 can be explained as follows. Specifically, the luciferase according to the embodiments of the invention has an amino acid sequence which satisfies at least one of the amino acid residue corresponding to the alanine at position 13 of an amino acid sequence shown in SEQ ID NO: 30 is proline, the amino acid residue corresponding to the threonine at position 211 of an amino acid sequence shown in SEQ ID NO: 30 is asparagine, the amino acid residue corresponding to the phenylalanine at position 227 of an amino acid sequence shown in SEQ ID NO: 30 is tyrosine, the amino acid residue corresponding to the lysine at position 249 of an amino acid sequence shown in SEQ ID NO: 30 is methionine, the amino acid residue corresponding to the leucine at position 530 of an amino acid sequence shown in SEQ ID NO: 30 is isoleucine, and the amino acid residue corresponding to the alanine at position 542 of an amino acid sequence shown in SEQ ID NO: 30 is valine, when sequence homology search is carried out for the amino acid sequence of a luciferase derived from *L. biplagiata* (SEQ ID NO: 30). In the luciferase according to the embodiment, the amino acid residues other than those corresponding to position 13, position 211, position 227, position 249, position 530, and position 542 of the amino acid sequence shown in SEQ ID NO: 30 are not specifically limited, and the amino acid residues may be different from the corresponding amino acid residues of the amino acid sequence shown in SEQ ID NO: 30.

The luciferase according to the embodiments of the invention includes not only those of wild type which is derived from *L. accensa*, but also mutant luciferases in which a part of the amino acid sequence of wild type luciferase is mutated. As used herein the term "mutant luciferase" means a mutant luciferase derived from *L. accensa*, unless specifically described otherwise.

The mutation for obtaining a mutant luciferase is a mutation which does not bring any change to properties of a luciferase. For example, it can be a mutation by which no change is brought into a sequence or a domain which has high contribution to the light emitting reaction while a change is brought into a sequence or a domain which has a little contribution to the light emitting reaction. Specifically, it may be a mutation for deleting a region which is not much related to the light emitting reaction, a mutation for inserting a specific sequence to such region, or a mutation for adding a specific sequence to the terminal.

The mutation for obtaining a mutant luciferase may be a mutation for changing properties other than luminescence activity of a luciferase. For example, it may be a mutation for improving experimental workability. Specifically, when a wild type luciferase has a low solubility in a mammal cell, it may be a mutation for increasing the solubility thereof, for example.

Further, the mutation for obtaining a mutant luciferase may be a mutation for improving the properties related to the light emitting reaction. Examples thereof include a mutation for increasing luminescence intensity, a mutation for modifying optimum pH, a mutation for modifying optimum temperature, and a mutation for enhancing stability against degradation.

One example of the luciferase with a mutation for having higher luminescence intensity compared to the wild type luciferase is a mutant luciferase having an amino acid sequence shown in SEQ ID NO: 2. As shown in FIG. 3, the mutant luciferase exhibits at least 4 times of luminescence intensity of that of the luciferase derived from *Photinus pyralis*. It also exhibits at least 3.6 times of luminescence intensity of that of the wild type luciferase derived from *L. accensa*.

Another example of the mutation is a mutation to yield a shift of maximum luminescent wavelength of a light emission spectrum. When a mutant luciferase having such mutation is used as an enzyme for the light emitting reaction, the light emission spectrum in which maximum luminescent wavelength is shifted is obtained compared to a case in which the wild type is used. When the wild type luciferase is used under the environment of pH 7.0, light emission occurs with the maximum luminescent wavelength of near 605 nm. However, due to the mutation, the maximum luminescent wavelength is shifted toward a long wavelength side or a short wavelength side. It is allowable that such shift of the maximum luminescent wavelength by a mutant luciferase occurs only when pH condition for the light emitting reaction is controlled to have specific pH. For example, it is allowable that shift does not occur in the pH range of less than pH 6.5 or pH range of more than pH 7.0 but it occurs in the pH range of 6.5 to 7.0. When such mutant luciferase is expressed within a cell together with the wild type luciferase or other mutant luciferases, they can be distinguished from each other based on the difference in maximum luminescent wavelength. Thus, in a study in which a luciferase is used as a marker, by using a mutant luciferase which exhibits a shift of the maximum luminescent wavelength, selection range of the marker can be broadened.

Another example of the mutation is a mutation to yield modified temperature dependency of luminescence intensity. In other words, it is a mutation by which a catalytic activity for the light emitting reaction is increased over the wild type at specific temperature, and therefore the luminescence intensity at the temperature becomes higher. Such mutation may increase luminescence intensity only within a specific temperature range. For example, it may exhibit the same or lower luminescence intensity than the wild type at a certain temperature but exhibit higher luminescence intensity than the wild type at other temperatures. Examples of the mutant include a luciferase which shows the same activity as the wild type at temperatures commonly used and maintains the same activity at a higher or lower temperature at which the wild type exhibits a reduced activity. Since such mutant luciferase can be used in the temperature range in which the wild type luciferase cannot be used, range of the use of luciferase can be broadened.

The mutation for increasing luminescence intensity, mutation for yielding a shift of maximum luminescent wavelength, and a mutation for modifying the temperature dependency of luminescence intensity can be simultaneously introduced as any combination thereof.

One example of the mutant luciferase which is derived from *L. accensa* according to the embodiments of the invention is a luciferase having an amino acid sequence shown in SEQ ID NO: 34. The amino acid sequence shown in SEQ ID NO: 34 is an amino acid sequence shown in SEQ ID NO: 1 of the wild type luciferase in which phenylalanine (F) residue at position 294 is substituted with tyrosine (Y) residue (F294Y), valine (V) residue at position 323 is substituted with leucine (L) residue (V323L), and glutamic acid (E) residue at position 354 is substituted with valine (V) residue (E354V). The nucleic acid which encodes the mutant luciferase is a nucleic acid having a base sequence shown in SEQ ID NO: 35 or 38. The base sequence shown in SEQ ID NO: 38 includes mutations that are introduced to the base sequence shown in SEQ ID NO: 3 encoding the wild type luciferase for having three substitutions described above on a corresponding amino acid sequence. Meanwhile, the base sequence shown in SEQ ID NO: 35 is obtained by codon optimization of the base sequence shown in SEQ ID NO: 3 encoding the wild type luciferase for mammalian cell expression, which is described below, and further having a mutation to induce three substitutions described above on a corresponding amino acid sequence.

When the mutant luciferase having an amino acid sequence shown in SEQ ID NO: 34 is used, the maximum luminescent wavelength is shifted at a specific pH compared to a case in which the wild type luciferase is used. Specifically, the mutant luciferase catalyzes the light emitting reaction which shows light emission with the maximum luminescent wavelength of 611 nm to 615 nm at any pH condition between pH 7.0 and pH 8.0. On the other hand, the maximum luminescent wavelength obtained from the wild type luciferase is near 605 nm at pH 7.0 condition, near 567 nm at pH 7.5 condition, or near 564 nm at pH 8.0 condition as described below. Therefore, when compared to the wild type, the maximum luminescent wavelength of the light emission obtained from the mutant luciferase is shifted to a longer wavelength side at least in the pH range of pH 7.0 to pH 8.0. Light with long wavelength has better transmission in a living body. Thus, by using such mutant luciferase, light emission can be detected while inhibiting a reduction in luminescence intensity even for a case in which many blocking substances are present between luciferin and a unit for detecting light emission, for example, a case in which a tissue, an embryo, or an individual is tested as a subject.

Further, the mutant luciferase having an amino acid sequence shown in SEQ ID NO: 34 shows different temperature dependency of luminescence intensity from that of the wild type luciferase. Specifically, it shows stronger catalytic activity than the wild type at the temperature higher than room temperature. For example, when the light emitting reaction is allowed to occur at 55° C. for *E. coli* which expresses the mutant luciferase, higher luminescence intensity is obtained than the case of expressing the wild type luciferase.

One example of the mutant luciferase which is derived from *L. accensa* according to the embodiments of the invention is a luciferase having an amino acid sequence shown in SEQ ID NO: 36. The amino acid sequence shown in SEQ ID NO: 36 is an amino acid sequence shown in SEQ ID NO: 1 of the wild type luciferase in which glutamic acid (E) residue at position 322 is substituted with tryptophan (W) residue (E322W). The nucleic acid which encodes the mutant luciferase is a nucleic acid having a base sequence shown in SEQ ID NO: 37 or 39. The base sequence shown in SEQ ID NO: 39 includes a mutation that is introduced to the base sequence shown in SEQ ID NO: 3 encoding the wild type luciferase for having one substitution described above on a corresponding amino acid sequence. Meanwhile, the base sequence shown in SEQ ID NO: 37 is obtained by codon optimization of the base sequence shown in SEQ ID NO: 3 encoding the wild type luciferase for mammalian cell expression, which is described below, and further having a mutation to induce one substitution described above on a corresponding amino acid sequence.

When the mutant luciferase having an amino acid sequence shown in SEQ ID NO: 36 is used, the maximum luminescent wavelength is shifted at a specific pH compared to a case in which the wild type luciferase is used. Specifically, the mutant luciferase catalyzes the light emitting reaction which shows light emission with the maximum luminescent wavelength of 568 nm to 572 nm at any pH condition between pH 6.8 and pH 7.0. On the other hand, the maximum luminescent wavelength obtained from the wild type luciferase is near 612 nm at a pH 6.5 condition or near 605 nm at a pH 7.0 condition as described below. Therefore, when compared to the wild type, the maximum luminescent wavelength of the light emission from the mutant luciferase is shifted to a shorter wavelength side at least in the pH range of pH 6.8 to pH 7.0.

Further, the mutant luciferase having an amino acid sequence shown in SEQ ID NO: 36 shows different temperature dependency of luminescence intensity from that of the wild type luciferase. Specifically, it shows stronger catalytic activity than the wild type at the temperature higher than room temperature. For example, when the light emitting reaction is allowed to occur at 55° C. for *E. coli* which expresses the mutant luciferase, higher luminescence intensity is obtained than the case of expressing the wild type luciferase.

Results obtained from comparison of amino acid sequences of the wild type luciferase (SEQ ID NO: 1), three kinds of the mutant luciferase (SEQ ID NOs: 2, 34 and 36) and a known luciferase derived from *L. biplagiata* (SEQ ID NOs: 30 and 31) are summarized in Table 2.

TABLE 2

Difference in amino acid residues among various luciferases

| | Amino acid residue number having difference | | | | | | | | | | |
|---|---|---|---|---|---|---|---|---|---|---|---|
| | 13 | 50 | 211 | 227 | 249 | 294 | 322 | 323 | 354 | 530 | 542 |
| *L. accensa* (wild type) (SEQ ID NO: 1) | Pro | Asn | Asn | Tyr | Met | Phe | Glu | Val | Glu | Ile | Val |
| *L. accensa* (mutant) (SEQ ID NO: 2) | Pro | Asp | Asn | Tyr | Met | Phe | Glu | Val | Glu | Arg | Val |
| *L. accensa* (mutant) (SEQ ID NO: 34) | Pro | Asn | Asn | Tyr | Met | Tyr | Glu | Leu | Val | Ile | Val |
| *L. accensa* (mutant) (SEQ ID NO: 36) | Pro | Asn | Asn | Tyr | Met | Phe | Trp | Val | Glu | Ile | Val |
| *L. biplagiata* (literature sequence) (SEQ ID NO: 30) | Ala | Asn | Thr | Phe | Lys | Phe | Glu | Val | Glu | Leu | Ala |
| *L. biplagiata* (cloned sequence) | Ala | Asn | Thr | Phe | Met | Phe | Glu | Val | Glu | Leu | Ala |

As indicated in Table 2, when compared to the amino acid sequence of the wild type luciferase, the amino acid sequence of a mutant luciferase having an amino sequence shown in SEQ ID NO: 2 has different amino acids at position 50 and position 530. When compared to the amino acid sequence of the wild type luciferase, the amino acid sequence of a mutant luciferase having an amino sequence shown in SEQ ID NO: 34 has different amino acids at position 294, position 323, and position 354. When compared to the amino acid sequence of the wild type luciferase, the amino acid sequence of a mutant luciferase having an amino sequence shown in SEQ ID NO: 36 has different amino acids at position 322.

Here, the luciferase according to the embodiments of the invention includes those containing mutations in the amino acid sequence (for example, substitution, deletion, addition, and/or the like of amino acids) of the wild type luciferase which is derived from *L. accensa* or the mutant luciferase described above. The luciferase obtained by a mutation is those having a mutation of at least one of amino acid sequence of the wild type luciferase or the mutant luciferase described above, and preferably those having mutations of 1 to 20, 1 to 15, 1 to 10, or 1 to 5 amino acids of the wild type luciferase or the mutant luciferase described above. Preferably, the luciferase obtained by mutation has amino acid sequence homology of 75% or more, 80% or more, 85% or more, 90% or more, 95% or more, 96% or more, 97% or more, 98% or more, or 99% or more with amino acid sequence of the wild type luciferase or the amino acid sequence of the mutant luciferase described above. In particular, it is preferable that the luciferase obtained by the mutation has the same property for light emitting reaction as the wild type luciferase and the mutant *Lucidina accensa* luciferase described above.

One embodiment of the invention relates to a nucleic acid containing the base sequence encoding the luciferase according to the embodiments of the invention. Namely, the nucleic acid is a nucleic acid containing the luciferase gene which is derived from *L. accensa*. In the invention, a nucleic acid indicates, for example, DNA or RNA. In the invention, a "gene" of luciferase means mainly a region transcribed by mRNA, that is, a structural gene. The luciferase encoded by the nucleic acid according to the embodiments of the invention includes both the wild type and the mutant luciferases.

An example of a nucleic acid according to the embodiments of the invention is a nucleic acid containing the base sequence represented by SEQ ID NO: 3. The gene having this sequence is cloned from *L. accensa* and encodes the wild type luciferase. Another example of a nucleic acid according to the embodiments of the invention is a nucleic acid containing the base sequence represented by SEQ ID NO: 32. The gene having this sequence contains a mutation on the base sequence encoding the wild type luciferase cloned from *L. accensa*, and it encodes the mutant luciferase (SEQ ID NO: 2). Another example is a nucleic acid containing the base sequences represented by SEQ ID NOs: 35 and 38. The gene having this sequence contains a mutation on the base sequence encoding the wild type luciferase cloned from *L. accensa*, and it encodes the mutant luciferase (SEQ ID NO: 34). Yet another example is a nucleic acid containing the base sequences represented by SEQ ID NOs: 37 and 39. Each of the genes having those sequences contains a mutation on the base sequence encoding the wild type luciferase cloned from *L. accensa*, and it encodes mutant luciferase (SEQ ID NO: 36).

The nucleic acids according to the embodiments of the invention may be those containing further mutations on the base sequence described above. The mutation on the base sequence includes mutation which does not cause alteration of the amino acid sequence to be encoded. From the nucleic acid introduced with such mutation, a luciferase having the same amino acid sequence as that before the introduction of mutation is expressed. An example of mutation which does not cause alteration of the amino acid sequence is mutation which cancels the recognition sequence of a specific restriction enzyme present in the gene. Because of this mutation, the nucleic acid containing the gene is not digested by the restriction enzyme, but the gene can encode the protein having the same amino acid sequence as that before mutation. Such mutation can be achieved by conversion of the codons constituting the recognition sequence of the restriction enzyme to the synonymous codons with the different base sequence. Such mutation is useful when the recognition sequence of the restriction enzyme to be used for genetic modification is already present in the gene. In this case, fragmentation of the nucleic acid by treatment with a restriction enzyme can be prevented by canceling the recognition sequence of the gene in advance, thereby facilitating genetic modification. An example of such a base sequence in which a recognition sequence for a restriction enzyme is cancelled is that represented by SEQ ID NO: 4. In the sequence, the recognition sequence of EcoRI is cancelled in the base sequence shown in the base sequence 1.

Another example of mutation which does not cause alteration of an amino acid to be encoded is a mutation which optimizes codons of a gene for expression in a specific organism species. Here, the term "optimization" means to substitute codons of a gene contained in a nucleic acid with codons which has high codon frequency in a specific organism species. If the optimization is carried out, expression of a gene in a specific organism species is enhanced in comparison to the case without optimization. The luciferase gene according to the embodiments of the invention is derived from fireflies, and thus as the organism species to which the gene is introduced is farther from fireflies in terms of taxonomy, the higher effects can be obtained by optimization. In the invention, a specific organism species is, for example, a bacterial cell, yeast cell, and mammal cell. A mammal cell is, for example, a mouse cell, a monkey cell, and a human cell. An example of the nucleic acid in which codons are optimized is a nucleic acid containing the base sequence represented by SEQ ID NO: 5. In the nucleic acid, the recognition sequences of BamHI and EcoRI are cancelled and codons are optimized for expression in a mammal cell.

The nucleic acid according to the embodiments of the invention contains those containing the base sequence of a luciferase gene provided with Kozak sequence. Kozak sequence is a sequence having an initiation codon and plural base sequences located in before and after the initiation codon. It has been proved that expression amount of the gene is increased because of the presence of Kozak sequence. With respect to Kozak sequence, a common sequence has been found in each organism species or biome. The nucleic acid containing Kozak sequence according to the embodiments of the invention has a Kozak sequence corresponding to the organism species to which it is introduced. For example, in the case where it is introduced into a mammal cell, the nucleic acid contains the sequence gccrccatgg as Kozak sequence, in which r means guanine or adenine. Luciferase gene provided with Kozak sequence may be a wild type gene or a mutant gene in which codons are optimized in such a manner described above.

One embodiment according to the invention includes a vector having these nucleic acids. The vector may contain a nucleic acid and the like containing a sequence for regulating expression or sequence of a marker gene other than the nucleic acid encoding luciferase.

One embodiment according to the invention relates to a method for analyzing function in a cell by utilizing the luciferase according to the embodiments of the invention. The method includes introducing the luciferase according to the embodiments of the invention into a cell and detecting luminescence of the luciferase with an imaging apparatus. For example, the luciferase gene according to the embodiments of the invention is introduced in downstream of a specific expression regulation region in DNA, and the expression of luciferase is detected based on the presence or absence of luminescence, thereby achieving the determination of the function of the expression regulation region.

One embodiment according to the invention relates to a method for analyzing an intracellular protein by utilizing the luciferase according to the embodiments of the invention. The method includes introducing a fusion protein having the luciferase according to the embodiments of the invention and a protein to be analyzed; and detecting luminescence of the luciferase with an imaging apparatus.

The method includes observation of localization of the protein to be analyzed in a cell and time-course observation (time-lapse) of the localization. The method includes the identification of not only the protein localization but also mere confirmation whether the protein is expressed or not. Cells to be used are not specially limited, and may be those which can be ordinarily used in a field of cell imaging. Further, the proteins to be analyzed are also not specially limited, and they can be selected in accordance with the aim of research. The protein may be those which essentially exist in a cell to be used, or may be heterogeneous or modified proteins which do not essentially exist in a cell.

For introducing a fusion protein into a cell, known methods for introducing can be applied. One of them is a method for directly introducing a fusion protein purified in vitro into a cell. For example, a fusion protein can be directly injected into a cell by a microinjection method. Alternatively, a cell is incubated in culture medium containing a fusion protein, thereby introducing the fusion protein into a cell by endocytosis. Another method is to introduce a nucleic acid containing the base sequence encoding the fusion protein, followed by expression of the fusion protein in a cell. For example, an expression vector containing the nucleic acid is introduced into a cell by a calcium phosphate method, lipofection, electroporation, and the like, thereby achieving expression of the fusion protein from the expression vector. Here, the gene of a fusion protein is those containing the luciferase gene according to the embodiments of the invention and the gene of the protein to be analyzed, in which the luciferase gene and the gene of the protein are linked so that each of them can be normally translated.

For detection of luminescence of luciferase with an imaging apparatus, well known detection methods can be applied. For example, a luciferase luminescent reaction is caused by adding luciferin, ATP, $Mg^{2+}$ ions, and the like to a cell expressing a fusion protein containing luciferase as appropriate, and the emitted luminescence can be detected by an imaging apparatus. The imaging apparatus is a microscope provided with a filter for capturing luminescence. The localization of a protein can be specified by using a microscope based on the information obtained through identification of position of luminescence in a cell. As an imaging apparatus, a microscope provided with function which enables time-course image pickup can be used, and time-course observation can be achieved by using the microscope.

EXAMPLES

Example 1

Cloning of Luciferase Gene Derived from *Lucidina accensa*

1. Materials

Firefly larvae of *Lucidina accensa* collected in Tokyo metropolitan were used as materials.

2. Extraction of Total RNA and Synthesis of cDNA

A luminescent organ was cut off from firefly larvae using scissors. To Lysing Matrix D tube (manufactured by MP-Biomedicals, LLP), which is a tube containing beads for homogenizing tissues and cells, added were the collected luminescent organ and 1 mL of total RNA extraction reagent TRIzol Reagent (manufactured by Invitrogen). The tube was installed in a homogenization system FastPrep 24 (manufactured by MP-Biomedicals, LLP) or FastPrep FP100A (manufactured by MP-Biomedicals Co., Ltd.), and the firefly luminescent organ was homogenized in the reagent at vibration speed of 6.5 m/s and vibration time of 45 seconds. Upon completion thereof, the tube was taken out from the system and placed on ice for 30 minutes. Consequently, the homogenizing process was repeated once more under the same condition.

In the next step, according to the instructions of total RNA extraction reagent TRIzol Reagent, total RNA was isolated and purified from the homogenized solution. 100 μL of the obtained mRNA solution was precipitated and concentrated by an ethanol precipitation method. A full length cDNA was synthesized from the precipitated and concentrated total RNA with use of a full length cDNA synthesis reagent GeneRacer (manufactured by Invitrogen) according to the manual. 20 μL of the obtained cDNA solution was subjected to the genetic experiments described below as a firefly full length cDNA library.

3. Identification of 5' Terminal Side of Luciferase Gene 3-1. Preparation of Primers to be Used for Rapid Amplification of cDNA End (RACE) Method Cloning of a luciferase gene was performed by a polymerase chain reaction (PCR) method. The primers used for the PCR were prepared as described below based on the amino acid sequence of luciferase gene derived from a known closely-related species.

In order to confirm the amino acid region which is highly conserved in luciferases derived from fireflies, amino acid sequences of 10 types of luciferase derived from fireflies which have been already published are compared to one another with use of sequence information analysis software DNASIS Pro (manufactured by Hitachi Software Engineering Co., Ltd.). The closely-related species used for the comparison is *Lampyris noctiluca* (Registration No. CAA61668), *Luciola cruciata* (Registration No. P13129), *Luciola lateralis* (Registration No. Q00158), *Luciola mingrelica* (Registration No. Q26304), *Hotaria parvula* (Registration No. AAC37253), *Photinus pyralis* (Registration No. BAF48390), *Photuris pennsylvanica* (Registration No. Q27757), *Pyrocoelia miyako* (Registration No. AAC37254), *Pyrocoelia rufa* (Registration No. AAG45439), and *Rhagophthalmus ohbai* (Registration No. BAF34360).

Consequently, it was proved that amino acid sequence L-I-K-Y-K-G-Y-Q-V (SEQ ID NO: 6) located in the proximity of 440th residue on C terminal side of luciferase is highly conserved. Based on the codons encoding these 9 amino acids, the base sequence was predicted, and 12 types of luciferase specific mixed primers were designed to be applied to 5' terminal RACE PCR. The names and sequences of these primers are as follows (Y, R, and N in the primer sequences indicate mixed bases): flexLuc5-ATA (5'-ACY TGR TAN CCY TTA TAT TTA AT-3': SEQ ID NO: 7), flexLuc5-ATG (5'-ACY TGR TAN CCY TTA TAT TTG AT-3': SEQ ID NO: 8), flexLuc5-ATT (5'-ACY TGR TAN CCY TTA TAT TTT AT-3': SEQ ID NO: 9), flexLuc5-ACA (5'-ACY TGR TAN CCY TTA TAC TTA AT-3': SEQ ID NO: 10), flexLuc5-ACG (5'-ACY TGR TAN CCY TTA TAC TTG AT-3': SEQ ID NO: 11), flexLuc5-ACT (5'-ACY TGR TAN CCY TTA TAC TTT AT-3': SEQ ID NO: 12), flexLuc5-GTA (5'-ACY TGR TAN CCY TTG TAT TTA AT-3': SEQ ID NO: 13), flexLuc5-GTG (5'-ACY TGR TAN CCY TTG TAT TTG AT-3': SEQ ID NO: 14), flexLuc5-GTT (5'-ACY TGR TAN CCY TTG TAT TTT AT-3': SEQ ID NO: 15), flexLuc5-GCA (5'-ACY TGR TAN CCY TTG TAC TTA AT-3': SEQ ID NO: 16), flexLuc5-GCG (5'-ACY TGR TAN CCY TTG TAC TTG AT-3': SEQ ID NO: 17), flexLuc5-GCT (5'-ACY TGR TAN CCY TTG TAC TTT AT-3': SEQ ID NO: 18). The synthesis of these primers was outsourced to Life Technologies, Japan, Co., Ltd.

3-2. Cloning of 5' Terminal Side of Luciferase Gene by 5'-RACE PCR

With use of the firefly full-length cDNA library which was prepared in such a manner described above as a template, 5'-RACE RCP was performed using 12 types of specific mixed primers and 5' terminal specific primer prepared in such a manner described above; GeneRacer 5' Primer (5'-CGA CTG GAG CAC GAG GAC ACT GA-3': SEQ ID NO: 19) and GeneRacer 5' Nested Primer (5'-GGA CAC TGA CAT GGA CTG AAG GAG TA-3': SEQ ID NO: 20). GeneRacer 5' Primer and GeneRacer 5' Nested Primer were those contained in a full length cDNA synthesis reagent GeneRacer kit (manufactured by Invitrogen). In order to amplify the luciferase gene efficiently by 5'-RACE PCR, with use of the gene amplified once by PCR as a template, nested PCR which amplifies the gene further specifically with an inside primer pair was performed. The PCR was carried out with use of polymerase Ex-Taq (manufactured by Takara Bio Inc.) according to the manual.

As the first PCR, the luciferase gene was amplified with use of 12 types of primer pairs composed of any one of the aforementioned 12 types of specific mixed primer and GeneRacer 5' Primer. 10 μL of PCR reaction solution comprising 10× Ex Tag Buffer (20 mM $Mg^{2+}$ plus) at a final concentration with the same ratio, dNTP mixture at a final concentration of 0.2 mM (2.5 mM each), TaKaRa Ex Taq (5 U/μL) at a final concentration of 0.05 U/μL, one of 12 types of primers at a final concentration of 1.0 μM, and GeneRacer 3' Primer at a final concentration of 0.3 μM was prepared and 0.2 μL of firefly full-length cDNA library solution was added thereto. Here, the concentration of the firefly full-length cDNA library solution was not determined. In the PCR reaction, the solution was thermally denatured for 2 minutes at 94° C., and then the cycle consisting of 30 seconds at 94° C., 30 seconds at 45° C., and 90 seconds at 72° C. was repeated 30 times, followed by an elongation reaction at 72° C. for 5 minutes. After the PCR reaction, 1 μL of the PCR reaction solution was applied to electrophoresis with use of 1% tris acetic acid buffer (TAE) agarose gel, and observed the bands of amplified genes under exposure of ultraviolet after dyeing with ethidium bromide. In all of the 12 reaction solution, a slight gene amplification was confirmed, and thus a nested PCR reaction was carried out with use of each PCR reaction solution as a template, in such a manner described below.

As nested PCR, amplification of luciferase gene was carried out with use of four kinds of primer pairs each having four types out of 12 types of primers used in the first PCR and GeneRacer 3' Nested Primer. 10 μL of PCR reaction solution comprising 10× Ex Tag Buffer (20 mM $Mg^{2+}$ plus) at a final concentration with the same ratio, dNTP mixture at a final concentration of 0.2 mM (2.5 mM each), TaKaRa Ex Tag (5 U/μL) at a final concentration of 0.005 U/μL, one of 12 types of primers at a final concentration of 1.0 μM, and GeneRacer 3'Primer at a final concentration of 0.3 μM was prepared and 1.0 μL of the first PCR reaction solution diluted ten fold with sterilized water was added thereto as a template. In the PCR reaction, the solution was thermally denatured for 2 minutes at 94° C., and then the cycle consisting of 30 seconds at 94° C., 30 seconds at 45° C., and 90 seconds at 72° C. was repeated 30 times, followed by an elongation reaction at 72° C. for 5 minutes. After the PCR reaction, 1 μL of PCR reaction solution was applied to electrophoresis with use of 1% TAE agarose gel, and observed the bands of amplified genes under exposure of ultraviolet after dyeing with ethidium bromide. The combination condition of primers which efficiently amplified the gene in the proximity of about 1.4 kbp was confirmed.

3-3. Determination of Base Sequence of Gene Amplified by 5'-RACE

In order to determine the base sequence of the gene amplified by 5'-RACE, purification by gel extraction, subcloning, and direct sequencing of a PCR product were carried out. The details are given below.

The PCR was carried out with use of the combination which efficiently amplified the gene in the proximity of about 1.4 kbp (final volume 20 μL), and then the objective gene fragments were collected with use of gel extraction. Gel extraction was carried out with use of Wizard SV Gel and PCR Clean-UP System (manufactured by Promega KK) according to the manual thereof. Subcloning of the PCR products extracted from gel were carried out by a method of TA cloning. TA cloning was carried out with use of pGEM-T Easy Vector System (manufactured by Promega KK) according to the manual thereof. Subsequently, the vector DNA was transformed to *Escherichia coli* (TOP10 strain or DH5α strain), and insert positive colonies were selected by a method of blue-white screening. The selected colonies were subjected to a direct colony PCR, and confirmed that the objective gene was inserted. In a direct colony PCR, a primer pair including M13-F(-29) Primer (5'-CAC GAC GTT GTA AAA CGA C-3': SEQ ID NO: 21) and M13 Reverse (5'-GGA TAA CAA TTT CAC AGG-3': SEQ ID NO: 22) was used. 10 μL of PCR reaction solution comprising 10× Ex Taq Buffer (20 mM $Mg^{2+}$ plus) at a final concentration with the same ratio, dNTP mixture at a final concentration of 0.2 mM (2.5 mM each), TaKaRa Ex Taq (5 U/μL) at a final concentration of 0.05 U/μL, and a primer pair at a final concentration of 0.2 μM was prepared and a small amount of colony of *Escherichia coli* was added thereto as a template. In the PCR reaction, the solution was thermally denatured for 1 minute at 94° C., and then the cycle consisting of 30 seconds at 94° C., 30 seconds at 50° C., and 2 minutes at 72° C. was repeated 25 times, followed by an elongation reaction at 72° C. for 2 minutes. After the PCR reaction, 2 μL of PCR reaction solution was applied to electrophoresis with use of 1% TAE agarose gel, and observed the bands of amplified genes under exposure of ultraviolet after dyeing with ethidium bromide.

With regard to the PCR reaction solution for which amplification was confirmed, the base sequence of the gene was determined by a direct sequencing method. With use of PCR product purification kit ExoSAP-IT (manufactured by GE Healthcare Bioscience), the extra dNTP and primers contained in the PCR reaction solution were removed, and a template for the PCR direct sequencing was prepared. With use of BigDye Terminator v3.1 Cycle Sequencing Kit (manufactured by Applied Biosystems), a sequencing reaction solution containing the template was prepared, and a sequencing reaction was performed by a thermal cycler. Purification and sequencing of the PCR products were each carried out according to the manuals thereof. After the sequencing reaction, the reaction products were purified as described below. 2.5 times of weight of 100% ethanol was added to the reaction solution, and then a nucleic acid was precipitated by a centrifuge. After the supernatant was removed, 70% ethanol was added to wash the precipitates, and the nucleic acids were precipitated by a centrifuge. Finally, the supernatant was removed and the precipitate was dried. To the purified precipitate, 15 μL of Hi-Di Formamide (manufactured by Applied Biosystems) was added and dissolved. The solution was subjected to thermal denaturation at 94° C. for 2 minutes, and then rapidly cooled on ice, thereby providing a sample for determination of base sequence. With respect to the sample, the base sequence was determined by using Applied Biosystems 3130 xl genetic analyzer (manufactured by Applied Biosystems). The analytical method was carried out according to the manual.

The obtained gene sequence (SEQ ID NO: 23) by sequencing was analyzed by the "sequence linking" function of sequence information analysis software DNASIS Pro. With respect to the sequence, homology research was performed by using blastx search provided by the National Center for Biotechnology Information (herein below, abbreviated as "NCBI"), and it was confirmed that the sequence has a high homology with base sequences of known luciferases. The base sequence obtained by the aforementioned experiments and analyses was determined as being located on 5' terminal side of a novel luciferase gene.

4. 3' Race RCR of Luciferase Gene and Acquisition of Full-Length cDNA 4-1. Design of Primers to be Used for 3' Race PCR Based on the sequence in the non-translated region on 5' terminal side of luciferase gene obtained by the 5' Race PCR experiment, primers to be used for 3' RACE and those used for Nested PCR were prepared. Synthesis of primers was outsourced to Life Technologies, Japan.

4-2. 3' Race PCR for Acquisition of Full-Length cDNA of Luciferase Gene

With use of the firefly full-length cDNA library prepared as described above as a template, 3'-RACE PCR was performed by applying the primer prepared from the base sequence of the non-translated region on 5' terminal side of objective firefly luciferase (name: JP-Ohoba-Full-F1,5'-GAT TCG AGA TAG TGC TAG TC-3': SEQ ID NO: 24), GeneRacer 3' Primer (5'-GCT GTC AAC GAT ACG CTA CGT AAC G-3'; SEQ ID NO: 25), and GeneRacer 3'Nested Primer (5'-CGC TAC GTA ACG GCA TGA CAG TG-3': SEQ ID NO: 26). The used GeneRacer 3' Primer and GeneRacer 3' Nested Primer were contained in a full-length cDNA synthesis reagent GeneRacer kit (manufactured by Invitrogen). In order to efficiently amplify luciferase gene by 3'-RACE PCR, the genes once amplified by PCR were used as a template, and the nested PCR which further specifically amplifies the gene was carried out with use of the inside primer pair. The PCR was carried out with use of polymerase Ex-Taq (manufactured by Takara Bio Inc.) according to the manual.

As the first PCR, a primer pair composed of a primer prepared from base sequence of the non-translated region on 5' terminal side and GeneRacer 3'Primer was used to amplify the luciferase gene. 20 μL of PCR reaction solution comprising 10× Ex Taq Buffer (20 mM $Mg^{2+}$ plus) at a final concentration with the same ratio, dNTP mixture at a final concentration of 0.2 mM (2.5 mM each), TaKaRa Ex Taq (5 U/μL) at a final concentration of 0.05 U/μL, and primers at a final concentration of 0.3 μM was prepared and 0.4 μL of firefly full-length cDNA library solution was added thereto. Here, the concentration of the firefly full-length cDNA library solution was not determined. In the PCR reaction, the solution was thermally denatured for 2 minutes at 94° C., and then the cycle consisting of 30 seconds at 94° C., 30 seconds at 50° C., and 2 minutes at 72° C. was repeated 30 times, followed by an elongation reaction at 72° C. for 5 minutes. After the PCR reaction, 1 μL of the PCR reaction solution was applied to electrophoresis with use of 1% TAE agarose gel, and observed the bands of amplified genes under exposure of ultraviolet after dyeing with ethidium bromide. Slight gene amplification was confirmed, and thus nested PCR reaction was performed with use of the PCR reaction solution as a template.

As the Nested PCR, the luciferase gene was amplified with use of a primer pair including a primer for Nested PCR (name:

JP-Ohoba-Full-F2,5'-GAT TCG AGA TAG TGC TAG TCA AAA GC-3'; SEQ ID NO: 27) and GeneRacer 3' Nested Primer. 20 μL of Nested PCR reaction solution comprising 10× Ex Taq Buffer (20 mM $Mg^{2+}$ plus) at a final concentration with the same ratio, dNTP mixture at a final concentration of 0.2 mM (2.5 mM each), TaKaRa Ex Taq (5 U/μL) at a final concentration of 0.05 U/μL, and primers at a final concentration of 0.3 μM was prepared and 1.0 μl of a solution prepared by diluting the first PCR reaction solution in tenfold with sterilized water was added thereto as a template. In the PCR reaction, the solution was thermally denatured for 2 minutes at 94° C., and then the cycle consisting of 30 seconds at 94° C., 30 seconds at 50° C., and 2 minutes at 72° C. was repeated 30 times, followed by an elongation reaction at 72° C. for 5 minutes. After the PCR reaction, 1 μL of PCR reaction solution was applied to electrophoresis with use of 1% TAE agarose gel, and observed the bands of amplified genes under exposure of ultraviolet after dyeing with ethidium bromide. It was confirmed that the gene was efficiently amplified at about 2 kbp.

4-3. Determination of Base Sequence of the Gene Amplified by 3'-Race

In order to identify the base sequence amplified by 3'-RACE, PCR product was purified by gel extraction, followed by subcloning and direct sequencing. The details are given below.

With the combination of primers which efficiently amplified the genes at about 2 kbp, PCR (final volume 20 μL) was carried out, and the objective gene fragments were collected by means of gel extraction. The gel extraction was carried out with use of Wizard SV Gel and PCR Clean-Up System (manufactured by Promega KK) according to the manual. The subcloning of the PCR product extracted from gel was carried out by means of TA cloning. The TA cloning was performed with use of pGEM-T Easy Vector System (manufactured by Promega KK) according to the manual. Subsequently, the vector DNA was transformed to E. coli (TOP10 strain or DH5α strain), and the insert positive colonies were selected by means of blue-white screening. The selected colonies were subjected to a direct colony PCR, and confirmed that the gene was introduced. In the direct colony PCR, a primer pair including M13-F(-29) Primer and M13 Reverse was used. 10 μL of PCR reaction solution comprising 10× Ex Taq Buffer (20 mM $Mg^{2+}$ plus) at a final concentration with the same ratio, dNTP mixture at a final concentration of 0.2 mM (2.5 mM each), TaKaRa Ex Taq (5 U/μL) at a final concentration of 0.05 U/μL, and primers at a final concentration of 0.2 μM was prepared and a small amount of E. coli colony was added thereto as a template. In the PCR reaction, the solution was thermally denatured for 1 minute at 94° C., and then the cycle consisting of 30 seconds at 94° C., 30 seconds at 50° C., and 2 minutes at 72° C. was repeated 25 times, followed by an elongation reaction at 72° C. for 2 minutes. After the PCR reaction, 2 μl of the PCR reaction solution was applied to electrophoresis with use of 1% TAE agarose gel, and observed the bands of amplified genes under exposure of ultraviolet after dyeing with ethidium bromide.

As for the PCR reaction solutions for which the amplification was confirmed, the base sequence of the gene was determined by a direct sequencing method. With use of a PCR product purification kit ExoSAP-IT (manufactured by GE Healthcare Bioscience), extra dNTP and primers contained in the PCR reaction solution were removed, and prepared a template for PCR direct sequencing. A sequencing reaction solution containing the template was prepared with use of BigDye Terminator v3.1 Cycle Sequencing Kit (manufactured by Applied Biosystems), and the sequencing reaction was carried out by a thermal cycler. The primers used for sequencing were a vector primer or a primer specific to a gene. Purification of the PCR products and sequencing were each performed according to the manual. After the sequencing reaction, the purification was performed as follows. To the reaction solution, added was 2.5 times by weight of 100% ethanol, followed by precipitation of the nucleic acid by a centrifuge. After removing the supernatant, the precipitate was washed by adding 70% ethanol and the nucleic acid were precipitated by a centrifuge. After removing the supernatant, the precipitate was dried finally. To the purified precipitate, 15 μL of Hi-Di Formamide (manufactured by Applied Biosystems) was added and dissolved. The solution was thermally denatured at 94° C. for 2 minutes, rapidly cooled on ice, and used as a sample for determination of base sequence. With respect to the sample, the base sequence was determined with use of Applied Biosystems 3130 xl genetic analyzer (manufactured by Applied Biosystems). The analytical method of the base sequence was carried out according to the manual.

A full-length firefly luciferase gene was obtained by sequencing. As for the base sequence (SEQ ID NO: 3) or the sequence translated into the amino acid (SEQ ID NO: 1), the homology search was performed by utilizing the blastx or blastp search provided by NCBI. In each search, it was confirmed that the base sequence has high homology with the base sequences of known luciferases. The base sequence obtained in the experiments and analysis described above was determined as a full-length cDNA sequence of a novel luciferase. Herein after, the base sequence and amino acid sequence are described.

Base sequence:

(SEQ ID NO: 3)
ATGGAAGAGGATAAAAATATTCTGCGCGGCCCAGCGCCATTCTATCCTTT

AGAAGATGGAACTGCAGGCGAACAATTACATAGAGCGATGAAAAGATATG

CCTTAATTCCAGGAACCATCGCTTTCACGGACGCTCATGCGGGAGTAAAT

ATCACGTACTCCGAATATTTCGAAATGGCATGCCGATTAGCTGAAAGTTT

GAAAAGATACGGACTTGGATTACAGCACAGAATTGTTGTGTGTAGTGAAA

ATTCTCTACAATTTTTTATGCCCGTCGTGGGTGCCCTATTTATTGGAGTG

GGGGTCGCACCAGCAAATGATATTTATAACGAGCGTGAATTACTCAATAG

CATGACCATATCGCAGCCCACCTTAGTCTTCTGCTCCAGAAAAGGATTGC

AAAAAATTTTGAACGTACAGAAAAAATTACCAGTAATTCAAAAAATTATT

ATTCTGGATACTAAAGAGGATTATATGGGATTTCAGTCAATGTACTCATT

TGTTGACTCGCAATTACCAGTAGGTTTCAACGAATATGATTATGTACCGG

ACTCCTTCGACCGCGATCAAGCAACGGCACTTATAATGAACTCCTCTGGA

TCTACTGGGTTGCCGAAAGGGGTGGAGCTTAACCACACGAGTGTTTGTGT

CAGATTTTCGCATTGCAGAGATCCTGTTTATGGGAATCAAATTATTCCCG

ATACTGCAATTTTAAGTGTTATCCCATTCCATCATGGATTTGGGATGTTT

ACAACGCTAGGATATTTAATATGTGGATTTCGAGTTGTGCTGATGTATAG

ATTTGAAGAAGAACTATTTTTGCGATCCCTTCAAGATTATAAAATTCAGA

GTGCGTTACTAGTACCCACCCTATTTTCGTTCTTTGCGAAAAGCACTCTA

ATTGACAAGTACGATTTATCCAATTTACATGAAATTGCGTCTGGTGGTGC

TCCCCTCGCAAAAGAAGTTGGAGAAGCAGTGGCAAAACGCTTTAACCTTC

-continued
```
GAGGTATACGGCAAGGGTACGGCTTGACCGAAACTACATCGGCCGTTATT

ATTACACCTGAGGGAGATGATAAGCCAGGTGCAGTCGGTAAGGTTGTACC

CTTCTTTTCGGCAAAAGTTGTTGATCTCGACACCGGGAAAACTTTGGGAG

TTAATCAAAGGGGCGAATTGTGTCTGAAAGGCCCCATGATTATGAAAGGT

TATGTAAATAACCCTGAAGCTACAAATGCCTTGATCGATAAAGATGGATG

GCTACACTCTGGTGATATATCATACTGGGACGAAGACGGTCACTTCTTCA

TTGTTGATCGCTTGAAATCTTTGATTAAATATAAAGGGTACCAGGTACCG

CCCGCTGAATTGGAATCCATTTTGCTGCAACATCCCTTTATCTTCGATGC

AGGGGTGGCTGGAATTCCCGACGATGAAGCCGGTGAATTGCCCGCTGCCG

TTGTTGTTTTAGAGGAAGGAAAAACTATGACTGAAAAAGAAATCATGGAT

TATGTGGCAGGTCAGGTAACTACAGCAAAACGGCTACGTGGAGGTGTCGT

ATTCGTCGATGAAGTGCCGAAGGGTCTCACTGGGAAAATCGATGCACGAA

AAATTAGAGAAATACTTGTGAAAGTAAAGAAAACCAAATCAAAATTGTA

A.
```

Amino acid sequence:

```
                                              (SEQ ID NO: 1)
MEEDKNILRGPAPFYPLEDGTAGEQLHRAMKRYALIPGTIAFTDAHAGVN

ITYSEYFEMACRLAESLKRYGLGLQHRIVVCSENSLQFFMPVVGALFIGV

GVAPANDIYNERELLNSMTISQPTLVFCSRKGLQKILNVQKKLPVIQKII

ILDTKEDYMGFQSMYSFVDSQLPVGFNEYDYVPDSFDRDQATALIMNSSG

STGLPKGVELNHTSVCVRFSHCRDPVYGNQIIPDTAILSVIPFHHGFGMF

TTLGYLICGFRVVLMYRFEEELFLRSLQDYKIQSALLVPTLFSFFAKSTL

IDKYDLSNLHEIASGGAPLAKEVGEAVAKRFNLRGIRQGYGLTETTSAVI

ITPEGDDKPGAVGKVVPFFSAKVVDLDTGKTLGVNQRGELCLKGPMIMKG

YVNNPEATNALIDKDGWLHSGDISYWDEDGHFFIVDRLKSLIKYKGYQVP

PAELESILLQHPFIFDAGVAGIPDDEAGELPAAVVVLEEGKTMTEKEIMD

YVAGQVTTAKRLRGGVVFVDEVPKGLTGKIDARKIREILVKVKKTKSK

L*.
```

Herein after, the novel luciferase is referred to as the wild type luciferase derived from *L. accensa*.

Example 2

Determination of Enzymatic Parameters of Wild Type Luciferase

1. Protein Expression of Wild Type Luciferase Gene

For expressing the wild type luciferase gene in *E. coli*, it was introduced into a pRSET-B vector (manufactured by Invitrogen). According to the standard method, the gene expression vector was constructed by experiments described below.

1-1. Modification of Recognition Site of Restriction Enzyme of Wild Type Luciferase Gene According to the base sequence determined as described above, the wild type luciferase gene contains the recognition sequence of restriction enzyme EcoRI. The genetic modification was carried out so that the amino acid sequence of luciferase was maintained and the recognition sequence in these base sequences were removed. This treatment was carried out for the purpose of facilitating the introduction of luciferase gene into an expression vector which is described below. The introduction of genetic mutation was carried out by following the method described in "An experimental method of gene functional inhibition-from simple and secure gene function analysis to application to gene therapy" edited by Kazunari Taira (Yodosha, published in 2001, pages 17 to 25). The base sequence after mutation introduction is represented by SEQ ID NO: 4.

1-2. Introduction of Wild Type Luciferase Gene into Vector for Gene Expression

In order to introduce the wild type luciferase gene to a restriction enzyme region between BamHI site and EcoRI site of pRSET-B vector, a primer comprising initiation codon and recognition sequence of restriction enzyme BamHI GGATCC therebefore, and a primer comprising termination codon and recognition sequence of restriction enzyme EcoRI GAATTC thereafter were prepared. With use of the primer pair, a fragment containing the aforementioned restriction enzyme recognition sites on both terminals of luciferase gene was amplified. The PCR was carried out with use of polymerase KOD-Plus (manufactured by Toyobo Co., Ltd.) according to the manual.

20 μl of PCR reaction solution comprising 10×PCR Buffer at a final concentration with the same ratio, dNTP mixture at a final concentration of 0.2 mM (2.5 mM each), $MgSO_4$ at a final concentration of 1.0 mM, Toyobo KOD-Plus (1 U/μL) at a final concentration of 0.02 U/μL, and a primer pair at a final concentration of 0.3 μM was prepared and 0.4 μL of luciferase gene not containing BamHI and EcoRI recognition sequences was added thereto as a template. In the PCR reaction, the solution was thermally denatured for 2 minutes at 94° C., and then the cycle consisting of 30 seconds at 94° C., 30 seconds at 55° C., and 2 minutes at 68° C. was repeated 30 times, followed by elongation reaction at 68° C. for 5 minutes. After the PCR reaction, 1 μl of PCR reaction solution was applied to electrophoresis with use of 1% TAE agarose gel, and observed the bands of amplified genes under exposure of ultraviolet after dyeing with ethidium bromide. The gene amplification was confirmed, and thus this PCR reaction solution was precipitated and concentrated by an ethanol precipitation method, dissolved by adding 4 μL of 10×H Buffer for restriction enzyme treatment, restriction enzyme BamHI (manufactured by Toyobo Co., Ltd.) and restriction enzyme EcoRI (manufactured by Toyobo Co., Ltd.) of 2 μL each, and 32 μl of sterile deionized ion water, and treated with the restriction enzymes while maintaining the temperature at 37° C. for 2 hours. Subsequently, the reaction solution was precipitated and concentrated by an ethanol precipitation method, and dissolved in sterile deionized ion water. The solution was applied to electrophoresis with use of 1% TAE agarose gel, followed by dyeing with ethidium bromide. The gel containing DNA bands which were confirmed under exposure of ultraviolet were cut out with a knife. From the obtained gel, DNA was extracted with use of Wizard (R) SV Gel and PCR Clean-UP System (manufactured by Promega KK). These operations were performed according to the manual. Subsequently, with use of Ligation Pack (manufactured by Nippon Gene) in accordance with the manual, the extracted DNA was introduced into pRSET-B vector which was treated by the restriction enzymes BamHI and EcoRI in advance by a similar method. This vector DNA was transformed to *E. coli* JM109 (DE3) strain and allowed colony formation.

Direct colony PCR was carried out using the obtained colony as a template, and the luciferase gene introduced into pRSET-B was amplified. The direct colony PCR was performed with use of a primer pair of T7 promoter Primer (5'-TAA TAC GAC TCA CTA TAG GG-3': SEQ ID NO: 28) and T7 Reverse Primer (5'-CTA GTT ATT GCT CAG CGG TGG-3': SEQ ID NO: 29). 10 μL of PCR reaction solution comprising 10× Ex Taq Buffer (20 mM $Mg^{2+}$ plus) at a final concentration with the same ratio, dNTP mixture at a final concentration of 0.2 mM (2.5 mM each), TaKaRa Ex Taq (5 U/μL) at a final concentration of 0.05 U/μL, and primers at a final concentration of 0.2 μM was prepared and a small amount of E. coli colony was added thereto as a template. In the PCR reaction, the solution was thermally denatured for 2 minutes at 94° C., and then the cycle consisting of 30 seconds at 94° C., 30 seconds at 50° C., and 2 minutes at 72° C. was repeated 25 times, followed by an elongation reaction at 72° C. for 5 minutes. After the PCR reaction, 1 μL of PCR reaction solution was applied to electrophoresis with use of 1% TAE agarose gel, and observed the bands of amplified genes under exposure of ultraviolet after dyeing with ethidium bromide.

As for the PCR reaction solution for which amplification was confirmed, the base sequence of the gene was determined by a direct sequencing method. With use of PCR product purification kit ExoSAP-IT, the extra dNTP and primers contained in the PCR reaction solution were removed, thereby preparing a template for PCR direct sequencing. The sequencing reaction solution containing the template was prepared by using BigDye Terminator v3.1 Cycle Sequencing Kit, and sequencing reaction was carried out with use of a thermal cycler. A vector primer or a primer specific to the gene was used for sequencing. Purification and sequencing of PCR product were carried out according to the manual. After sequencing reaction, the reaction product was purified as described below. 2.5 times by weight of 100% ethanol was added to the reaction solution, and the nucleic acid was precipitated by a centrifuge. After removing the supernatant, the precipitate was washed by adding 70% ethanol and the nucleic acid was precipitated by a centrifuge. After removing the supernatant, the precipitation was finally dried. The purified precipitate was dissolved by adding 15 μL of Hi-Di Formamide (manufactured by Applied Biosystems). The solution was thermally denatured for 2 minutes at 94° C., rapidly cooled on ice, and used as a sample for determination of the base sequence. With respect to the sample, the base sequence was determined by Applied Biosystems 3130 xl Genetic Analyzer, and confirmed that the gene was introduced into a gene expression vector pRSET-B.

2. Purification of a Luminescent Protein 0.5 μL of luciferase vector was added to 50 μL of the E. coli solution containing JM109 (DE3), and the solution was incubated on ice for 10 minutes, then at 42° C. for 1 minute, and finally incubated on ice for 2 minutes. Subsequently, 50 μL of the E. coli solution was added to 200 μL of SOC culture medium, and the mixture solution of E. coli and SOC medium was incubated while shaking for 20 minutes at 37° C. 100 μL of the incubated sample was streaked on a LB culture medium plate (containing 100 μg/mL of Ampicillin) and incubated at 37° C. overnight. On the next day, the obtained colony was picked up and incubated in LB culture medium of 500 mL scale at 37° C. for 24 hours and at 18° C. for 24 hours. After the incubation of 48 hours, the cell body was collected by a centrifuge, resuspended in 0.1 M Tris-HCl solution (pH 8.0), and subjected to be ultrasonic fragmentation. The fragmented solution of the cell body was subjected to centrifuge separation (15,000 rpm, 10 minutes), and the supernatant was collected by removing the precipitate. To the column having 2 mL of a bed volume, 500 μL of Ni-Agar suspension solution and 2 mL of 0.1 M Tris-HCl were added to equilibrate the column. The collected supernatant was added to the column, and let it pass through the column. While all the supernatant was passed through the column, the operations were all carried out at 4° C. The column was washed with 2 mL of 25 mM imidazole/0.1 M Tris-HCl solution. To the washed column, 2 mL of 500 mM imidazole/0.1 M Tris-HCl solution was added to elute luciferase. The eluted sample was filtered through gel filtration column PD-10 (manufactured by GE Healthcare) and demineralized. The demineralized sample was subjected to ultrafiltration with Vivaspin6 (manufactured by Sartorius K.K.), and glycerin was added to the concentrated sample to prepare 50% glycerine solution. The solution was conserved at −20° C.

3. Measurement of Light Emission Spectra

With use of LumiFlSpectroCapture (manufactured by ATTO Corporation) as an apparatus for measurement, to a solution of 0.1 M citric acid/0.1 M $Na_2HPO_4$ buffer (pH 5.5 to 8.0) containing 1 mM of D-luciferin, 2 mM of ATP and 4 mM of $MgCl_2$ the purified enzyme was added at a final concentration of 1 μg/mL, and after 15 seconds of addition of the enzyme luminescence spectra was measured. The measurement results were illustrated in FIG. 1.

FIG. 1 illustrates that the light emitting reaction caused by the obtained luciferase has maximum luminescent wavelength at approximately 564 nm at pH 8.0. The maximum luminescent wavelength was illustrated at approximately 567 nm at pH 7.5, at approximately 605 nm at pH 7.0, at approximately 612 nm at pH 6.5, at approximately 614 nm at pH 6.0, and at approximately 616 nm at pH 5.5.

4. Kinetic Analysis 4-1. Determination of Concentrations of D-Luciferin and ATP

A concentration of D-luciferin in a D-luciferin solution and that of ATP in an ATP solution were determined as described below.

With use of UV-Visible Spectrometer (manufactured by Hitachi), ultraviolet visible absorption spectra were measured for the D-luciferin solution and ATP solution. Based on the measurement results and ϵ values indicated below, each concentration was calculated.

D-luciferin: $\lambda_{max}$ 328 nm, ϵ 18200, pH 5.0

ATP: $\lambda_{max}$ 259 nm, ϵ 15400, pH 7.0.

The measurements were carried out ten times for each sample, and the average of absorbency was used for the calculation. The Km value was calculated as it is described below by using the D-luciferin solution and ATP solution whose concentrations were determined as described above.

4-2. Measurement of Km for D-Luciferin

Under various concentrations of D-luciferin, the luminescence intensity was measured for the obtained luciferase. Based on the measurement results, Km values with respect to D-luciferin were calculated.

Eight types of D-luciferin solution of various concentrations were prepared by adding D-luciferin to 0.1 M Tris-HCl (pH 8.0). These solutions contain D-luciferin at final concentrations of 0.625, 1.25, 2.5, 5, 10, 20, 40, and 80 μM. These D-luciferin solutions were aliquoted into 96-well microplate at a volume of 50 μL each. A solution of 0.1 M Tris-HCl (pH 8.0) containing each of the purified luciferase, 4 mM of ATP, and 8 mM of $MgSO_4$ was connected to the standard pump of the luminometer, and the measurements was carried out at the same time as addition of 50 μL of the solution to the well. A Luminescensor (manufactured by ATTO Corporation) was used for the measurements. Measurements were repeated 3 times for each luciferin concentration.

The peak intensity of the obtained photon count value was plotted with respect to luciferin concentration S, defining the initial rate as V. The plots were subjected to curve fitting of Michaelis Menten type, thereby giving Km values. The curve fitting was performed by a nonlinear least-squares method, and the search of the parameter was performed by a Newton method.

4-3. Measurement of Km Value with Respect to ATP

Under various ATP concentrations, the luminescence intensity of the obtained luciferase was measured. Based on the results, Km values with respect to ATP was determined.

Various 8 types of ATP solutions with different concentrations were prepared by adding ATP to 0.1 M Tris-HCl (pH 8.0). These solutions contain ATP at final concentration of 10, 20, 40, 80, 160, 320, 480, and 640 µM. These ATP solutions were aliquoted into a 96-well microplate at a volume of 50 µl each. 0.1 M Tris-HCl (pH 8.0) solution containing each purified luciferase, 1 mM of D-luciferin, and 8 mM of $MgSO_4$ was connected to a standard pump of a luminometer, and the measurement was carried out at the same time as addition of 50 µL of the solution to wells. Measurement was repeated 3 times for each ATP concentration.

The peak intensities of the obtained photon count value were plotted with respect to ATP concentration S, with an initial rate V. The plots were subjected to curve fitting of Michaelis Menten type, thereby giving Km value. The curve fitting was performed by a nonlinear least-squares method, and the search of the parameter was performed by a Newton method.

Km values with respect to D-luciferin and Km values with respect to ATP which were determined as described above were shown in the Table 3. Table 3 also indicates Km values for known firefly luciferases, measured in a similar manner. GL3 is a luciferase derived from *P. pyralis*. Further, ELuc, CBG, and CBR are luciferases derived from known click beetles. These known beetle luciferases that are commercially available were used.

TABLE 3

Comparison of Km value

| | Km | |
|---|---|---|
| | D-luciferin (µM) | ATP (µM) |
| L. accensa | 16 | 47.6 |
| GL3 | 15.7 | 64.3 |
| ELuc | 12.7 | 182 |
| CBG | 1.44 | 58.4 |
| CBR | 33.3 | 47 |

Further, FIG. 2 indicates these Km values as plots with respect to D-luciferin concentration (horizontal axis) and ATP concentration (vertical axis).

Example 3

Comparison of Luminescence Intensity by Luciferase Derived from *P. Pyralis*

Each of the wild type luciferase derived from *L. accensa*, the mutant luciferase derived from *L. accensa* (N50D and 1530R), and the luciferase derived from *P. pyralis* (SEQ ID NO: 33) was expressed in a HeLa cell, and the luminescence intensity was measured and compared to each other.

The expression vector containing the wild type luciferase gene was constructed as follows. In particular, with respect to the wild type luciferase, a Kozak sequence is given to a nucleic acid (SEQ ID NO: 5) containing a gene optimized for mammalian cell expression, and the resultant was inserted between SgfI and PmeI sites within the multicloning site of pF9A CMV hRLuc neo Flexi vector (manufactured by Promega). Herein below, the base sequences are described:

(SEQ ID NO: 5)
ATGGAAGAGGACAAGAACATCCTGAGAGGCCCTGCCCCATTCTACCCCCT

GGAAGATGGCACAGCCGGCGAGCAGCTGCACCGGGCCATGAAGAGATACG

CCCTGATCCCCGGCACAATCGCCTTCACAGACGCCCACGCCGGAGTGAAC

ATCACCTACAGCGAGTACTTCGAGATGGCCTGTAGACTGGCCGAGAGCCT

GAAGAGATATGGCCTGGGACTGCAGCATCGGATCGTGGTCTGCAGCGAGA

ACAGCCTGCAGTTCTTCATGCCCGTGGTCGGAGCCCTGTTCATCGGAGTG

GGCGTGGCCCCTGCCAACGACATCTACAACGAGCGCGAGCTGCTGAACAG

CATGACCATCAGCCAGCCCACCCTGGTGTTCTGCAGCCGGAAGGGCCTGC

AGAAAATCCTGAACGTGCAGAAAAAGCTGCCCGTGATCCAGAAGATCATC

ATCCTGGACACCAAAGAGGACTACATGGGCTTCCAGAGCATGTACAGCTT

CGTGGACAGCCAGCTGCCTGTGGGCTTCAACGAGTACGACTACGTGCCCG

ACAGCTTCGACCGGGATCAGGCCACCGCCCTGATCATGAACAGCAGCGGC

AGCACCGGCCTGCCCAAGGGCGTGGAACTGAACCACACCAGCGTGTGCGT

GCGGTTCAGCCACTGCAGGGACCCCGTGTACGGCAACCAGATCATCCCCG

ACACCGCCATCCTGAGCGTGATCCCTTTCCACCACGGCTTCGGCATGTTC

ACCACCCTGGGCTACCTGATCTGCGGCTTCCGGGTGGTGCTGATGTACAG

ATTCGAGGAAGAACTGTTCCTGCGGAGCCTGCAGGACTACAAGATCCAGA

GCGCCCTGCTGGTGCCTACCCTGTTCAGCTTCTTCGCCAAGAGCACACTG

ATCGATAAGTACGACCTGAGCAACCTGCACGAGATCGCCAGCGGCGGAGC

CCCCCTGGCCAAAGAAGTGGGAGAGGCCGTCGCCAAGCGGTTCAACCTGC

GGGGCATCAGACAGGGCTACGGCCTGACCGAGACAACCAGCGCCGTGATC

ATCACCCCCGAGGGCGACGATAAGCCTGGCGCCGTGGGCAAGGTGGTGCC

ATTCTTCAGCGCCAAGGTGGTGGACCTGGACACCGGCAAGACCCTGGGCG

TGAACCAGAGGGGCGAGCTGTGCCTGAAGGGCCCCATGATCATGAAGGGC

TACGTGAACAACCCCGAGGCCACCAATGCCCTGATCGACAAGGACGGCTG

GCTGCACAGCGGCGACATCAGCTACTGGGACGAGGACGGCCACTTCTTCA

TCGTGGACCGGCTGAAGTCCCTGATCAAGTACAAGGGCTACCAGGTGCCC

CCTGCCGAGCTGGAATCCATCCTGCTGCAGCACCCCTTCATCTTCGATGC

CGGCGTGGCCGGAATCCCCGATGATGAAGCCGGCGAACTGCCTGCCGCCG

TGGTGGTGCTGGAAGAGGGAAAGACCATGACCGAGAAAGAAATCATGGAC

TACGTGGCCGGACAGGTCACAACCGCCAAGAGACTGAGAGGCGGCGTGGT

GTTCGTGGACGAGGTGCCAAAGGGACTGACCGGCAAGATCGACGCCCGGA

AGATCCGCGAGATCCTGGTGAAAGTGAAAAAGACCAAGAGCAAGCTGTG

A.

The expression vector containing the mutant luciferase gene was prepared as follows. First, the mutant luciferase gene was prepared. Mutation was introduced two positions in the wild type luciferase gene (SEQ ID NO: 5), which has been prepared by codon optimization as described above, by using a primer for mutation. The introduction of genetic mutation was carried out by following the method described in "An experimental method of gene functional inhibition-from simple and secure gene function analysis to application to gene therapy" edited by Kazunari Taira (Yodosha, published in 2001, pages 17 to 25). As a result of the introduction of mutation, the amino acid residue at position 50 in the amino acid sequence of a protein encoded by the gene, i.e., asparagine, was changed to aspartic acid (N50D), and the amino acid residue at position 530, i.e., isoleucine, was changed to arginine (I530R). To the *Lucidina accensa* luciferase gene obtained by introducing a mutation (SEQ ID NO: 32), a Kozak sequence was given and the resultant was inserted between SgfI and PmeI sites within the multicloning site of pF9A CMV hRLuc neo Flexi vector. Herein below, the base sequence is described:

(SEQ ID NO: 32)
ATGGAAGAGGACAAGAACATCCTGAGAGGCCCTGCCCCATTCTACCCCCT

GGAAGATGGCACAGCCGGCGAGCAGCTGCACCGGGCCATGAAGAGATACG

CCCTGATCCCCGGCACAATCGCCTTCACAGACGCCCACGCCGGAGTGGAC

ATCACCTACAGCGAGTACTTCGAGATGGCCTGTAGACTGGCCGAGAGCCT

GAAGAGATATGGCCTGGGACTGCAGCATCGGATCGTGGTCTGCAGCGAGA

ACAGCCTGCAGTTCTTCATGCCCGTGGTCGGAGCCCTGTTCATCGGAGTG

GGCGTGGCCCCTGCCAACGACATCTACAACGAGCGCGAGCTGCTGAACAG

CATGACCATCAGCCAGCCCACCCTGGTGTTCTGCAGCCGGAAGGGCCTGC

AGAAAATCCTGAACGTGCAGAAAAAGCTGCCCGTGATCCAGAAGATCATC

ATCCTGGACACCAAAGAGGACTACATGGGCTTCCAGAGCATGTACAGCTT

CGTGGACAGCCAGCTGCCTGTGGGCTTCAACGAGTACGACTACGTGCCCG

ACAGCTTCGACCGGGATCAGGCCACCGCCCTGATCATGAACAGCAGCGGC

AGCACCGGCCTGCCCAAGGGCGTGGAACTGAACCACACCAGCGTGTGCGT

GCGGTTCAGCCACTGCAGGGACCCCGTGTACGGCAACCAGATCATCCCCG

ACACCGCCATCCTGAGCGTGATCCCTTTCCACCACGGCTTCGGCATGTTC

ACCACCCTGGGCTACCTGATCTGCGGCTTCCGGGTGGTGCTGATGTACAG

ATTCGAGGAAGAACTGTTCCTGCGGAGCCTGCAGGACTACAAGATCCAGA

GCGCCCTGCTGGTGCCTACCCTGTTCAGCTTCTTCGCCAAGAGCACACTG

ATCGATAAGTACGACCTGAGCAACCTGCACGAGATCGCCAGCGGCGGAGC

CCCCCTGGCCAAAGAAGTGGGAGAGGCCGTCGCCAAGCGGTTCAACCTGC

GGGGCATCAGACAGGGCTACGGCCTGACCGAGACAACCAGCGCCGTGATC

ATCACCCCCGAGGGCGACGATAAGCCTGGCGCCGTGGGCAAGGTGGTGCC

ATTCTTCAGCGCCAAGGTGGTGGACCTGGACACCGGCAAGACCCTGGGCG

TGAACCAGAGGGGCGAGCTGTGCCTGAAGGGCCCCATGATCATGAAGGGC

TACGTGAACAACCCCGAGGCCACCAATGCCCTGATCGACAAGGACGGCTG

GCTGCACAGCGGCGACATCAGCTACTGGGACGAGGACGGCCACTTCTTCA

TCGTGGACCGGCTGAAGTCCCTGATCAAGTACAAGGGCTACCAGGTGCCC

CCTGCCGAGCTGGAATCCATCCTGCTGCAGCACCCCTTCATCTTCGATGC

CGGCGTGGCCGGAATCCCCGATGATGAAGCCGGCGAACTGCCTGCCGCCG

TGGTGGTGCTGGAAGAGGGAAAGACCATGACCGAGAAAGAAATCATGGAC

TACGTGGCCGGACAGGTCACAACCGCCAAGAGACTGAGAGGCGGCGTGGT

GTTCGTGGACGAGGTGCCAAAGGGACTGACCGGCAAGAGAGACGCCCGGA

AGATCCGCGAGATCCTGGTGAAAGTGAAAAAGACCAAGAGCAAGCTGTG

A.

The expression vector containing the luciferase gene derived from *P. pyralis* was prepared as follows. Specifically, an existing luciferase gene derived from *P. pyralis* was optimized for mammalian cell expression, given with a Kozak sequence, and then inserted between SgfI and PmeI sites within the multicloning site of pF9A CMV hRLuc neo Flexi vector.

Further, since the pF9A vector contains the luciferase gene derived from *Renilla reniformis* as an internal control, it is possible to obtain the luminescence intensity from the luminescent gene inserted to the multicloning site as a ratio compared to the luminescence intensity emitted by the *Renilla* luciferase.

Three types of plasmids obtained in such a manner described above were each subjected to gene transfection to a HeLa cell, which has been inoculated in a 24-well plate, by a lipofection method, and 24 hours later, the cells were washed with PBS. To each well of a 24-well plate, 500 µL of 2 mM D-luciferin/$CO_2$ Independent Medium (manufactured by Invitrogen) was added and the luminescence intensity was measured for 90 min by using a Luminescensor (manufactured by ATTO Corporation) under the condition including 25° C. and 1 sec per each well. The luminescence intensity which is obtained at the time point of 90 min after starting the measurement was taken as the luminescence intensity of the wild type luciferase, the mutant luciferase, and *P. pyralis* luciferase. The culture medium was removed from each well, which was then washed three times with PBS. Subsequently, 500 µL of 10 µM coelenterazine/$CO_2$ Independent Medium was added to each well and the luminescence intensity was measured for 30 min by using a Luminescensor under the condition including 25° C. and 1 sec per each well. The luminescence intensity obtained at five minutes after the addition of coelenterazine was taken as luminescence intensity of the *Renilla* luciferase, which is an internal control. Each of the luminescence intensity from the wild type luciferase, the mutant luciferase, and *P. pyralis* luciferase was divided by the luminescence intensity of the *Renilla* luciferase, and the results are illustrated as a graph illustrating the luminescence intensity of each luciferase. The result is given in FIG. 3.

*P. pyralis* luciferase, the wild type luciferase, and the mutant luciferase exhibited the luminescence intensity of 6.6, 7.3, and 26.5, respectively. Thus, the wild type luciferase exhibited 1.1 times or more the luminescence intensity in comparison to the luminescence intensity of *P. pyralis* luciferase. The mutant luciferase exhibited 4 times or more the luminescence intensity in comparison to the luminescence intensity of *P. pyralis* luciferase. The mutant luciferase exhibited 3.6 times or more the luminescence intensity in comparison to the luminescence intensity of the wild type luciferase.

Example 4

Stability Determination

Stability against degradation was determined for the wild type luciferase derived from *L. accensa* in comparison with a known luciferase derived from *L. biplagiata*.

The amino acid sequence of the luciferase derived from *L. biplagiata* is disclosed in the literature (Oba Y, Furuhashi M, Inouye S. (2010) Identification of a functional luciferase gene in the non-luminous diurnal firefly, *Lucidina biplagiata*. Molecular Insect Biology 19 (6): 737 to 743) (SEQ ID NO: 30, herein below, this sequence is referred to as a "literature sequence"). Meanwhile, the present inventors cloned the luciferase from an adult insect of *L. biplagiata*, which had been collected from Hachioji, Tokyo metropolitan, and identified the amino sequence of the luciferase (SEQ ID NO: 31, herein below, this sequence is referred to as a "cloned sequence"). As a result of amino acid sequence comparison, it was found that the amino acid at position 249 is lysine in the literature sequence while it is methionine in the cloned sequence. The base sequence is described herein below:

(SEQ ID NO: 31)
MEEDKNILRGPAAFYPLEDGTAGEQLHRAMKRYALIPGTIAFTDAHAGVN

ITYSEYFEMACRLAESLKRYGLGLQHRIVVCSENSLQFFMPVVGALFIGV

GVAPANDIYNERELLNSMTISQPTLVFCSRKGLQKILNVQKKLPVIQKII

ILDTKEDYMGFQSMYSFVDSQLPVGFNEYDYVPDSFDRDQATALIMNSSG

STGLPKGVELTHTSVCVRFSHCRDPVFGNQIIPDTAILSVIPFHHGFGMF

TTLGYLICGFRVVLMYRFEEELFLRSLQDYKIQSALLVPTLFSFFAKSTL

IDKYDLSNLHEIASGGAPLAKEVGEAVAKRFNLRGIRQGYGLTETTSAVI

ITPEGDDKPGAVGKVVPFFSAKVVDLDTGKTLGVNQRGELCLKGPMIMKG

YVNNPEATNALIDKDGWLHSGDISYWDEDGHFFIVDRLKSLIKYKGYQVP

PAELESILLQHPFIFDAGVAGIPDDEAGELPAAVVVLEEGKTMTEKEIMD

YVAGQVTTAKRLRGGVVFVDEVPKGLTGKLDARKIREILVKAKKTKSK

L*.

When the amino acid sequence of the luciferase derived from *L. biplagiata* is compared to the amino acid sequence of the wild type luciferase, there were differences as described in the following Table 4. Specifically, when the literature sequence of the luciferase derived from *L. biplagiata* (SEQ ID NO: 30) is compared to the amino acid sequence of the wild type luciferase (SEQ ID NO: 1), it was found that six amino acids are different and there is sequence homology of 98.9%.

TABLE 4

Difference in amino acid residues among various luciferases

| | Amino acid residue number having difference | | | | | |
|---|---|---|---|---|---|---|
| | 13 | 211 | 227 | 249 | 530 | 542 |
| *L. accensa* (wild type) (SEQ ID NO: 1) | Pro | Asn | Tyr | Met | Ile | Val |
| *L. biplagiata* (literature sequence) (SEQ ID NO: 30) | Ala | Thr | Phe | Lys | Leu | Ala |
| *L. biplagiata* (cloned sequence) (SEQ ID NO: 31) | Ala | Thr | Phe | Met | Leu | Ala |

The above three genes were introduced into an expression vector and expressed in *E. coli*. The expression was carried out in the same manner as the Example 2 except that BL21 (DE3) CodonPlus (manufactured by Stratagene Corporation) was used as *E. coli* strain and the cells were cultured appropriately.

The lysate was prepared from the *E. coli* expressing each gene, and then subjected to SDS-polyacrylamide gel electrophoresis. The results obtained from staining the gel is given in FIG. 4. It was confirmed that, as a band with the biggest size, a single band is present near 70 kDa for all three kinds of protein. In the wild type luciferase (i.e., center lane), no other band was identified. Meanwhile, in the luciferase derived from *L. biplagiata* (i.e., left and right lanes), several bands with a size smaller than 70 kDa were identified. In particular, in the luciferase having the literature sequence (i.e., left lane), the gel was stained in a smear shape in the region of 70 kDa or less.

The results illustrated in FIG. 4 indicate that the luciferase derived from *L. biplagiata* was degraded to a significant level while the wild type luciferase was hardly degraded. In other words, it was found that the wild type luciferase has higher stability against protein degradation in comparison to the luciferase derived from *L. biplagiata*.

Example 5

Comparison of Luminescence Intensity by Luciferase Derived from *L. biplagiata*

The luminescence intensity from the light emitting reaction using the wild type luciferase derived from *L. accensa* (SEQ ID NO: 1) was compared to the luminescence intensity from the light emitting reaction using the luciferase derived from *L. biplagiata* having the literature sequence (SEQ ID NO: 30) or the luciferase derived from *L. biplagiata* having the cloned sequence (SEQ ID NO: 31). Further, based on the difference between the literature sequence and the cloned sequence, the amino acid residue at position 249 of the amino acid sequence of the wild type luciferase, i.e., methionine, was changed to lysine to prepare the mutant luciferase (M249K), which was then used for the intensity measurement.

With regard to the four types of the luciferase, a nucleic acid containing a gene optimized for mammalian cell expression was given with a Kozak sequence, and then inserted between SgfI and PmeI sites within the multicloning site of pF9A CMV hRLuc neo Flexi vector (manufactured by Promega). Further, since the pF9A vector contains the luciferase gene derived from *Renilla reniformis* as an internal control in the vector sequence, it is possible to obtain the luminescence intensity from the luminescent gene inserted to the multicloning site as a ratio compared to the luminescence intensity emitted by the *Renilla* luciferase.

Four types of luciferase plasmids obtained in such a manner described above were each subjected to gene transfection to HeLa cells inoculated in a 48-well plate by a lipofection method, and 24 hours later, the cells were washed with PBS. To each well of a 48-well plate, 500 μL of 2 mM D-luciferin/$CO_2$ Independent Medium (manufactured by Invitrogen) was added and the luminescence intensity was measured for 90 min by using a Luminescensor (manufactured by ATTO Corporation) under the condition including 37° C. and 1 sec per each well. The luminescence intensity which is obtained at the time point of 90 min after starting the measurement was taken as the luminescence intensity of each luciferase. The culture medium was removed from each well, which was then washed three times with PBS. Subsequently, 500 μL of 10 μM coelenterazine/$CO_2$ Independent Medium was added to each well and the luminescence intensity was measured for 30 min by using a Luminescensor under the condition including 37° C. and 1 sec per each well. The luminescence intensity obtained at five minutes after the addition of coelenterazine was taken as luminescence intensity of the *Renilla* luciferase, which is an internal control. Each of the luminescence intensities from the luciferases was divided by the luminescence intensity of the *Renilla* luciferase, yielding the luminescence intensity of each luciferase. The results are given in the Table 5 and FIG. 5. The measurements were carried out multiple times for each luciferase, and the luminescence intensity was obtained as a mean value.

TABLE 5

|  | L. Accensa (wild type) | L. Biplagiata (cloned sequence) | L. Biplagiata (literature sequence) | L. Accensa (M249K mutant) |
| --- | --- | --- | --- | --- |
| Mean value | 3.48 | 0.63 | 0.12 | 0.10 |
| Standard deviation | 1.88 | 0.16 | 0.02 | 0.02 |

The wild type luciferase exhibited 5.5 times or more the luminescence intensity from a light emitting reaction in comparison to the luminescence intensity from a light emitting reaction by the luciferase derived from *L. biplagiata* which has the cloned sequence. Further, the wild type luciferase exhibited 29 times or more the luminescence intensity from a light emitting reaction in comparison to the luminescence intensity from a light emitting reaction by the luciferase derived from *L. biplagiata* which has the literature sequence. Based on these results, it was found that the wild type luciferase can cause very high luminescence intensity compared to the luciferase derived from *L. biplagiata*.

Further, with regard to the difference in amino acid residue at position 249 of the amino acid sequence, 34.8 times or more the luminescence intensity was obtained by using the wild type luciferase (methionine at position 249) compared to the luminescence intensity from the mutant luciferase M249K (lysine at position 249). Further, 5.25 times or more the luminescence intensity was obtained by using the luciferase derived from *L. biplagiata* having the cloned sequence (methionine at position 249) compared to the luminescence intensity from the luciferase derived from *L. biplagiata* having the literature sequence (lysine at position 249). Based on these results, it was demonstrated that the methionine residues at position 249 of the amino acid sequence is important for the light emission activity of a luciferase.

Example 6

Obtainment of Mutant Having Shifted Maximum Luminescent Wavelength

By replacing the phenylalanine (F) residue at position 294 of the amino acid sequence of the wild type luciferase which is derived from *L. accensa* with a tyrosine (Y) residue (F294Y), replacing the valine (V) residue at position 323 with a leucine (L) residue (V323L), and replacing the glutamic acid (E) residue at position 354 with a valine (V) residue (E354V), the mutant luciferase (F294Y, V323L, and E354V) was prepared.

Further, by replacing the glutamic acid (E) residue at position 322 of the amino acid sequence of the wild type luciferase with a tryptophan (W) residue (E322W), the mutant luciferase (E322W) was prepared.

Specifically, by introducing a mutation into the gene of the wild type luciferase by appropriately using a primer for mutation, two types of the mutant luciferase gene were obtained. The introduction of genetic mutation was carried out by following the method described in "An experimental method of gene functional inhibition-from simple and secure gene function analysis to application to gene therapy" edited by Kazunari Taira (Yodosha, published in 2001, pages 17 to 25).

The amino acid sequence of thus-prepared mutant luciferase (F294Y, V323L, and E354V) is as follows:

(SEQ ID NO: 34)
MEEDKNILRGPAPFYPLEDGTAGEQLHRAMKRYALIPGTIAFTDAHAGVN

ITYSEYFEMACRLAESLKRYGLGLQHRIVVCSENSLQFFMPVVGALFIGV

GVAPANDIYNERELLNSMTISQPTLVFCSRKGLQKILNVQKKLPVIQKII

ILDTKEDYMGFQSMYSFVDSQLPVGFNEYDYVPDSFDRDQATALIMNSSG

STGLPKGVELNHTSVCVRFSHCRDPVYGNQIIPDTAILSVIPFHHGFGMF

TTLGYLICGFRVVLMYRFEEELFLRSLQDYKIQSALLVPTLFSYFAKSTL

IDKYDLSNLHEIASGGAPLAKELGEAVAKRFNLRGIRQGYGLTETTSAVI

ITPVGDDKPGAVGKVVPFFSAKVVDLDTGKTLGVNQRGELCLKGPMIMKG

YVNNPEATNALIDKDGWLHSGDISYWDEDGHFFIVDRLKSLIKYKGYQVP

PAELESILLQHPFIFDAGVAGIPDDEAGELPAAVVVLEEGKTMTEKEIMD

YVAGQVTTAKRLRGGVVFVDEVPKGLTGKIDARKIREILVKVKKTKSKL.

The base sequence of the gene of thus-prepared mutant luciferase (F294Y, V323L, and E354V) is as follows:

(SEQ ID NO: 38)
ATGGAAGAGGATAAAAATATTCTGCGCGGCCCAGCGCCATTCTATCCTTT

AGAAGATGGAACTGCAGGCGAACAATTACATAGAGCGATGAAAAGATATG

CCTTAATTCCAGGAACCATCGCTTTCACGGACGCTCATGCGGGAGTAAAT

ATCACGTACTCCGAATATTTCGAAATGGCATGCCGATTAGCTGAAAGTTT

GAAAAGATACGGACTTGGATTACAGCACAGAATTGTTGTGTGTAGTGAAA

ATTCTCTACAATTTTTTATGCCCGTCGTGGGTGCCCTATTTATTGGAGTG

GGGGTCGCACCAGCAAATGATATTTATAACGAGCGTGAATTACTCAATAG

CATGACCATATCGCAGCCCACCTTAGTCTTCTGCTCCAGAAAAGGATTGC

AAAAAATTTTGAACGTACAGAAAAAATTACCAGTAATTCAAAAAATTATT

ATTCTGGATACTAAAGAGGATTATATGGGATTTCAGTCAATGTACTCATT

TGTTGACTCGCAATTACCAGTAGGTTTCAACGAATATGATTATGTACCGG

ACTCCTTCGACCGCGATCAAGCAACGGCACTTATAATGAACTCCTCTGGA

TCTACTGGGTTGCCGAAAGGGGTGGAGCTTAACCACACGAGTGTTTGGTT

CAGATTTTCGCATTGCAGAGATCCTGTTTATGGGAATCAAATTATTCCCG

ATACTGCAATTTTAAGTGTTATCCCATTCCATCATGGATTTGGGATGTTT

ACAACGCTAGGATATTTAATATGTGGATTTCGAGTTGTGCTGATGTATAG

ATTTGAAGAAGAACTATTTTTGCGATCCCTTCAAGATTATAAAATTCAGA

GTGCGTTACTAGTACCCACCCTATTTTCGTACTTTGCGAAAAGCACTCTA

ATTGACAAGTACGATTTATCCAATTTACATGAAATTGCGTCTGGTGGTGC

TCCCCTCGCAAAAGAACTTGGAGAAGCAGTGGCAAAACGCTTTAACCTTC

GAGGTATACGGCAAGGGTACGGCTTGACCGAAACTACATCGGCCGTTATT

```
ATTACACCTGTGGGAGATGATAAGCCAGGTGCAGTCGGTAAGGTTGTACC

CTTCTTTTCGGCAAAAGTTGTTGATCTCGACACCGGGAAAACTTTGGGAG

TTAATCAAAGGGGCGAATTGTGTCTGAAAGGCCCCATGATTATGAAAGGT

TATGTAAATAACCCTGAAGCTACAAATGCCTTGATCGATAAAGATGGATG

GCTACACTCTGGTGATATATCATACTGGGACGAAGACGGTCACTTCTTCA

TTGTTGATCGCTTGAAATCTTTGATTAAATATAAAGGGTACCAGGTACCG

CCCGCTGAATTGGAATCCATTTTGCTGCAACATCCCTTTATCTTCGATGC

AGGGGTGGCTGGGATTCCCGACGATGAAGCCGGTGAATTGCCCGCTGCGC

TTGTTGTTTTAGAGGAAGGAAAAACTATGACTGAAAAAGAAATCATGGAT

TATGTGGCAGGTCAGGTAACTACAGCAAAACGGCTACGTGGAGGTGTCGT

ATTCGTCGATGAAGTGCCGAAGGGTCTCACTGGGAAAATCGATGCACGAA

AAATTAGAGAAATACTTGTGAAAGTAAAGAAAACCAAATCAAAATTGTA

A.
```

Further, a gene of the mutant luciferase (F294Y, V323L, and E354V) containing a gene optimized for mammalian cell expression was produced. The base sequence thereof is as follows:

```
                                               (SEQ ID NO: 35)
ATGGAAGAGGACAAGAACATCCTGAGAGGCCCTGCCCCATTCTACCCCCT

GGAAGATGGCACAGCCGGCGAGCAGCTGCACCGGGCCATGAAGAGATACG

CCCTGATCCCCGGCACAATCGCCTTCACAGACGCCCACGCCGGAGTGAAC

ATCACCTACAGCGAGTACTTCGAGATGGCCTGTAGACTGGCCGAGAGCCT

GAAGAGATATGGCCTGGGACTGCAGCATCGGATCGTGGTCTGCAGCGAGA

CAGCCTGCAGTTCTTCATGCCCGTGGTCGGAGCCCTGTTCATCGGAGTG

GGCGTGGCCCCTGCCAACGACATCTACAACGAGCGCGAGCTGCTGAACAG

CATGACCATCAGCCAGCCCACCCTGGTGTTCTGCAGCCGGAAGGGCCTGC

AGAAAATCCTGAACGTGCAGAAAAAGCTGCCCGTGATCCAGAAGATCATC

ATCCTGGACACCAAAGAGGACTACATGGGCTTCCAGAGCATGTACAGCTT

CGTGGACAGCCAGCTGCCTGTGGGCTTCAACGAGTACGACTACGTGCCCG

ACAGCTTCGACCGGGATCAGGCCACCGCCCTGATCATGAACAGCAGCGGC

AGCACCGGCCTGCCCAAGGGCGTGGAACTGAACCACACCAGCGTGTGCGT

GCGGTTCAGCCACTGCAGGGACCCCGTGTACGGCAACCAGATCATCCCCG

ACACCGCCATCCTGAGCGTGATCCCTTTCCACCACGGCTTCGGCATGTTC

ACCACCCTGGGCTACCTGATCTGCGGCTTCCGGGTGGTGCTGATGTACAG

ATTCGAGGAAGAACTGTTCCTGCGGAGCCTGCAGGACTACAAGATCCAGA

GCGCCCTGCTGGTGCCTACCCTGTTCAGCTaCTTCGCCAAGAGCACACTG

ATCGATAAGTACGACCTGAGCAACCTGCACGAGATCGCCAGCGGCGGAGC

CCCCCTGGCCAAAGAAcTGGGAGAGGCCGTCGCCAAGCGGTTCAACCTGC

GGGGCATCAGACAGGGCTACGGCCTGACCGAGACAACCAGCGCCGTGATC

ATCACCCCCGtGGGCGACGATAAGCCTGGCGCCGTGGGCAAGGTGGTGCC

ATTCTTCAGCGCCAAGGTGGTGGACCTGGACACCGGCAAGACCCTGGGCG

TGAACCAGAGGGGCGAGCTGTGCCTGAAGGGCCCCATGATCATGAAGGGC

TACGTGAACAACCCCGAGGCCACCAATGCCCTGATCGACAAGGACGGCTG

GCTGCACAGCGGCGACATCAGCTACTGGGACGAGGACGGCCACTTCTTCA

TCGTGGACCGGCTGAAGTCCCTGATCAAGTACAAGGGCTACCAGGTGCCC

CCTGCCGAGCTGGAATCCATCCTGCTGCAGCACCCCTTCATCTTCGATGC

CGGCGTGGCCGGAATCCCCGATGATGAAGCCGGCGAACTGCCTGCCGCCG

TGGTGGTGCTGGAAGAGGGAAAGACCATGACCGAGAAAGAAATCATGGAC

TACGTGGCCGGACAGGTCACAACCGCCAAGAGACTGAGAGGCGGCGTGGT

GTTCGTGGACGAGGTGCCAAAGGGACTGACCGGCAAGATCGACGCCCGGA

AGATCCGCGAGATCCTGGTGAAAGTGAAAAAGACCAAGAGCAAGCTGTG
A.
```

Further, the amino acid sequence of thus-prepared mutant luciferase (E322W) is as follows:

```
                                               (SEQ ID NO: 36)
MEEDKNILRGPAPFYPLEDGTAGEQLHRAMKRYALIPGTIAFTDAHAGVN

ITYSEYFEMACRLAESLKRYGLGLQHRIVVCSENSLQFFMPVVGALFIGV

GVAPANDIYNERELLNSMTISQPTLVFCSRKGLQKILNVQKKLPVIQKII

ILDTKEDYMGFQSMYSFVDSQLPVGFNEYDYVPDSFDRDQATALIMNSSG

STGLPKGVELNHTSVCVRFSHCRDPVYGNQIIPDTAILSVIPFHHGFGMF

TTLGYLICGFRVVLMYRFEEELFLRSLQDYKIQSALLVPTLFSFFAKSTL

IDKYDLSNLHEIASGGAPLAKWVGEAVAKRFNLRGIRQGYGLTETTSAVI

ITPEGDDKPGAVGKVVPFFSAKVVDLDTGKTLGVNQRGELCLKGPMIMKG

YVNNPEATNALIDKDGWLHSGDISYWDEDGHFFIVDRLKSLIKYKGYQVP

PAELESILLQHPFIFDAGVAGIPDDEAGELPAAVVVLEEGKTMTEKEIMD

YVAGQVTTAKRLRGGVVFVDEVPKGLTGKIDARKIREILVKVKKTKSKL.
```

The base sequence of the gene of thus-prepared mutant luciferase (E322W) is as follows:

```
                                               (SEQ ID NO: 39)
ATGGAAGAGGATAAAAATATTCTGCGCGGCCCAGCGCCATTCTATCCTTT

AGAAGATGGAACTGCAGGCGAACAATTACATAGAGCGATGAAAAGATATG

CCTTAATTCCAGGAACCATCGCTTTCACGGACGCTCATGCGGGAGTAAAT

ATCACGTACTCCGAATATTTCGAAATGGCATGCCGATTAGCTGAAAGTTT

GAAAAGATACGGACTTGGATTACAGCACAGAATTGTTGTGTGTAGTGAAA

ATTCTCTACAATTTTTTATGCCCGTCGTGGGTGCCCTATTTATTGGAGTG

GGGGTCGCACCAGCAAATGATATTTATAACGAGCGTGAATTACTCAATAG

CATGACCATATCGCAGCCCACCTTAGTCTTCTGCTCCAGAAAAGGATTGC

AAAAAATTTTGAACGTACAGAAAAAATTACCAGTAATTCAAAAAATTATT

ATTCTGGATACTAAAGAGGATTATATGGGATTTCAGTCAATGTACTCATT

TGTTGACTCGCAATTACCAGTAGGTTTCAACGAATATGATTATGTACCGG

ACTCCTTCGACCGCGATCAAGCAACGGCACTTATAATGAACTCCTCTGGA
```

-continued

```
TCTACTGGGTTGCCGAAAGGGGTGGAGCTTAACCACACGAGTGTTTGTGT
CAGATTTTCGCATTGCAGAGATCCTGTTTATGGGAATCAAATTATTCCCG
ATACTGCAATTTTAAGTGTTATCCCATTCCATCATGGATTTGGGATGTTT
ACAACGCTAGGATATTTAATATGTGGATTTCGAGTTGTGCTGATGTATAG
ATTTGAAGAAGAACTATTTTTGCGATCCCTTCAAGATTATAAAATTCAGA
GTGCGTTACTAGTACCCACCCTATTTTCGTTCTTTGCGAAAAGCACTCTA
ATTGACAAGTACGATTTATCCAATTTACATGAAATTGCGTCTGGTGGTGC
TCCCCTCGCAAAATGGGTTGGAGAAGCAGTGGCAAAACGCTTTAACCTTC
GAGGTATACGGCAAGGGTACGGCTTGACCGAAACTACATCGGCCGTTATT
ATTACACCTGAGGGAGATGATAAGCCAGGTGCAGTCGGTAAGGTTGTACC
CTTCTTTTCGGCAAAAGTTGTTGATCTCGACACCGGGAAAACTTTGGGAG
TTAATCAAAGGGGCGAATTGTGTCTGAAAGGCCCCATGATTATGAAAGGT
TATGTAAATAACCCTGAAGCTACAAATGCCTTGATCGATAAAGATGGATG
GCTACACTCTGGTGATATATCATACTGGGACGAAGACGGTCACTTCTTCA
TTGTTGATCGCTTGAAATCTTTGATTAAATATAAAGGGTACCAGGTACCG
CCCGCTGAATTGGAATCCATTTTGCTGCAACATCCCTTTATCTTCGATGC
AGGGGTGGCTGGGATTCCCGACGATGAAGCCGGTGAATTGCCCGCTGCCG
TTGTTGTTTTAGAGGAAGGAAAAACTATGACTGAAAAAGAAATCATGGAT
TATGTGGCAGGTCAGGTAACTACAGCAAAACGGCTACGTGGAGGTGTCGT
ATTCGTCGATGAAGTGCCGAAGGGTCTCACTGGGAAAATCGATGCACGAA
AAATTAGAGAAATACTTGTGAAAGTAAAGAAAACCAAATCAAAATTGTA
A.
```

Further, a gene of the mutant luciferase (E322W) containing a gene optimized for mammalian cell expression was produced. The base sequence thereof is as follows:

```
                                    (SEQ ID NO: 37)
ATGGAAGAGGACAAGAACATCCTGAGAGGCCCTGCCCCATTCTACCCCCT
GGAAGATGGCACAGCCGGCGAGCAGCTGCACCGGGCCATGAAGAGATACG
CCCTGATCCCCGGCACAATCGCCTTCACAGACGCCCACGCCGGAGTGAAC
ATCACCTACAGCGAGTACTTCGAGATGGCCTGTAGACTGGCCGAGAGCCT
GAAGAGATATGGCCTGGGACTGCAGCATCGGATCGTGGTCTGCAGCGAGA
ACAGCCTGCAGTTCTTCATGCCCGTGGTCGGAGCCCTGTTCATCGGAGTG
GGCGTGGCCCCTGCCAACGACATCTACAACGAGCGCGAGCTGCTGAACAG
CATGACCATCAGCCAGCCCACCCTGGTGTTCTGCAGCCGGAAGGGCCTGC
AGAAAATCCTGAACGTGCAGAAAAAGCTGCCCGTGATCCAGAAGATCATC
ATCCTGGACACCAAAGAGGACTACATGGGCTTCCAGAGCATGTACAGCTT
CGTGGACAGCCAGCTGCCTGTGGGCTTCAACGAGTACGACTACGTGCCCG
ACAGCTTCGACCGGGATCAGGCCACCGCCCTGATCATGAACAGCAGCGGC
AGCACCGGCCTGCCCAAGGGCGTGGAACTGAACCACACCAGCGTGTGCGT
GCGGTTCAGCCACTGCAGGGACCCCGTGTACGGCAACCAGATCATCCCCG
ACACCGCCATCCTGAGCGTGATCCCTTTCCACCACGGCTTCGGCATGTTC
ACCACCCTGGGCTACCTGATCTGCGGCTTCCGGGTGGTGCTGATGTACAG
ATTCGAGGAAGAACTGTTCCTGCGGAGCCTGCAGGACTACAAGATCCAGA
GCGCCCTGCTGGTGCCTACCCTGTTCAGCTTCTTCGCCAAGAGCACACTG
ATCGATAAGTACGACCTGAGCAACCTGCACGAGATCGCCAGCGGCGGAGC
CCCCCTGGCCAAAtggGTGGGAGAGGCCGTCGCCAAGCGGTTCAACCTGC
GGGGCATCAGACAGGGCTACGGCCTGACCGAGACAACCAGCGCCGTGATC
ATCACCCCCGAGGGCGACGATAAGCCTGGCGCCGTGGGCAAGGTGGTGCC
ATTCTTCAGCGCCAAGGTGGTGGACCTGGACACCGGCAAGACCCTGGGCG
TGAACCAGAGGGGCGAGCTGTGCCTGAAGGGCCCCATGATCATGAAGGGC
TACGTGAACAACCCCGAGGCCACCAATGCCCTGATCGACAAGGACGGCTG
GCTGCACAGCGGCGACATCAGCTACTGGGACGAGGACGGCCACTTCTTCA
TCGTGGACCGGCTGAAGTCCCTGATCAAGTACAAGGGCTACCAGGTGCCC
CCTGCCGAGCTGGAATCCATCCTGCTGCAGCACCCCTTCATCTTCGATGC
CGGCGTGGCCGGAATCCCCGATGATGAAGCCGGCGAACTGCCTGCCGCCG
TGGTGGTGCTGGAAGAGGGAAAGACCATGACCGAGAAAGAAATCATGGAC
TACGTGGCCGGACAGGTCACAACCGCCAAGAGACTGAGAGGCGGCGTGGT
GTTCGTGGACGAGGTGCCAAAGGGACTGACCGGCAAGATCGACGCCCGGA
AGATCCGCGAGATCCTGGTGAAAGTGAAAAAGACCAAGAGCAAGCTGTG
A.
```

After that, each of thus-prepared genes (SEQ ID NOs: 38 and 39) was introduced into pRSET-B vector according to the same method as the Example 2. This vector was transformed to *E. coli* JM109 (DE3) strain to express the mutant luciferase. Subsequently, the mutant luciferase was purified from *E. coli*. In addition, under various pH environments, the light emission spectrum was measured according to the same method as the Example 2 from a light emitting reaction catalyzed by the mutant luciferase.

In FIG. 6, the light emission spectrum that is obtained from a light emitting reaction by using a mutant luciferase (F294Y, V323L, and E354V) as an enzyme under various pH environments is illustrated. The maximum luminescent wavelength for each spectrum is indicated in the parenthesis next to the pH description. From FIG. 6, it was found that, for this specific mutant luciferase, the maximum luminescent wavelength with the highest intensity is obtained under environment with pH 7.4, with the maximum luminescent wavelength near 615 nm. Further, it was recognized that the change in the maximum luminescent wavelength according to the pH variation is smaller than that of the wild type illustrated in FIG. 1. It was also recognized that, compared to the wild type illustrated in FIG. 1, the shift of the maximum luminescent wavelength to a long wavelength side is significant particularly in the spectra for pH 7.0 or more.

In FIG. 7, the light emission spectrum that is obtained from a light emitting reaction by using a mutant luciferase (E322W) under various pH environments is illustrated. The maximum luminescent wavelength for each spectrum is indicated in the parenthesis next to the pH description. From FIG. 7, it was found that, for this specific mutant luciferase, the maximum luminescent wavelength with the highest intensity is obtained under environment with pH 8.0, with the maximum luminescent wavelength near 557 nm. Further, it was recognized that the light emission spectrum obtained in the environment of pH 6.8, pH 6.6, or pH 6.4 has a shape that is appeared to have an overlap of two peaks. Further, it was recognized that, as the pH decreases, the maximum luminescent wavelength shifts to a long wavelength side. It was also recognized that, compared to the wild type illustrated in FIG. 1, the shift of the maximum luminescent wavelength to a short wavelength side is significant particularly in the spectra of pH 6.8 and pH 7.0.

Example 7

Determination of Temperature Dependency of Luminescence Intensity

Temperature dependency of the luminescence intensity was determined for the two mutant luciferases that are obtained from the Example 6.

Each of the wild type luciferase gene and two kinds of the mutant gene obtained in the Example 6 was introduced into pRSET-B vector and transformed to *E. coli* JM109 (DE3) strain to form a colony. Thus-obtained colony was cultured and applied on a LB agar medium to form again the colony for 24 hours. After that, it was subjected to the heat treatment at 55° C. for 1 hour and kept at room temperature for 1 hour. It was then sprayed with a liquid containing 0.5 mM D-luciferin and a photographic image thereof was taken for 1 min by using a CCD camera (trade name: DP70, manufactured by Olympus Corporation).

Figure 8:
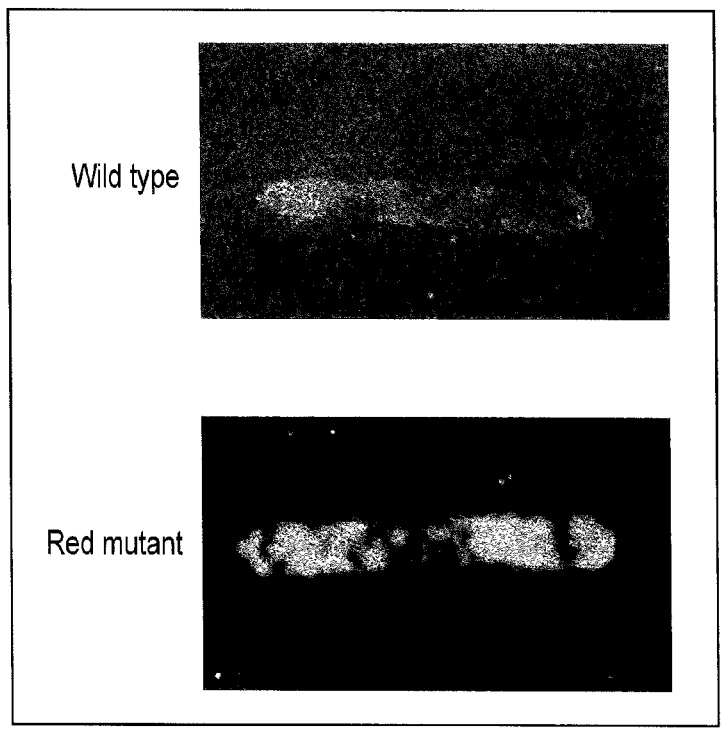
FIG. 8 includes a black and white image showing the light emission from *Escherichia coli* (*E. coli*) kept under 55° C. environment, in which *E. coli* expresses the wild type luciferase derived from *L. accensa* or a mutant (F294Y, V323L, and E354V) luciferase.

FIG. 8 illustrates the comparison of the photographic images between the wild type luciferase and the mutant luciferase (F294Y, V323L, and E354V). It should be noted that the images included in the FIG. 8 are a black and white image that is converted from color images originally taken. In FIG. 8, the image marked as "red mutant" indicates the image of the mutant luciferase. It was found from FIG. 8 that the light emitting reaction caused by *E. coli* which expresses the mutant luciferase exhibits stronger light emission compared to the wild type luciferase at 55° C. This result means that the mutant luciferase maintains its catalytic activity even at 55° C. Further, according to the color photographic image, the *E. coli* which expresses the mutant luciferase shows light emission with a red color while the *E. coli* which expresses the wild type luciferase shows light emission with a yellow color with a hint of orange.

Figure 9:
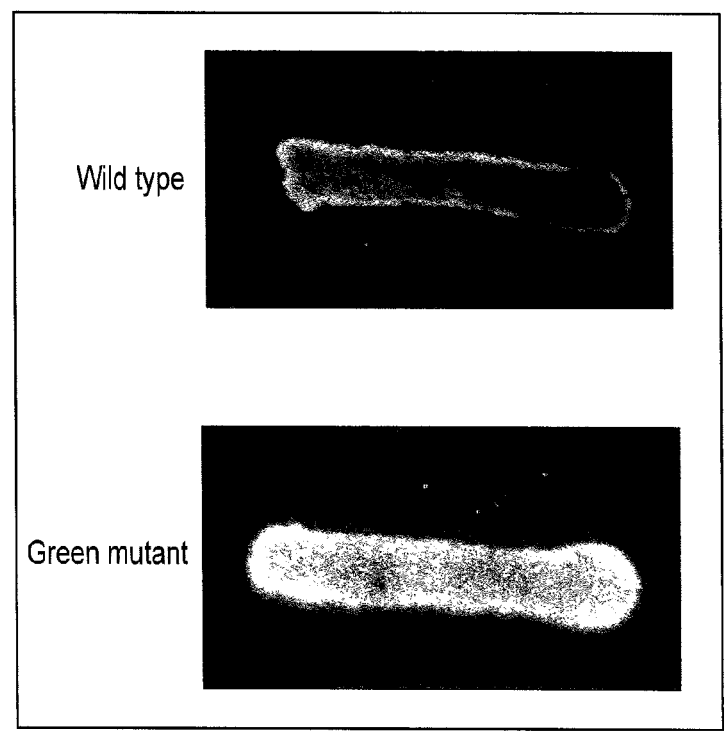
FIG. 9 includes a black and white image showing the light emission from *Escherichia coli* kept under 55° C. environment, in which *E. coli* expresses the wild type luciferase derived from *L. accensa* or a mutant (E322W) luciferase.

FIG. 9 illustrates the comparison of the photographic images between the wild type luciferase and the mutant luciferase (E322W). It should be noted that the images included in the FIG. 9 are a black and white image that is converted from color images originally taken. In FIG. 9, the image marked as "green mutant" indicates the image of the mutant luciferase. It was found from FIG. 8 that the light emitting reaction caused by *E. coli* which expresses the mutant luciferase exhibits stronger light emission compared to the wild type luciferase at 55° C. This result means that the mutant luciferase maintains its catalytic activity even at 55° C. Further, according to the color photographic image, the *E. coli* which expresses the mutant luciferase shows light emission with a yellowish green color while the *E. coli* which expresses the wild type luciferase shows light emission with a yellow color with a hint or orange.

What is claimed is:

1. A protein comprising a luciferase, the luciferase consisting of:
an amino acid sequence selected from the group consisting of the amino acid sequence shown in SEQ NO: 2, the amino acid sequence shown in SEQ ID NO: 34, and the amino acid sequence shown in SEQ ID NO: 36.

2. The protein comprising the luciferase according to claim 1, which catalyzes a reaction of a luciferin to emit light at an intensity that is 4 times or more an intensity of light emitted by the luciferin when the luciferase with the amino acid sequence shown in SEQ ID NO: 33 catalyzes the reaction.

3. The protein comprising the luciferase according to claim 1, which satisfies simultaneously that:
the amino acid residue corresponding to the asparagine at position 50 of the amino acid sequence shown in SEQ ID NO: 30 is aspartic acid, and
the amino acid residue corresponding to the leucine at position 530 of the amino acid sequence shown in SEQ ID NO: 30 is arginine.

4. The luciferase according to claim 1, which shows light emission with the maximum luminescent wavelength of 611 to 615 nm under any pH condition ranging from pH 7.0 to 8.0.

5. The luciferase according to claim 1, which shows light emission with the maximum luminescent wavelength of 568 to 572 nm under any pH condition ranging from pH 6.8 to 7.0.

6. The luciferase according to claim 1, which catalyzes a reaction of a luciferin at 55° C. or more to emit light at an intensity that is higher than an intensity of light emitted by the luciferin when the luciferase with the amino acid sequence shown in SEQ ID NO: 1 catalyzes the reaction at the same temperature.

* * * * *